(12) United States Patent
Shah

(10) Patent No.: US 10,320,735 B2
(45) Date of Patent: Jun. 11, 2019

(54) INTEGRATION OF DEVICES THROUGH A SOCIAL NETWORKING PLATFORM

(71) Applicant: Netspective Communications LLC, Silver Spring, MD (US)

(72) Inventor: Shahid N. Shah, Silver Spring, MD (US)

(73) Assignee: Netspective Communications LLC, Silver Spring, MD (US)

( * ) Notice: Subject to any disclaimer, the term of this patent is extended or adjusted under 35 U.S.C. 154(b) by 489 days.

(21) Appl. No.: 15/275,463

(22) Filed: Sep. 25, 2016

(65) Prior Publication Data

US 2017/0012929 A1 Jan. 12, 2017

Related U.S. Application Data

(62) Division of application No. 14/103,098, filed on Dec. 11, 2013, now Pat. No. 9,525,753.

(60) Provisional application No. 61/736,119, filed on Dec. 12, 2012.

(51) Int. Cl.
| | |
|---|---|
| *H04B 5/00* | (2006.01) |
| *H04W 4/80* | (2018.01) |
| *H04L 12/58* | (2006.01) |
| *H04L 29/06* | (2006.01) |
| *H04L 29/08* | (2006.01) |

(52) U.S. Cl.
CPC .......... *H04L 51/32* (2013.01); *H04B 5/0031* (2013.01); *H04L 67/02* (2013.01); *H04L 67/306* (2013.01); *H04W 4/80* (2018.02); *H04L 63/102* (2013.01); *H04L 63/1433* (2013.01); *H04L 67/303* (2013.01)

(58) Field of Classification Search
CPC .......... H04W 4/80; H04L 51/32; H04L 67/02; H04L 67/306; H04L 67/303; H04L 63/102; H04L 63/1433; H04B 5/0031
USPC .......................................... 709/204
See application file for complete search history.

(56) References Cited

U.S. PATENT DOCUMENTS

| | | | |
|---|---|---|---|
| 8,257,654 B2 | 9/2012 | Maus et al. | |
| 8,490,004 B2 | 7/2013 | Shuster | |
| 8,515,777 B1 * | 8/2013 | Rajasenan | G06Q 50/22 705/2 |
| 9,265,450 B1 * | 2/2016 | Giobbi | G06K 19/0718 |
| 2006/0217113 A1 | 9/2006 | Rao et al. | |

(Continued)

FOREIGN PATENT DOCUMENTS

| | | |
|---|---|---|
| CA | 2419501 A1 | 3/2002 |
| EP | 2579201 A1 | 10/2013 |

(Continued)

*Primary Examiner* — James E Springer
(74) *Attorney, Agent, or Firm* — Rahman LLC

(57) ABSTRACT

A system and method for providing a social networking service to a plurality of devices. A social networking server for facilitating social information exchange among the plurality of devices through a socially aware network. A social profiles manager is coupled to the social networking server that creates and manages individual centric profiles of the plurality of devices. The individual centric profiles of the plurality of devices are social representation of individual devices within the socially aware network. The plurality of devices are identifiable by other participants and the social networking server through their social profiles.

11 Claims, 22 Drawing Sheets

(56) References Cited

U.S. PATENT DOCUMENTS

| | | | |
|---|---|---|---|
| 2008/0004904 A1* | 1/2008 | Tran | A61B 5/0006 |
| | | | 705/2 |
| 2010/0153989 A1 | 6/2010 | Xiangpeng et al. | |
| 2010/0257239 A1 | 10/2010 | Roberts | |
| 2011/0106561 A1* | 5/2011 | Eaton, Jr. | G06Q 10/087 |
| | | | 705/3 |
| 2011/0167133 A1* | 7/2011 | Jain | H04L 67/12 |
| | | | 709/219 |
| 2011/0225417 A1 | 9/2011 | Maharajh et al. | |
| 2011/0270923 A1 | 11/2011 | Jones et al. | |
| 2012/0036015 A1 | 2/2012 | Sheikh | |
| 2012/0188087 A1 | 7/2012 | Wang | |
| 2012/0258665 A1 | 10/2012 | Sip | |
| 2012/0281686 A1 | 11/2012 | Pollari | |
| 2013/0017791 A1 | 1/2013 | Wang et al. | |
| 2013/0023215 A1 | 1/2013 | Wang | |
| 2013/0054481 A1* | 2/2013 | Upadhyaya | G06Q 50/01 |
| | | | 705/319 |
| 2013/0072114 A1 | 3/2013 | Abhyanker | |
| 2013/0091208 A1 | 4/2013 | Rajakarunanayake et al. | |
| 2013/0091210 A1 | 4/2013 | Rajakarunanayake et al. | |
| 2013/0091212 A1 | 4/2013 | Rajakarunanayake et al. | |
| 2013/0091213 A1 | 4/2013 | Diab et al. | |
| 2013/0091540 A1 | 4/2013 | Chen et al. | |
| 2013/0091582 A1 | 4/2013 | Chen et al. | |
| 2013/0132109 A1* | 5/2013 | Mruthyunjaya | G06Q 50/22 |
| | | | 705/2 |
| 2013/0144785 A1 | 6/2013 | Karpenko et al. | |
| 2013/0179951 A1 | 7/2013 | Broustis et al. | |
| 2013/0252594 A1 | 9/2013 | Faillaci et al. | |
| 2013/0276124 A1 | 11/2013 | Tahir et al. | |
| 2014/0018637 A1* | 1/2014 | Bennett | A61N 2/02 |
| | | | 600/301 |
| 2014/0067656 A1 | 3/2014 | Cohen et al. | |
| 2014/0081898 A1* | 3/2014 | Saigal | G06N 5/048 |
| | | | 706/52 |
| 2014/0259111 A1 | 9/2014 | Sampigethaya | |
| 2014/0279027 A1 | 9/2014 | Chou | |
| 2014/0365380 A1 | 12/2014 | Kolay et al. | |
| 2015/0188913 A1 | 7/2015 | Teixeron et al. | |
| 2015/0304369 A1 | 10/2015 | Sandholm et al. | |
| 2016/0065553 A1 | 3/2016 | Lim | |
| 2016/0164905 A1 | 6/2016 | Pinney Wood et al. | |
| 2016/0173520 A1 | 6/2016 | Foster et al. | |

FOREIGN PATENT DOCUMENTS

| | | |
|---|---|---|
| WO | WO2001045014 A1 | 6/2001 |
| WO | WO2001045793 A1 | 6/2001 |
| WO | WO2013051009 A2 | 4/2013 |
| WO | WO2013141764 A1 | 9/2013 |

* cited by examiner

INTEGRATION OF DEVICES THROUGH A SOCIAL NETWORKING PLATFORM

CROSS-REFERENCE TO RELATED APPLICATIONS

This application claims the benefit of U.S. Ser. No. 14/103,098, filed on Dec. 11, 2013, which claims priority to U.S. Provisional Application No. 61/736,119, filed on Dec. 12, 2012, the complete disclosures of which, in their entireties, are hereby incorporated by reference.

BACKGROUND

Technical Field

The embodiments herein generally relate to management and interconnection of devices and in particular to facilitating interconnection and interaction among a plurality of devices through a social networking platform.

Description of the Related Art

Devices interaction and automation is needed in several environments such as medical environment, manufacturing environment, avionics and the like. There are existing systems and procedures for automating and interconnecting the devices. However, still there is a requirement to develop improved systems and methods for the interconnection and automation of devices.

SUMMARY

An embodiment herein provides a system for providing a social networking service to a plurality of participants and allowing the participants to perform a series of social tasks in a socially aware network. The system includes a social networking server that facilitates social information exchange among the participants through the socially aware network. The plurality of participants includes device participants and non-device participants. The system further includes a social profiles manager included in or coupled to the social networking server. The social profiles manager creates and manages individual centric profiles of devices that are a social representation of individual devices within the socially aware network. The devices are identifiable by other participants and the social networking server through social profiles associated with the devices. The social profiles includes social device profiles and social human profiles associated with device participants and non-device participants respectively such that the social human profiles are associated with one or more device profiles, and wherein the social human profiles are represented as a subset of corresponding device profiles. The system further includes a social device manager included in or coupled to the social networking server. The social device manager manages device relationships and social activity in the socially aware network. The system further includes a social networking application comprising a cluster of social applications each for providing a specific social facility to facilitate social activity among the plurality of participants through the socially aware network.

An embodiment herein provides a method for integration of a plurality of participants comprising a plurality of devices and non-devices through a social networking platform. The method includes creating a device centric social profile for each of the plurality of devices. The social profile is a social representation of a respective device within a socially aware network and each device is identifiable by other devices and a social networking server through a social profile of the each device. The method further includes allowing exchange of social content among the devices by the social networking server for the devices to perform a series of social tasks. The social content is exchanged through a first communication channel and a second communication channel. The first communication channel links a device with an external controller and the second communication channel links the external controller with a socially aware network. The series of social tasks includes one or more of voluntarily joining the socially aware network, disassociating or leaving from the socially aware network, extending interconnection with other like-minded devices, sending invitations for connections to other devices, accepting or rejecting invitations from other devices, viewing profiles of other devices, exchanging social activity information, establishing social signatures for social authorization of profiles, creating devices social groups, joining devices groups, and leaving devices groups voluntarily or upon initiation of an activity by a participant. The method further includes maintaining profiles relationships among the devices within the socially aware network.

An embodiment herein provides a method for integration of a plurality of participants comprising a plurality of devices and non-devices through a social networking platform. The method includes creating a device centric social profile for each of the plurality of devices. The social profile is a social representation of a respective device within a socially aware network and the device is identifiable by other devices and a social networking server through the social profile. The method further includes sending a connection invitation by a first device to a second device through a multi-communication channel including a first near field communication (NFC) channel and the socially aware network. The sending of the connection invitation includes sending the connection invitation from the first device to the external controller associated with the first device through the first NFC channel. The sending of the connection invitation further includes transferring the connection invitation from the external controller to a network point of the socially aware network. The sending of the connection invitation further includes transferring the connection invitation from the network point through the socially aware network to the device. The method further includes accepting or rejecting the connection invitation by the second device upon receipt. The method further includes maintaining a profiles relationship of the first device and the second device based on acceptance or rejection of the connection invitation by the second device. The method further includes allowing an exchange of social content through a social activity between the first device and the second device based on the maintained profile relationships. The social activity comprises a series of social tasks including one or more of devices to voluntarily join the socially aware network, disassociate or leave from the socially aware network, extend interconnection with other like-minded devices, send invitations for connections to other devices, accept or reject invitations from other devices, view profiles of other devices, exchange social activity information, establish social signatures for social authorization of profiles, create devices social groups, join devices groups, and leave devices groups voluntarily or upon initiation of an activity by a participant.

An embodiment herein provides a non-transitory program storage device readable by a computer, and comprising a program of instructions executable by the computer to perform a method for integration of a plurality of participants including a plurality of devices and non-devices through a social networking platform. The method includes creating a device centric social profile for each of the plurality of devices. The social profile is a social representation of a respective device within a socially aware network and each device is identifiable by other devices and a social networking server through a social profile of the each device. The method further includes allowing exchange of social content among the devices by the social networking server for the devices to perform a series of social tasks. The social content is exchanged through a first communication channel and a second communication channel. The first communication channel links a device with an external controller and the second communication channel links the external controller with a socially aware network. The series of social tasks includes one or more of voluntarily joining the socially aware network, disassociating or leaving from the socially aware network, extending interconnection with other like-minded devices, sending invitations for connections to other devices, accepting or rejecting invitations from other devices, viewing profiles of other devices, exchanging social activity information, establishing social signatures for social authorization of profiles, creating devices social groups, joining devices groups, and leaving devices groups voluntarily or upon initiation of an activity by a participant. The method further includes maintaining profiles relationships among the devices within the socially aware network.

An embodiment herein provides a system for facilitating sequential, synchronous, and automatically coordinated operation of a plurality of devices through interactive elements involving a chain of tasks and devices. The system includes a social networking server that provides a social networking service to the plurality of devices so that each of the plurality of devices are communicatively connected to the social networking service by associating respective social profiles with the social networking server. The respective social profiles are social representation of the plurality of devices, wherein the social networking server is programmed to allow the plurality of devices to coordinate for a synchronous social times-based functioning by a process. The process includes associating connection type social device relationships between a first device and a second device of the plurality of devices. The connection type social device relationships allow the first device and the second device to view a social profile of one another through a device user interface enabled by the social networking server. The process further includes receiving social content from the first device, wherein the social content is indicative of a social action performed by the first device and an instruction to the second device to perform an action in association with action timelines, and wherein the action timelines are indicative of time points associated with the action and define time when actual action occurs at the plurality of devices. The process further includes notifying the second device of the social content received from the first device. The social content includes the instruction to the second device to perform the action in association with the action timelines.

An embodiment herein provides a method for facilitating sequential, synchronous, and automatically coordinated operation of a plurality of devices through interactive elements involving a chain of tasks and devices. The method includes providing a social networking service by a social networking server to the plurality of devices so that each of the plurality of devices are communicatively connected to the social networking service by associating respective social profiles with the social networking server, wherein the respective social profiles are a social representation of the plurality of devices, and wherein the social networking server is programmed to allow the plurality of devices to coordinate for a synchronous social times-based functioning. The method further includes associating connection type social device relationships between a first device and a second device of the plurality of devices. The connection type social device relationships allow the first device and the second device to view a social profile of one another through a device user interface enabled by the social networking server. The method includes receiving social content from the first device. The social content is indicative of a social action performed by the first device and an instruction to the second device to perform an action in association with action timelines. The action timelines are indicative of time points associated with the action and define time when actual action should occur at the plurality of devices. The method further includes notifying the second device of the social content received from the first device, wherein the social content includes the instruction to the second device to perform the action in association with the action timelines.

An embodiment herein provides a system for health management of a plurality of devices interconnected through a social networking platform. The system includes a social networking server that provides a social networking-based health service to the plurality of devices and allows the plurality of devices to perform a series of social health tasks by exchange of social content in a socially aware network. The social networking server is programmed to create and manage individual centric profiles of the plurality of devices that are a social representation of individual devices within the socially aware network. The individual devices are identifiable by other devices and the social networking server through social profiles of the individual devices. The social profiles of each of the individual devices include a health profile indicative of health disciplines corresponding to each device and a specification profile including details corresponding to predefined working parameters of the each device. The social networking server is further programmed to associate device social relationships in the socially aware network. The social networking server is programmed to receive updates pertaining to a health profile and a specification profile of a device through a social activity involving social content exchange between a first device and the social networking server. The social networking server is further programmed to associate a relationship between the specification profile of the device and its health profile, wherein a mismatch between one or more parameters of the health profile and the specification profile represents a fault in the device. The social networking server is further programmed to identify a connection device to alternatively perform a function of a faulty device such that the connection device is in an idle state for a time period during which the connection device is required to alternatively perform the function.

An embodiment herein provides a method for health management of a device interconnected with a plurality of devices through a social networking platform. The method includes creating and managing individual centric profiles of the plurality of devices that comprise a social representation of individual devices within a socially aware network. The individual devices are identifiable by other devices and a social networking server through a social profile of each individual device. The social profile of each individual device includes a health profile indicative of health disciplines corresponding to a device and a specification profile including details corresponding to predefined working parameters of the device. The method further includes associating device social relationships in the socially aware network. The method further includes receiving updates pertaining to a health profile and a specification profile of a device through a social activity involving social content exchange between the first device and the server. The method further includes associating a relationship between the specification profile of the device and its health profile. A mismatch between one or more parameters of the health profile and the specification profile represents a fault in the device. The method includes identifying a connection device to alternatively perform a function of a faulty device such that the connection device is in an idle state for a time period during which the connection device is required to alternatively perform the function.

An embodiment herein provides a system for monitoring and conveying health related information from a first device to a second device interconnected through a socially aware network. The system includes a processing circuit coupled to the first device. The system includes a social event timeline recorder that stores information pertinent to when an event should occur at the first device, wherein the event should occur at a defined social time. The system includes a social event timeline monitoring unit that monitors an event occurrence time for the event. The system includes a fault detector that compares the social event timeline with the event occurrence time for the event, wherein a gap between the social event timeline and the event occurrence time beyond a threshold limit is indicative of a fault. The event at the first device and the event at the second device are interdependent. The system includes a communication circuit that allows sharing of a social content, indicative of the fault and a predicted modified event occurrence time at the first device, to a social networking server through a two-way communication channel including a near field communication channel and a socially aware network channel. The social networking server sends the social content to the second device. The first device and the second device include connections and parts of a same chain of integrated tasks.

An embodiment herein provides a method for monitoring and conveying health related information from a first device to a second device interconnected through a socially aware network. The method includes storing information related to defined social event timelines for tasks associated with the first device, wherein the defined social event timelines define times when an event should occur at the first device. The method includes monitoring a social event occurrence time by a social event timeline monitoring unit. The method includes detecting a fault in functioning of the first device by comparing the social event timeline with an event occurrence time for the event. A gap between the social event timeline and the event occurrence time beyond a threshold limit is indicative of the fault. The event at the first device and the event at the second device are interdependent. The method further includes sharing a social content, indicative of the fault and a predicted modified event occurrence time at the first device, to a social networking platform through a two-way communication channel including a near field communication channel and a socially aware network channel. The social networking platform sends the social content to the second device. The first device and the second device comprise connections and parts of a same chain of integrated tasks.

BRIEF DESCRIPTION OF THE DRAWINGS

The features of the disclosed embodiments may become apparent from the following detailed description taken in conjunction with the accompanying drawings showing illustrative embodiments herein, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

In the following detailed description, reference is made to the accompanying drawings which form a part hereof, and in which is shown by way of illustration specific embodiments in which the embodiments herein may be practiced. These embodiments, which are also referred to herein as "examples," are described in sufficient detail to enable those skilled in the art to practice the embodiments herein, and it is to be understood that the embodiments may be combined, or that other embodiments may be utilized and that structural, logical, and electrical changes may be made without departing from the scope of the embodiments herein.

Figure 1:
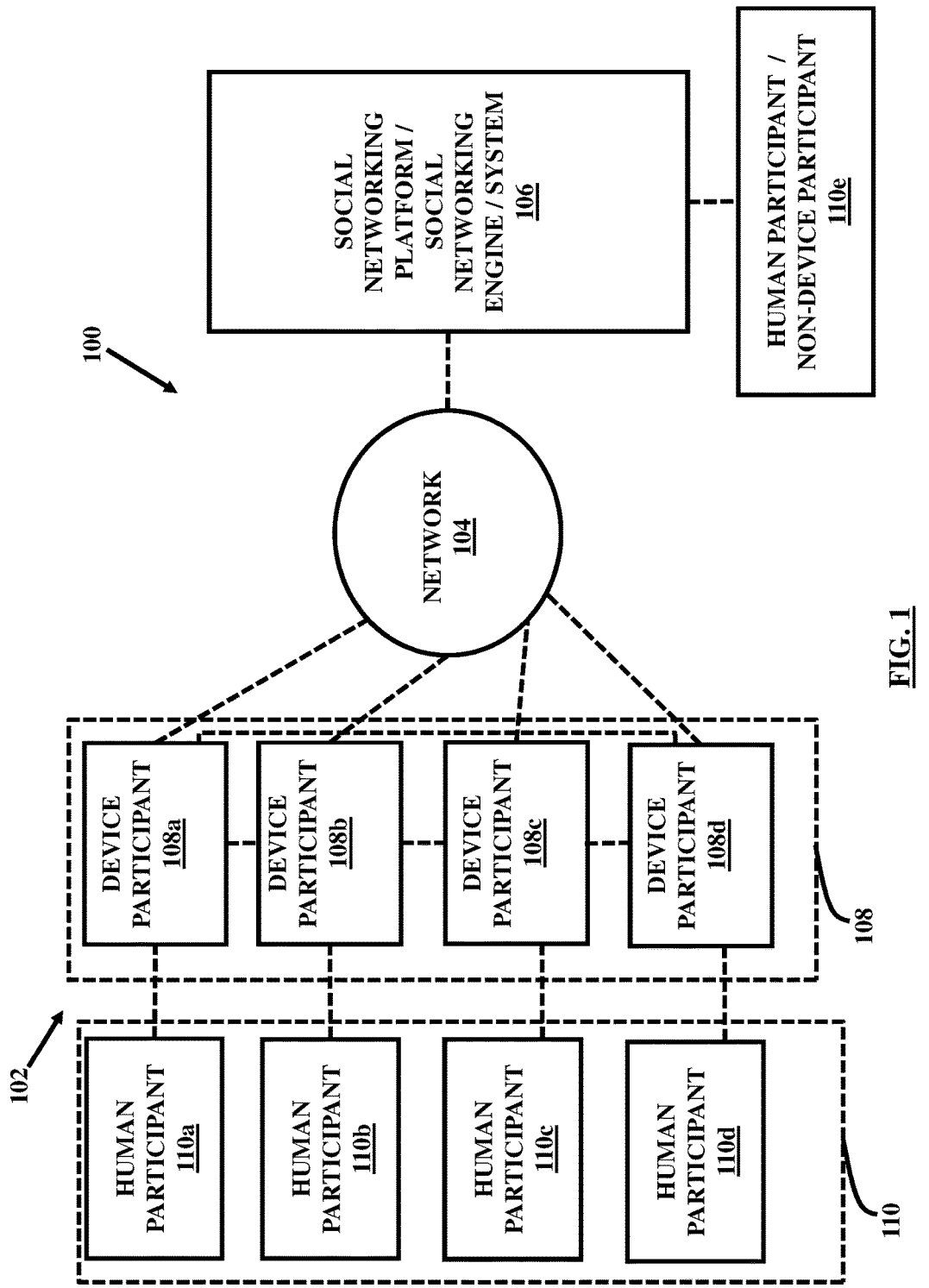
FIG. 1 illustrates an exemplary ecosystem of participants interconnected over a socially aware network through a social networking platform, in an embodiment of an embodiment herein.

FIG. 1 illustrates an exemplary ecosystem 100 of participants 102 interconnected over a socially aware network 104 through a social networking platform 106 also referred to as social networking engine 106 interchangeably without limitations. As shown in FIG. 1, the ecosystem 100 provides the social networking platform 106 for device participants 108. One or more such devices or device participants such as a device 108a, a device 108b, a device 108c, and a device 102d are in communication with the social networking platform (SNP) 106 through the network 104 to provide a socially aware networking facility for the devices 108.

In accordance with some embodiments, the devices 108 are autonomous and may not require human intervention. The devices 108 can directly exchange social content on their own without any human intervention.

However, in accordance with an embodiment, as shown in FIG. 1, the devices may not be fully autonomous and may require human intervention for certain activities. In accordance with this embodiment, each device 108 is associated with a non-device or human participant 110. As shown, the ecosystem 100 in an exemplary embodiment includes multiple device participants 108 and multiple non-device participants 108 each associated with a device participant 108. For example, the device participant 108a is associated with a non-device participant 110a, device participant 108b is associated with a non-device participant 110b, the device participant 108c is associated with a non-device participant 110c, and the device participant 108d is associated with a non-device participant 110d.

In some embodiments, a non-device participant such as 110e may be added to the network 104 without it being associated with any of the device participants 108. For example, a physician who is not associated with any specific device as a coordinator may be associated with the social networking platform 106 and may, for example, function as a consultant or expert. Similarly, several other non-device participants may also join the network for social activity or social content exchange within the network 104 without any association with a specific device. In embodiment, the non-device participants 110 are human participants.

In an embodiment, the device participants 108 can be automated devices, or non-automated devices. In an embodiment, the devices 108 may not have computational capabilities and may not be able to directly communicate to a network 104 as a mobile phone, desktop, tablet, personal computer, cell phone, smart phone etc. can do. For example, such types of devices 108 can be medical devices in a healthcare environment that may not have or may partially have computation capabilities and may not be directly able to communicate to the network 104 for information exchange. A few examples of such devices 108 without limitations are thermometers, blood sugar meters, medical robots, microchip implants, prosthetic devices, pacemakers, defibrillators, magnetic resonance imaging machines, ultra sound machines, physiologic monitors, vital sign monitors, electrocardiographs, infusion pumps, ventilators, cardiac output monitors, infant incubators, blood gas analyzers, extracorporeal therapy systems, diagnostic systems, radiologic and fluoroscopic systems, mammography systems, intra-aortic balloon pumps, anesthesia units, dialysis units, partially intelligent medical devices hubs, sensors or other sensor-based devices, other non-intelligent or partially intelligent medical devices, and others without limitations.

In an embodiment, the devices 108 can be sensors that are capable of sensing an environment. In some embodiments, the devices 108 may not independently perform processing and computation tasks and may be able to be networked so as to enable them to perform processing and computations tasks by linking them with processing circuits and computational units. It must be appreciated that though a primary device may not be capable of computation, it can invite smart and intelligent devices to join the network 104 so that the secondary devices can then join the network 104 and may function as a social network participant 102. Therefore, the ecosystem 100 facilitates interaction between intelligent as well as non-intelligent devices and non-device participants 110; however, the ecosystem 100 includes at least one device participant that is potentially incapable of computations.

In an embodiment, the social networking platform 106 provides a facility for automation in devices networking and interconnection. In an embodiment, the devices having no computation capabilities and can also be integrated and interconnected socially through the social aware network 104 by the social networking platform 106.

In an embodiment, the social networking platform 106 allows the devices 108 to voluntarily join the social network 104, disassociate or leave from the social network 104, extend interconnection with other like-minded devices, send invitations for connections to other devices, accept or reject invitations from other devices, view profiles of connections or other devices, exchange social activity information, establish social signatures for social authorization of profiles, create devices groups, join devices groups, leave devices groups voluntarily or involuntarily upon a request by other devices, and perform various other tasks meant to be performed in a socially aware cluster of entities.

Figure 2:
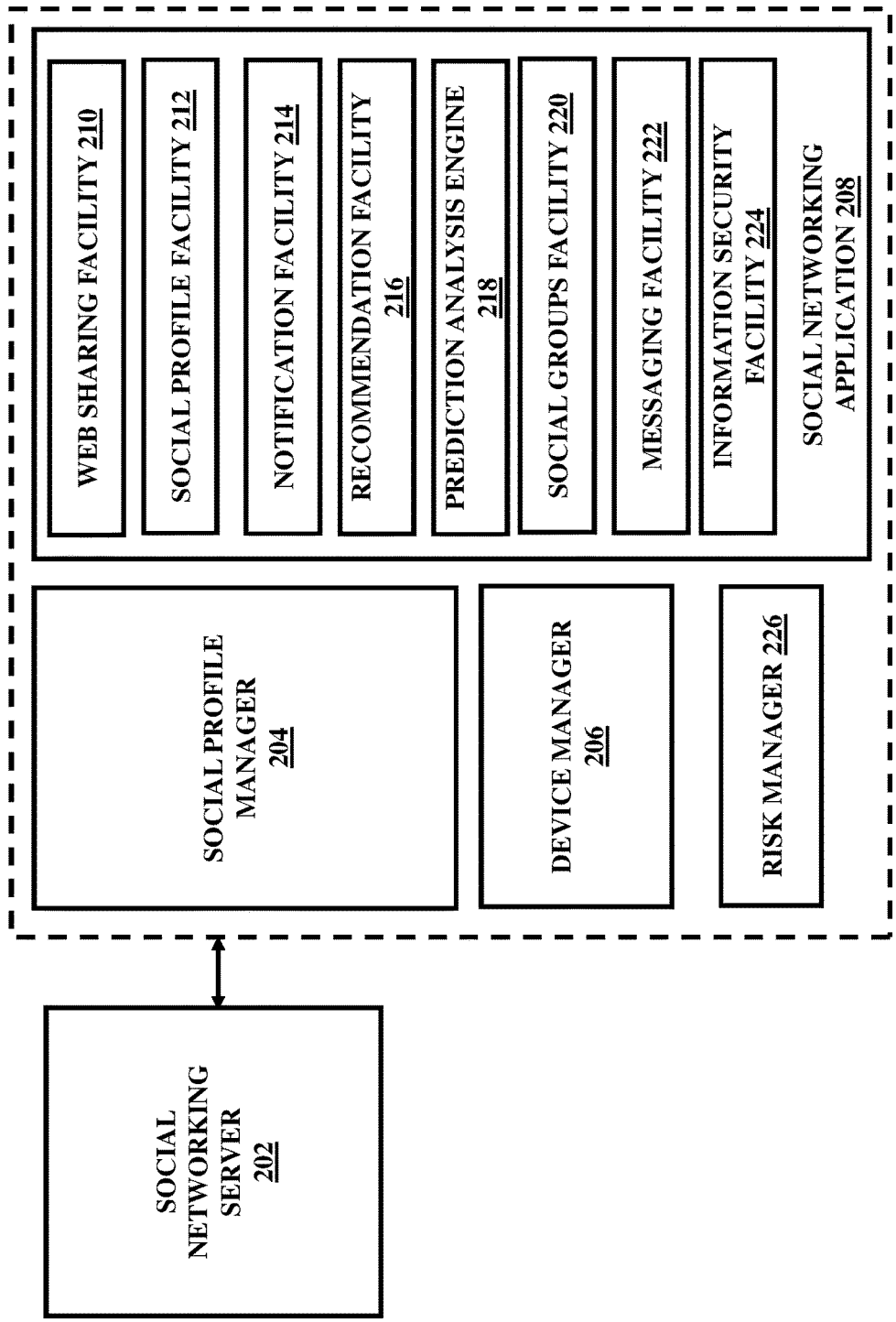
FIG. 2 illustrates a social networking server for implementing a social networking platform in accordance with an embodiment herein.

FIG. 2, with reference to FIG. 1, illustrates a social networking server 202 for implementing the social networking platform 106 in accordance with an embodiment. The social networking platform 106 (also referred to as a social networking engine or a system) may provide a social networking service to the plurality of participants 102 and allow them to perform a series of social tasks in the socially aware network 104. The social networking server 202 facilitates social information exchange among the participants 102 through the socially aware network 104. As discussed above in conjunction with FIG. 1, the plurality of participants 102 may include device participants 108 as well as non-device participants 110.

The server 202 is communicatively coupled to a social profiles manager 204 for creating and managing individual centric profiles of the participants 102 that are social representation of the individual participants 102 within the socially aware network 104. The participants 102 are identifiable by other participants and the social networking server 202 through their social profiles. The device participants 108 may be associated with device social profiles and the associated non-device participants 110 may be associated with human social profiles or non-device profiles. The human profiles or non-device profiles are associated with one or more device profiles. In some embodiments, the social human profiles are represented as subsets of the corresponding device social profiles.

Figure 3:
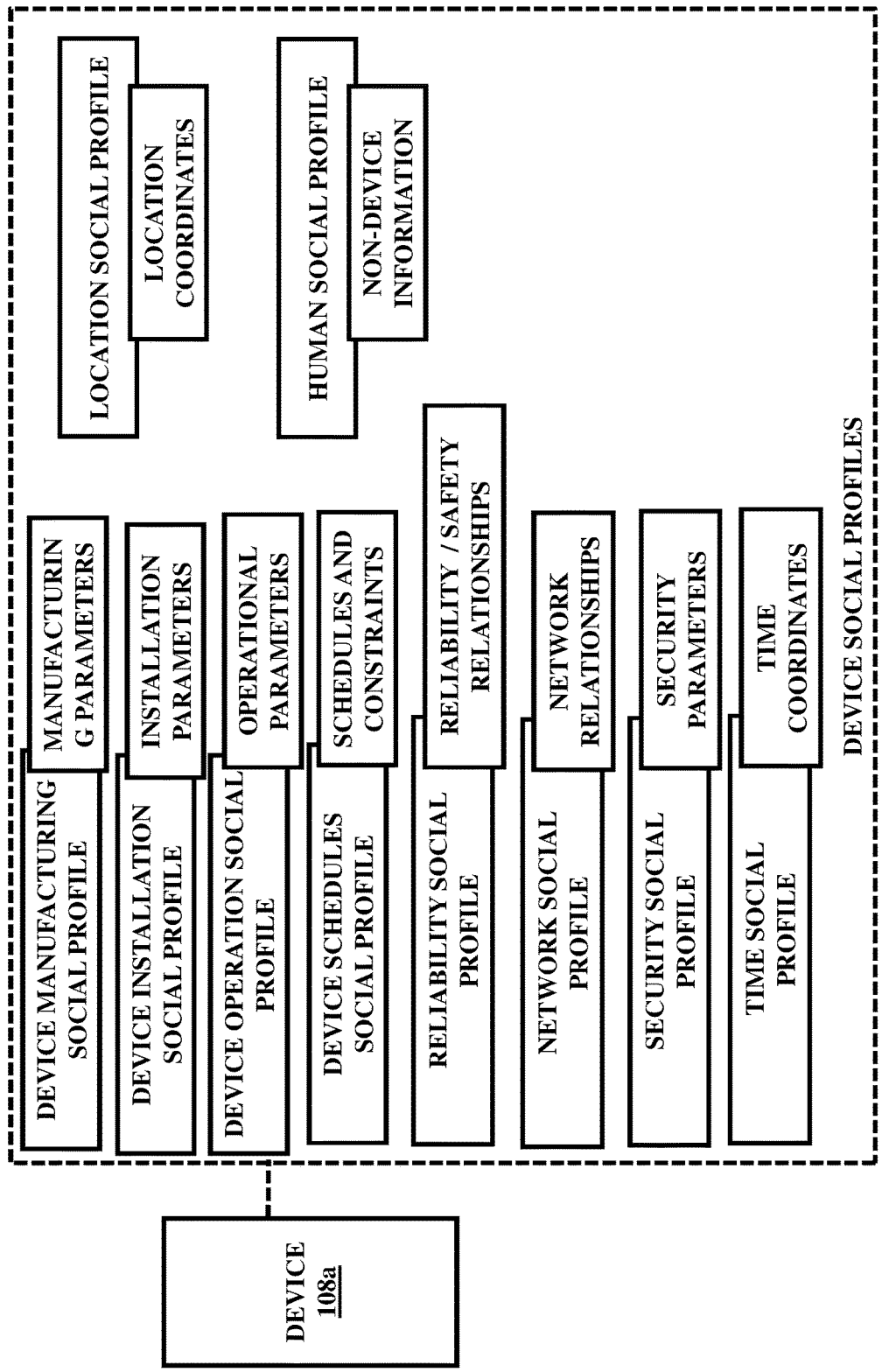
FIG. 3 illustrates an exemplary embodiment of social profiles of devices and non-device participants in an embodiment herein.

FIG. 3, with reference to FIGS. 1 and 2, illustrates an exemplary embodiment of social profiles of the devices 108 and non-device participants 110 that is human profiles. In some embodiments, two types of profiles may be created including a device social profile and a human social profile. The human profile may in some cases, where a human is associated as a coordinator of a device 108a, be associated with a device profile so that the human social profile is a subset of the device social profile. The device social profile may include a manufacturing profile, an installation profile, an operation profile, a schedules profile, a location profile, a reliability profile, a network profile, a security profile, and a human profile. The various profile types are discussed hereafter.

The manufacturing profile associated with a device 108a includes information pertaining to manufacturing, design and fabrication parameters of the device 108a. This may include information such as material of the device 108a, composition of the device 108a, shape, size, dimensions, fabrication process, manufacturing limitations, manufacturing defects, fabrication limitations, component names, component design, components connections, design constraints, strength, factor of safety, manufacturing date, and other details relevant to the manufacturing aspects of the device 108a.

The installation profile may include details such as relevant for installation of the device 108a, for example installation location, installing warranty, installation company, installation guidelines, device's association with other proximity devices, installation configurations, installation settings, electronic, electrical, or mechanical connections among the installed components, safety precautions regarding installation such as installation requirements, and the like.

The operation profile may include details relevant for post installation activities of the device 108a such as its operation, functioning, coordination with other devices, routine activities of the device 108a and so on. The operation profile may include details such as usage guidelines for example one time usable, twice usable etc., running time, operating parameters, operating capabilities, operating limitations, real-time operating details, historical usage, fault histories, operational faults, operating status, operating costs, battery usage, battery availability, and the like.

The location profile includes details pertaining to location characteristics and coordinates of a device such as 108a for example details such as where the device 108a is located, location coordinates with respect to proximate devices, and location coordinates of the proximate devices and the like.

The reliability profile includes details pertaining to reliability and safety relationships and characteristics of a device such as device 108a. The reliability relationships may associate reliability standards of the device 108a with a purpose of use of the device 108a. For example, the device 108a may be highly reliable or safe for one time use but may not be reliable or safe for another purpose. In an embodiment, reliability and safety relationships may associate a device reliability standard with a network type. For example, a high reliability highly safe device only may be allowed in one network while even a low or medium reliability device may be allowed in another network. In several embodiments, the term reliability and safety relationships may define safety critical, or life critical, or other such parameters.

The network profile includes details pertaining to network-based characteristics or relationships of a device such as the device 108a. The network-based relationships may include information such as network type, network coverage, and the like. The network profile may allow accommodating device relationships but only if the device 108a observes a defined network-based communication such as through a wired vs. wireless network (which may be indicative of security or reliability). For example, a social network of the devices 108 may allow some devices to become a part of the network in cases where traffic is going over a wired network or secure satellite but not Wi-Fi or through any other defined network.

The time profile of a device such as the device 108a includes details pertaining to time coordinates of an action or a task performed by the device 108a. For example, the time profile may include details such as when a device 108a is in operating state and when is in idle state, when in future the device 108a may be idle or functioning.

The security profile includes details pertaining to security characteristics of a device 108a. The security information or details in a security profile may include security standards of the device 108a such as how secured the device 108a is. A device such as the device 108a may, for example, be categorized as a low security device or a high security device and the like. The security profile may allow security-based relationships with other devices by associating security relationships in association with a device purpose or function. For example, the security-based relationships may accommodate how secure a device 108a is for a given purpose. The security profile defines parameters and relationships such as about protecting device data, and about device privacy etc.

The risk social profile of a device 108a may include individual device risk information that is indicative of how risky a device, such as 108a, is for a defined operation and in a defined setting or environment. For example, a recording device in a medical environment may be considered as a low risky device and a corresponding risk social profile may include the low risk details. A diagnostic device may be considered as a low to medium risk device and a corresponding risk social profile may include the low to medium risk details of the device. A therapeutic device to deliver drugs etc. to a patient may be a high risk device and corresponding social risk profile may include the high risk details of the device. In an embodiment, the risk profile information may be identified and reviewed by the devices 108 so as to identify nature of association with regards to risk prior to accepting a device invitation as a connection. For example, a ventilator associated with a patient may be a high risk device and may not want to connect with a low risk device for patient safety purposes and therefore may analyze social risk profiles of the devices that send connection invitations to the ventilator or to which the ventilator sends connection requests.

In an example, the individual risk social profiles that may be predefined by the devices 108 or their coordinator or non-device participants 110 may behave differently than an aggregated social risk profile of a group containing the individual social risk profiles. For example, in an embodiment, the four devices 108 as shown in FIG. 1 may be associated with different risks as identified through their social profiles. However, the aggregated risk of each device in the group containing the four devices 108a-108d after interconnection is same. This means that the risk of all the four devices 108a-108d is now changed and is same for all the devices. In an example, the aggregated risk may be the risk of the highest risky device among the four devices 108a-108d. In an example, the aggregated risk may be calculated based on computational techniques, mathematical and analytical models, and software algorithms etc.

In some embodiments, a device such as the device 108a may be associated with a non-device participant such as the non-device participant 110a such as a human participant who may coordinate or control one or more functions of the device 108a. For example, the non-device participant 110a may stop or start the device 108a. In an embodiment, the non-device participant 110a may be an initiator of the device 108a or task or a consumer of the device 108a or an output associated with a task or device 108a. The non-device participant 110a may be associated with a human social profile so that the human social profile may be a sub-profile of the device social profile. The human social profile may include details pertaining to the coordinator of the device 108a such as age, sex, qualification, expertise, credentialing, affiliation, and other details related to the person or the non-device participant 110a associated with the device 108a.

Therefore, as discussed above, in accordance with various embodiments, the device profile may include the manufacturing profile, installation profile, operation profile, network profile, security profile, reliability profile, location profile, time profile, and a human social profile such that a first set of activities are performed by the device 108a and a second set of activities are performed by the associated non-device participant 110a, wherein the non-device participant 110a is identified by the device profile.

In some embodiments, a human social profile may control and govern other profiles of the device 108a. For example, a person defined as a coordinator of the device 108a may be provided privileges to modify one or more profiles of the device 108a.

In some embodiments, the social networking server 202 is programmed for a multi-level profile based identification that is indicative of a device such as 108a uniquely by other devices in the social networking ecosystem 100. The multi-level profile-based unique identification of the devices 108 includes identification of the devices profiles including at least one non-device profile that may be allowed to modify other profiles of the devices 108. The multi-level profile based identification of the devices 108 in the network 104 facilitates sequential control and monitoring of a chain of tasks and interconnected devices performing the tasks by allowing the devices 108 to initiate or respond to a social activity for social interaction among the devices and non-device participants 108 and 110 based on target network connection identification and directing the social activity-based messages accordingly to the uniquely identified target connection participants.

In an embodiment, a human participant such as 110e may be allowed to join the social networking platform 106 upon a request by a device such as 108a or a non-device participant 110a associated with the device 108a. In accordance with some embodiments, therefore, the social networking platform 106 may allow the devices 108, associated non-devices 110 and other humans such as 110e not associated with a device to join the social networking platform 106 and execute social activities through the socially aware network 104. However, in some embodiments, it must be appreciated that the social network 104 includes at least two devices so as to allow devices-based interaction either directly among the devices or through an activity initiated by a an associated non-device or any third party non-device.

Referring back to FIG. 2, the social profiles manager 204 facilitates creating and managing individual centric profiles of the participants 102 that are social representation of the individual participants 102 within the socially aware network 104. In some embodiments, the profile manager 204 first allows creation of a base profile so that the base profile further allows creation of secondary profiles. The base profile may be a social human profile for a non-device participant such as human participant 110a associated with a device such as device participant 108a. The secondary profiles may be created subsequently based on a set of parameters identified by the social human profile. For example, once a human profile is created for the device 108a, the device 108a may be constrained to be installed, operated, and managed by the non-device participant 110a in a way that fulfills the requirements identified by the social human profile of the device 108a. The profile manager 204 provides a social interface to facilitate the non-device participant such as 110a to interact with the device 108a for creating the base profile and the secondary profiles. The profile manager 204 may link the various sub-profiles of the device 108a so that each of the sub-profiles such as the operation or installation or any other sub-profile may be tied to a respective human social profile so that the device is identifiable by other devices through device specific or human profiles associated with the device profiles. The profile manager 204 is further discussed hereafter.

The server 202 further includes or is further communicatively coupled to a device or participants manager 206 to manage participants' relationships and social activity in the socially aware network 104. The device manager 206 may enable social settings for allowing the devices 108 or associated non-device participants 110 to interact over the social network 104. For example, the device manager 206 may allow new devices to join the network by enabling network join settings of the devices 108. In some embodiments, the device manager 206 may manage devices' social activation and deactivation that enables or disables the devices 108 from doing social activity or communicating through social content exchange. The device manager 206 may further support device profiles enablement so that the device manager 206 may allow visibility of the various social profiles of the devices 108 based on social context or type of exchange among the devices 108. In some embodiments, the device manager 206 may associate one or more social profiles of a device such as 108*a* with the device 108*a* so that the device 108*a* is identifiable by other devices or non-devices. In some embodiments, the device manager 206 may be authorized to hide certain device profiles based on other socially active device contexts. For example, the device manager 206 may not allow visibility of a human social profile to a connection device and thus may hide the human social profile. In some embodiments, the device manager 206 may allow interaction of the devices 108 with the social networking server 202. The device manager 206 may further allow communicating through various network channels such as a multi-level networking channel mechanism as will be discussed later. In some embodiments, the device manager 206 may control device social settings. In some embodiments, the device manager 206 may control non-social settings such as including device operating characteristics so that the device manager 206 may include social platform and an operating platform wherein the operating platform controls non-social settings and the social platform controls social settings. In some embodiments, the social settings may be dependent on operating characteristics and vice versa. For example, the social platform of the device manager 206 may communicate social content when a social activity is triggered with a connection device upon identification of a status change in the device operating characteristics. For example, an operating platform of a heart beat monitor may receive operating information pertinent to an abnormal heart rhythm and notify the social platform of the device 108*a* to execute a social activity initiated by the device 108*a* with a connection ventilator so as to initiate artificial ventilation by the connection ventilator. The social and the operating platforms may be interdependent and enabled to coordinate with the social networking server 202 such that the device settings may be communicated to the network server 202.

The server further includes a social networking application 208 that includes a cluster of social applications each for providing a specific social facility to facilitate social activity among the device participants 108 through the socially aware network 104.

In some embodiments, the social networking application 208 may include a web-sharing facility 210 for allowing information exchange among the participants 102 through a web-based interface. In some embodiments, the social networking application 208 may include a social profiles facility 212 for allowing the participants 102 to create respective social profiles. In some embodiments, the social application 208 may include a notification facility 214 for facilitating exchange of invitation notifications for extending a participant's social space. In some embodiments, the social networking application 208 may include a recommendation facility 216 for sharing recommendations for a device such as 108*a* based on noticed past behavior of the device 108*a* by a connection device. In some embodiments, the social networking application 208 may include a prediction analytics engine 218 for determining participants future behavior based on historical social data about the participants 102. The prediction analytics engine generates information about what a device such as 108*a* can do and how it can behave in future. In some embodiments, the social application 208 may include a social groups facility 220 for creating a social group dedicated for the participants 102 and exhibiting a defined behavior or belonging to a defined class. In some embodiments, the social application 208 may include a messaging facility 222 for sharing social content from a participant to another connection participant. In various embodiments, the messages can be either instant messages, or emails or other types of messages. In some embodiments, the social networking application 208 may include an information security facility 224 for encrypting and decrypting social content during exchange among the participants 102.

In an example, the device manager 206 may include or may be coupled to a risk manager 226 for computing the aggregated risk based on the individual risks of the individual devices such as the devices 108. In an example, the risk manager 226 may further analyze and predict risk patterns in association with device contexts or environments or device groups. The risk manager 226 is adapted to retrieve the social profile information corresponding to the individual devices 108 to determine a risk profile of the entire group and identify risk patterns of the entire group. The risk profile and risk patterns are indicative of how safe and reliable it is for a device to join the group for social information exchange or social activity or in a particular network or environment for operation. The risk manager 226 may provide safety interlocks, risk management capability, and risk documentation capability. The risk documentation capability may provide a facility for the devices 108 to update their social risk profiles based on their networking and interconnection with a group of devices having different risks. The risk documentation may be performed in the social profiles so that the updated risk may be indicated and contained within the social profiles of the devices.

Figure 4:
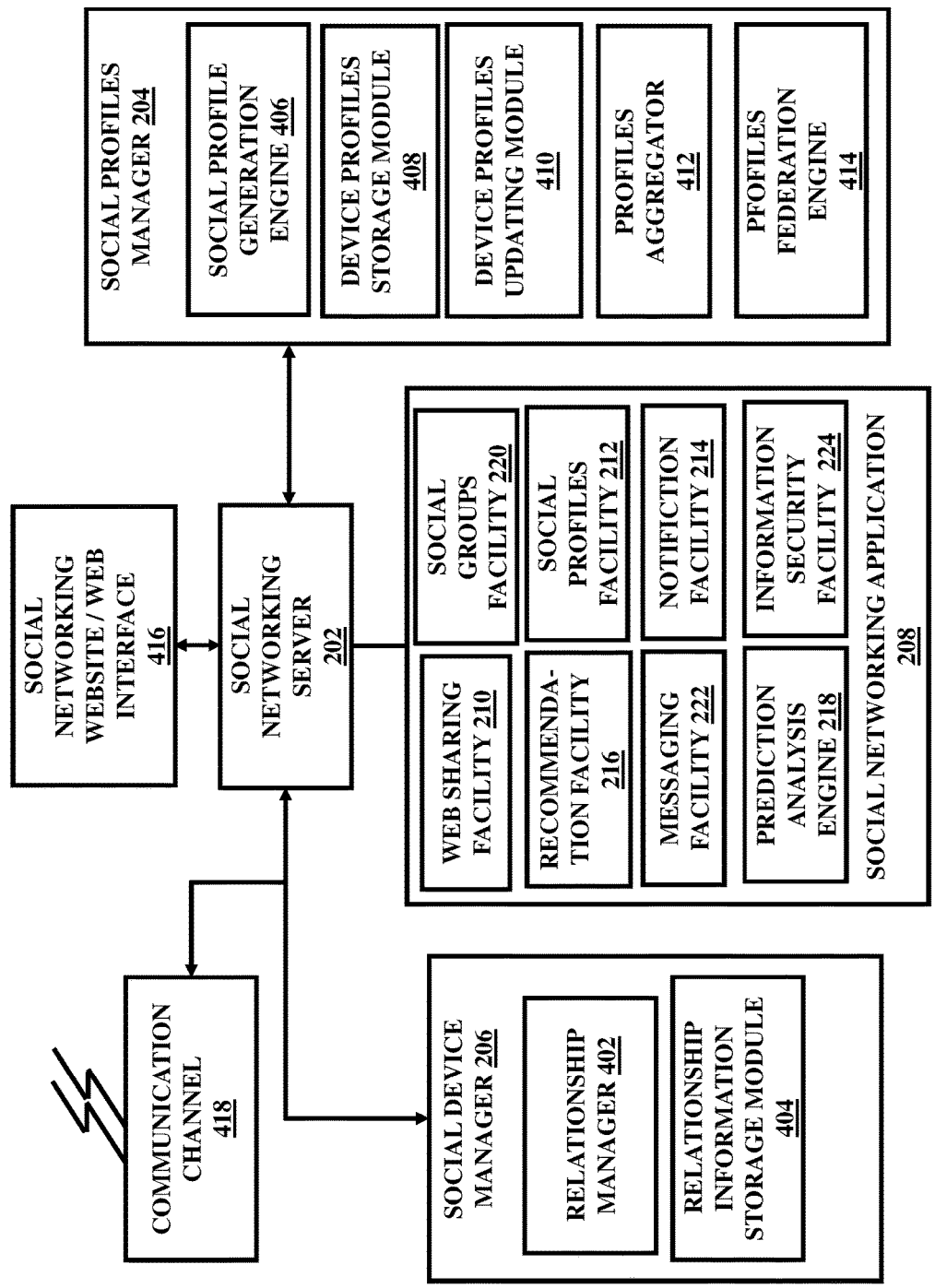
FIG. 4 illustrates a social networking server among other things in an embodiment herein.

FIG. 4, with reference to FIGS. 1 through 3, illustrates the server 202 among other things according to an embodiment herein. As shown, the social device manager 206 includes a relationships manager 402 and a relationships information storage module 404. The relationships manager 402 manages and/or updates social relationships among the devices 108. The relationships may be associated with the social profiles of the devices 108 interacting with one another. In some embodiments, the devices 108 may coordinate through different relationship patterns that the relationships manager 402 may govern. For example, the relationships manager 402 may manage manufacturing relationships, installation relationships, operation relationships, security relationships, reliability relationships, network relationships, time relationships, location relationships and the like. The relationships manager 402 may organize the different relationships among the interacting devices 108 in a device oriented pattern based on device oriented social profiles so that one type of device relationship gets a higher priority over another type of relationship. The relationships manager 402 resolves relationship conflicts among the devices 108 based on the relationships priorities. The device conflicts may arise in case of conflicting situations such as when one device enables a function that requires a social contribution from a second device but the second device denies contributing through the social activity. The relationships manager 402 assesses the social profiles-based relationships between the devices 108 and decides about the devices' behavior during social interactions. For example, if the relationships manager 402 identifies that an operation relationship between the devices 108 necessitates coordinated functioning; the relationships manager 402 facilitates the devices 108 to issue instructions through the social activity to facilitate interaction by the devices 108. However, if the security relationship warrants the security through the devices' integrated functioning, the relationships manager 402 may facilitate the devices 108 to issue an instruction based on higher priority of security relationship than the operating relationship to stop the interaction between the devices 108 either automatically or through an intervention by a non-device participant such as 110*a*.

In some embodiments, each of the social profiles associated with a device such as 108*a* may define a social relationship so that two or more interacting devices are associated with a layered social relationship including a plurality of social profile dependent relationships with each relationship associated with a priority setting indicative of criticality of nature of relationship over other relationships.

A device such as the device 108*a* can maintain specific and defined relationships with other devices. The relationships may comprise any type of relationship that may exist between such as two of the devices. For example, the device 108*a* and the device 108*b* may be like-minded, for example, both may be medical devices or more specifically both may be pacemakers from the same make, the devices 108*a* and 108*b* may have similar profiles, the devices 108*a* and 108*b* may be parts of a single operational/procedural sequence, the devices 108*a* and 108*b* may be used by the same person such as a patient as identified by a patient identifier associated with the devices 108*a* and 108*b*.

In embodiments, the relationship manager 402 can track or monitor the relationships among the devices 108. The relationship manager 402 can maintain the information regarding relationships in the form of a social map, in some embodiments. The social map is discussed later in detail.

The information pertaining to the relationships among the devices 108 networked through the social networking server 202 is stored in the relationships information storage module 404. In an embodiment, the social relationships map can be stored in the relationships information storage module 404. The relationships information storage module 404 stores information pertaining to the social profiles in association with the social relationships and the priority settings associated with each relationship. The relationships information storage module 404 may for example store information pertaining to the manufacturing relationships, installation relationships, operation relationships, security relationships, reliability relationships, network relationships, time relationships, location relationships and the like.

The relationships information storage module 404 may include a memory circuit configured to store the information related to the devices relationships as discussed above.

The server 202 may further be coupled to or may include the social profiles manager 204 for creating and managing individual centric profiles of the participants 102 that are social representation of the individual participants within the socially aware network 104. The participants 102 are identifiable by other participants and the social networking server 202 through their social profiles. The social profiles manager 204 includes a profile generation engine 406, a profile storage module 408, a profile updating module 410, a profile aggregator 412, and a profiles federation engine 414.

The profiles generation engine 406 facilitates creation of the social profiles of the devices 108. The profiles generation engine 406 provides an interface for allowing a non-device participant such as 110*a* to join a device 108*a* with the social networking platform 106 by providing relevant necessary details related to the device 108*a* and the non-device participant 110*a* so as to initiate a social subscription through the social networking platform 106 for the devices 108. The profile generation process may require the non-device participant 110*a* to provide at least minimum details necessary for the social profile subscription with the social networking platform 106. In some embodiments, the profile generation engine 406 necessitates the creation of human social profile by the non-device participant 110*a* associated with the device 108*a* and the remaining device profiles are automatically generated by uploading device manuals and documents with the networking server 202. In various embodiments, the social profiles generation engine 406 may include sub modules for generating specific device profiles associated with the device 108*a*. For example, a manufacturing profile component may provide an interface for creating a manufacturing profile of the device 108*a* including manufacturing parameters associated with the device 108*a*. An installation profile component may provide an interface for creating an installation profile of the device 108*a* including installation parameters. An operation profile component may provide an interface for generating an operation profile of the device 108*a*. A reliability profile component may provide an interface for generating a reliability profile of the device 108*a*. A security profile component may provide an interface for creating a security profile of the device 108*a*. A network profile component of the device 108*a* may provide an interface for creating a network profile of the device. A human social profile component may provide an interface for generating a social profile of the non-device participant 110*a* associated with the device 108*a*. In an embodiment, the social human profile component initiates the other profiles components such that when the human social profile is generated, the other profiles components are automatically initiated so as to interact with a device and/or the non-device participant for generating other device centric profiles by retrieving device related details.

In an embodiment, various types of device profiles may be created for each of the devices 108 that may want to be a part of the social networking architecture or SNP 106. For example, the device 108*a* may want to access the social networking service or platform 106 and a device profile is needed prior to joining the social networking platform 106. The device profiles may include details such as device name, device characteristics, features and qualities, device operation and functioning, device capabilities, device architecture and components, relevant dates such as device purchase date and device expiry date, device association map with other devices, device location and so on. In some embodiments, more than one profile may be created for a single device which can be such as associated with one another. In an embodiment, the information pertaining to the device 108*a* such as manufacturing related information, installation related information, and the operation related information may be automatically stored in a memory contained within the device 108*a*. Alternatively, in some embodiments, the storage of the relevant device information may be performed manually by a user or an operator.

As soon as the device 102*a* creates the profile, it becomes a member of the SNP 106. The device 108*a* can now enjoy various facilities provided by the SNP 106, for example, coordination with other networked devices 108, connecting with other devices 108, and sharing information with other networked devices 108 and so on. The device 108*a* can view permitted data about other social network members or devices 108, enter data about themselves and possibly others, join social network groups, and so forth. The devices 108 are typically members of the social networking platform 106.

In accordance with an embodiment, a device such as 108*a* may inform another device such as 108*b* or may publish data such that the other device 108*b* can handle the data asynchronously for such purposes as information capture, analytics, or any other behavior defined by the device 108*b*. In an embodiment, the device 108a may inform another device 108b directly and synchronously for such purposes as information capture or analytics or other behavior defined by the device 108b. In an embodiment, the device 108a may be aware of the functionality of the device 108b such that the device 108a may influence behavior of the device 108b asynchronously. For example, an insulin pump can influence a heart rate monitor to initiate data tracking during the insulin injection. In another embodiment, the device 108a may be aware of functionality of the device 108b and may control behavior of the device 108b synchronously. The pump can inform or communicate to all the devices 108 integrated through the SNP 106 or to its connections that might be running and associated with a patient at that time to pause during injections.

In an embodiment, the profile generation engine 406 may employ multi-profile architecture for creating device specific multiple social profiles as shown and discussed later in conjunction with FIG. 5. The multi-profile architecture comprises a profile application component 502, a device personalization component 504, and a presentation component 506. The multi-profile architecture is discussed further hereafter.

Referring back to FIG. 4, the social profiles manager further includes a device profiles storage module for storing profiles related information of the devices 108. The profiles storage module 408 may include or be coupled to a memory circuit capable of storing data. The social profiles manager 204 further includes a device profiles updating module 410 for making real time updates in the social profiles of the devices 108 with updates in device centric information due to device or component replacements, re-installments, device operations, security changes, reliability changes, location changes, time gaps, network changes, and changes in non-device parameters, and the like.

The social profiles manager 204 further includes a profiles aggregator 412 for aggregating multiple profiles so that the aggregated profile for multiple profiles serves as a single unified identity for a device such as 108a. The unified or aggregated profile can however be federated into distinct component profiles by a federation engine 414 upon a request by a viewer in the social network 104 for example for assessing a device 108a prior to joining the device 108a as a connection. For example, a device such as 108a may assess for like-mindedness in terms of operation parameters prior to joining a device 108b by viewing operation profile.

The server 202 may further be programmed to facilitate the devices 108 or non-device participants 110 by providing a web interface or a social networking website 416 for facilitating remotely located participants 102 to access social profiles of the devices 102 and interact with the devices 102 by exchange of social content through the social interface 416. In some embodiments, the web interface 416 may be utilized by a processing unit (not shown in FIG. 4) for accessing a remotely located patient associated device so as to access data from the device through the social network 104 and monitor patient's vital parameters and accordingly control device's operations remotely.

The server 202 may be communicatively coupled to a communication channel 418 that links the server 202 with the socially aware network 104 for exchange of social content among the devices 108 and non-devices participants 110. The communication channel 418 may include near field and wide area network as will be discussed hereafter.

Figure 5:
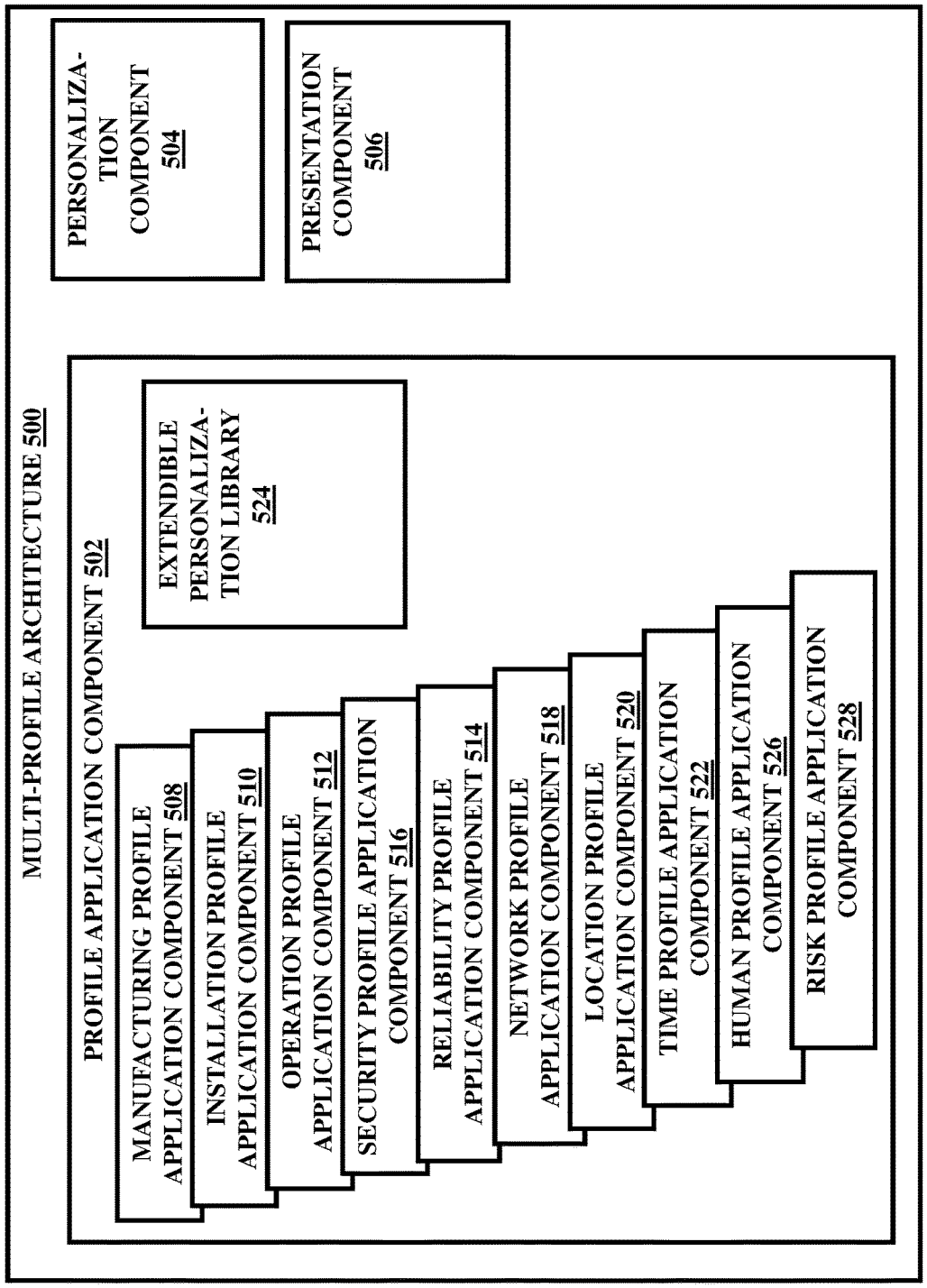
FIG. 5 illustrates a multi-profile architecture for creating device specific multiple social profiles in accordance with an embodiment herein.

FIG. 5, with reference to FIGS. 1 through 4, illustrates a multi-profile architecture 500 for creating device centric multiple social profiles by the social profile generation engine 406. The multi-profile architecture 500 comprises a profile application component 502, a device personalization component 504, and a presentation component 506.

The application component 502 includes sub-components each for one specific type of profile for a device such as 108a. As shown, the application component 502 may comprise a manufacturing profile component 508, an installation profile component 510, an operation profile component 512, a reliability profile component 514, a security profile component 516, a network profile component 518, a location profile component 520, and a time profile component 522, a risk profile component 528 and a human profile application component 526.

In some embodiments, the risk application component 528 creates a separate aggregated social risk profile for use by the devices 108 in the network 104 to identify risks associated with the grouped devices and accordingly makes connection decisions for extending social networking space and for social content exchange in the network 104. In an embodiment, the risk application component 528 of the server 202 may create or update the risk social profile based on computed aggregated risks. In an embodiment, the risk application component 528 of the server 202 may create or update the risk social profile based on devices behavior in the network 104 as identified through social content exchange and social activity with connection devices over time.

The application component 502 comprises an extendible network of libraries or extendible personalization library 524 wherein the libraries 524 include a set of templates each for creating a specific type of social profile associated with a device such as 108a. The template may include tables, columns, text blocks, image blocks, audio and video blocks etc. for allowing insertion or submission of social information of the device 108a by a non-device participant such as 110a to create a device profile. The social information may contain images, audio clips, video clips, texts, numeric, and the like. With the use of the templates, a participant may create several profiles of the device 108a in a standard form acceptable by the network 104.

The personalization component 504 allows personal and customized restructuring of the templates for defining device oriented or device required profile structure. For example, a pacemaker may require specific rearrangement in the way its profile is created so as to include cardiac rhythm parameters. The personalization component 504 facilitates the restructuring of the profile by implementing certain modifications using a set of keywords, and technical libraries included in the personalization component 504. The set of keywords and technical libraries may provide a participant to personalize profiles of the device 108a using the keywords and libraries such that the personalized profiles depict device characteristics, behavior and nature uniquely.

The presentation component 506 comprises an extendible network of application programming interfaces (APIs) for facilitating presentation of the personalized device centric profiles through a social interface such as 416. The presentation component 506 may further include template components for allowing selection of a defined display template of the social profile. The application component 502, personalization component 504, and the presentation component 506 may be communicatively coupled to the social networking server 202 for association of the social profiles with the devices 108 and enabling social activity identified by the associated devices social profiles.

In an exemplary embodiment, a social profile of an infusion pump may be generated by the multi-profile architecture 500 of the profile generation engine 406 employing personalization of infusion pump parameters. In an example, an infusion pump is tied to a patient for injection and delivery of drugs. The injection pump is networked with the social networking server 202 by an associated non-device participant such as 110a or any other coordinator. The process of networking of the infusion pump with the socially aware network 104 and server 202 is initiated after the non-device participant 110a initiates a social profile generation process by using the multi profile architecture 500 of the profile generation engine 406. The profile generation engine 406 presents a social subscription interface for the associated person or initiator to provide device specific details through several profile specific components. With the use of the personalization component 504, the initiator is able to provide particular details that are specific to the infusion pump. The presentation engine 506 facilitates display of the federated social profile of the infusion pump which is viewable by other devices 108 or non-device participants 110 in the network 104.

In embodiments, the social profiles of the devices 108 may include information pertaining to without limitations device name, device architecture, expiry date, performance standards, device features, components and sub-components details of the devices, association map, failure rate, devices' operations and functional capabilities, purchase date, location, reliability and security data, materials and compositions, quality standards, operational characteristics, social feedback from other participants such as devices 108 and non-devices 110, social tasks timings and the like.

In an embodiment, the devices 108 remain connected with the SNP 106 all the time without interruption and may not require authentication each time prior to exchange of social content. In an embodiment, the server 202 may facilitate the devices 108 to sign in and sign out of the SNP 106. The sign in process may be initiated by the devices 108 and once a device's credentials are authenticated, the device such as 108a may be allowed to enter a social space provided by the SNP 106 to the device 108a. For example, the device 108a may view its profile, edit its profile, exchange profile information, view connections, initiate social activity, exchange social content, communicate with connections, display or publish content viewable publicly or by the connections, read or interpret or receive messages and social content published or communicated by the connections to the device 108a, analyze the content, and perform various other social activities only after signing into the social space dedicated for the device 108a by the server 202.

In an embodiment, a human participant such as 110a associated with the device 108a may act as an initiator and assist the device in connecting with the SNP 106 by submitting the credentials which once authenticated by the server 202 allows the device 108a and the initiator 110a to associate with the SNP 106 for social networking facilities such as social content exchange.

Figure 6:
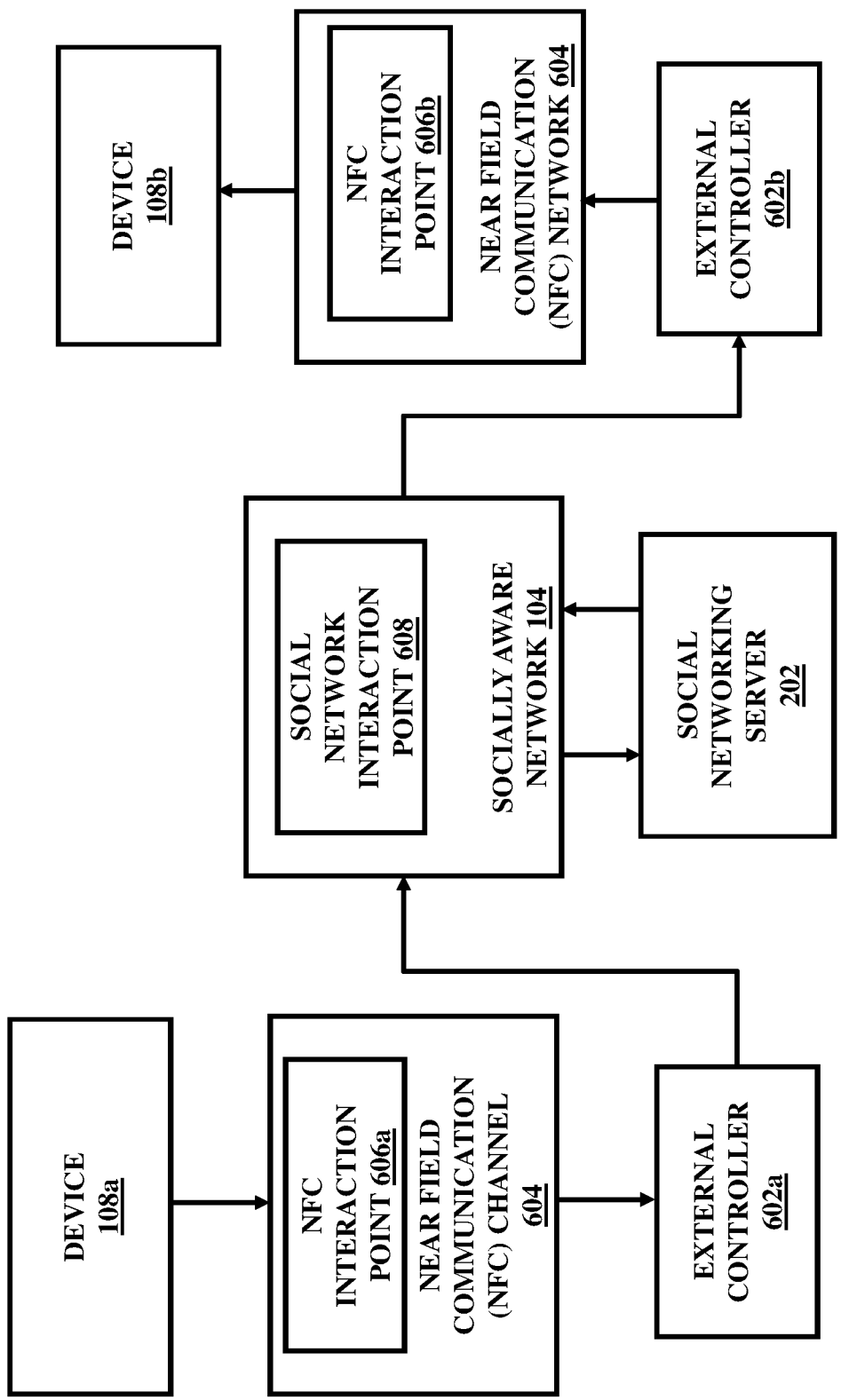
FIG. 6 illustrates a communication network for exchange of social content between devices in accordance with an embodiment herein.

FIG. 6, with reference to FIGS. 1 through 5, illustrates the communication network 104 for exchange of social content between the devices 108a and 108b. The device 108a is associated with an external controller 602a and the device 108b is associated with an external controller 602b. Each of the external controllers 602a and 602b is communicatively coupled to the respective devices 108a and 108b. The device participants 108a and 108b are connected with the external controllers 602a and 602b through a Near Field Communication (NFC) channel 604. For example, the device 108a communicates with the external controller 602a through the NFC channel 604 wherein the NFC channel or network 604 includes an NFC point 606a to connect with the external controller 602a. The device 108a interacts with the NFC point 606a of the NFC channel 604 to share social content and initiate a social activity. The communication point of the NFC channel 604 receives the social content transmitted by the device 108a and transfers the social content to the external controller 602a. The external controller 602a is communicatively coupled to the socially aware network or social network 104. In an embodiment, the devices 108a and 108b may include or be coupled to sensing units wherein the sensing and monitoring units are communicatively coupled to the external controllers 602a and 602b for communicating with the Near Field Communication point 606a of the Near Field Communication channel 604.

The social activity from the device 108a through the NFC network 604 automatically triggers a socially aware network point 608 of the socially aware network 104 so that the social content transmitted during the social activity results in the external controller 602a to further transmit the social content through the socially aware network point 608 of the social network channel 104 for socially sharing the social content to the remotely located participants including devices and non-devices participants. The social content received at the socially aware network point 608 is transmitted through the socially aware network 104 to the external controller 602b associated with the device 108b. The reception of the social content by the external controller 602b through the social network point 608 automatically triggers the 'Near Field Interaction Point' 606b of the Near Field Communication Network 604 for socially sharing the social content to the remotely located device 108b associated with the external controller 602b through the social networking server 202.

In an embodiment, the NFC network 604 is a short range communication network, wherein range of the NFC 604 is 100 meters so that the device 108a is located within proximity of 100 meters from the external controller 602a to communicate the social content with the external controller 602a. In an embodiment, the NFC network 604 is a Bluetooth™ network.

In an embodiment, the NFC 604 is a short range communication network, wherein range of the NFC network 604 is approximately thirty feet so that the device 108a is located within an approximate proximity of thirty feet from the external controller 602a to communicate the social content with the external device 108a. In an embodiment, the NFC network 604 is based on a Radio Frequency Identification (RFID) system such that the device 108a includes an RFID tag capable of being read by a reader communicatively coupled to or included within the external controller 602a.

In an embodiment, the NFC network 604 is a Body Area Network (BAN) or a wireless sensor network associated with the devices 108 that are wearable by a patient in some embodiments. The BAN includes a gateway to reach the social aware network 104 through the external controller 602a. The BAN includes monitoring sensors, motion detectors, and other sensing circuits associated with a subject. The BAN is further linked communicatively to a processing circuit and includes a power source and a transceiver (not shown) for communicating the social content to the external controller 602a through the gateway. The devices 108 include NFC tags programmable by NFC applications.

In an embodiment, the socially aware network 104 is a wide network such as a Wi-Fi or internet such that the network allows interconnection and automation among the plurality of remotely located participants such as 108*a* and 108*b* and between the participants 108 and the social networking server 202.

The social activity or social tasks may include devices 108 to voluntarily join the social network 104, disassociate or leave from the social network 104, extend interconnection with other like-minded devices, send invitations for connections to other devices 108, accept or reject invitations from other devices 108, view social profiles of other devices 108, exchange social activity information, establish social signatures for social authorization of profiles, create devices social groups, join devices groups, and leave devices groups voluntarily and non-voluntarily through an action of a participant 102. In an embodiment, the socially aware network 104 is a distributed network to allow interconnection and automation among the devices 108 distributed in a plurality of medical environments, or other high reliability and safety critical environments such as avionics, manufacturing, automotives and the like.

In an embodiment, the socially aware network 104 is a private and dedicated network for a medical environment or other high reliability and safety critical environments such as avionics, manufacturing, automotives and the like.

In some embodiments, at least a first device participant is independently incapable of performing computation tasks. In some embodiments, a device participant is connected with a second device participant that is incapable of performing computation tasks, a third device participant that is partially capable of performing computation tasks, a fourth smart device that is independently capable of performing computation tasks and a non-device participant associated with one of the device participants, wherein the first device participant transfers the social content to the second device, third device, fourth device and the non-device participant through the NFC channel 604 and the socially aware network 104, wherein the socially aware network 104 is automatically triggered upon receipt of the social content by the NFC interaction point 606*a* or 606*b*.

In an embodiment, the devices 108 can associate them with the SNP 106 or server 202 by creating an initial profile as discussed above so that the devices 108 are a part of the SNP 106. The devices 108 that are interconnected together through the SNP 106 can share the social content by initiating a social activity and are referred to as social connections. For example, if a pacemaker P1 connects to another pacemaker P2, and a ventilator V, the pacemaker P1 is said to include two connections—pacemaker P2 and ventilator V. Once the pacemaker P1 is connected to its two connections, it is free to share information with them and also to receive information from them upon initiation of a social activity by them. In an example, FIG. 7, with reference to FIGS. 1 through 6, illustrates an implantable medical device (IMD) 702 such as a pacemaker fitted inside a body of a patient 704. The pacemaker 702 is connected to an external controller 706 (which can be configured as the external controller 602*a* or 602*b*) that can be configured to communicate remotely to the communication channel 604 of the SNP 106 as discussed in conjunction with FIG. 6 above. The IMD 702 (IMD 702 can be any of the devices 108) can connect and share the information to another device such as 108*a* that is a member of the SNP 106. The IMD 702 can include components such as various sensors that can record data and/or monitor the performance of the IMD 702 and communicate it to the external controller 706 which can then transmit it to the server 202 and to another connection device such as 108*b*. In an embodiment, the data thus shared can be publicly announced and displayed over the profile of the IMD 702. In another embodiment, the data can be shared only to respective connections of the IMD 702 only.

Figure 7:
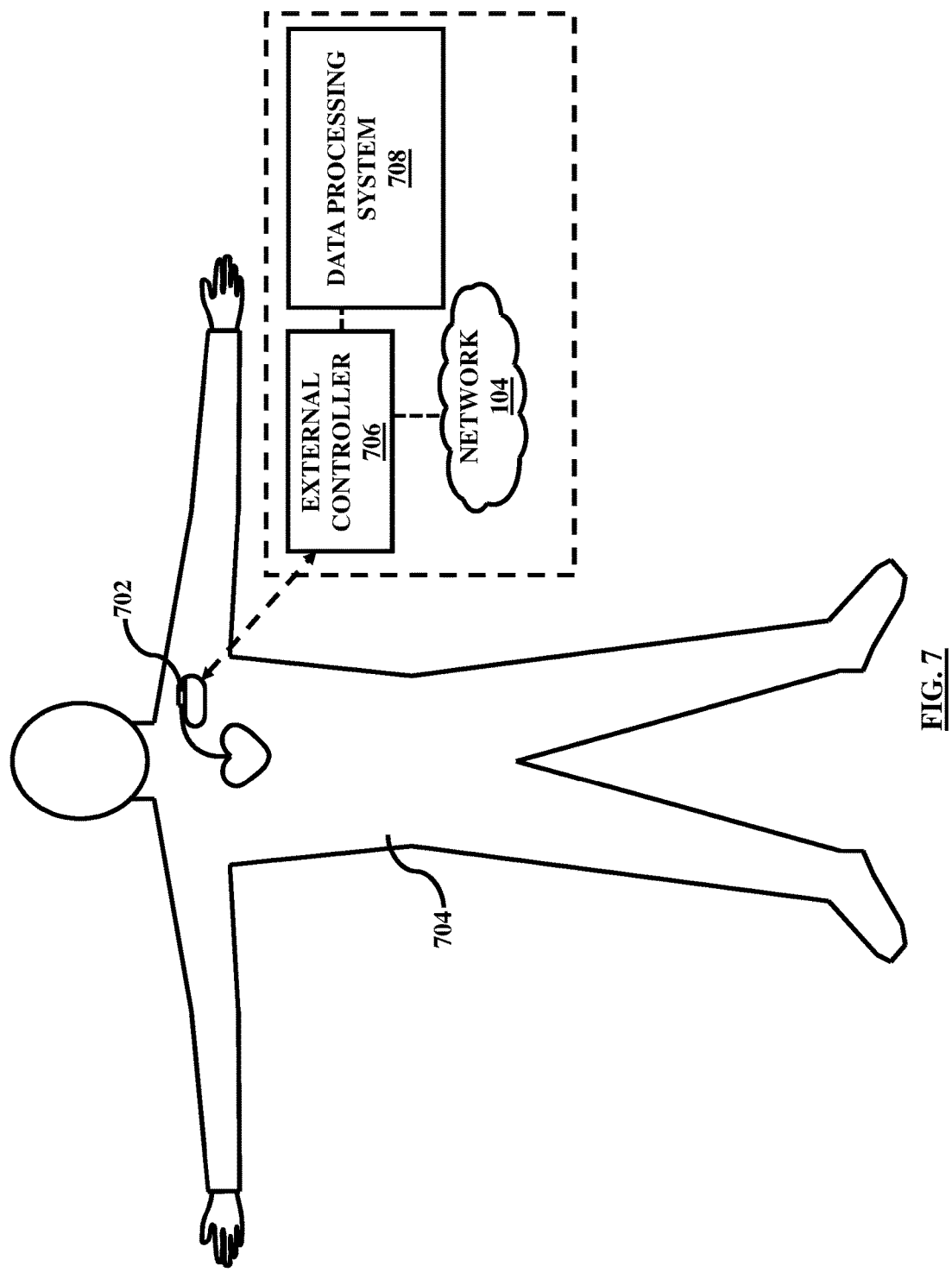
FIG. 7 illustrates an implantable medical device (IMD) fitted inside a body of a patient and communicatively coupled to a server for social networking service in accordance with an embodiment herein.

It should be appreciated that FIG. 7 illustrates an example of the IMD 702 as a medical device. In a similar manner, several other types of devices can also communicate among themselves through the SNP 106 or server 202. In an embodiment, the devices 108 can include various types of sensors and other monitoring devices. The sensors and the monitoring devices can collect and retrieve relevant information stored initially with the devices 108 or recorded over a period of performance. The retrieved information can be stored within a memory space of a device such as 108*a*. The devices 108 can manipulate the information that belongs to them such that they can share it to the connections, view it as and when they like or need, retrieve it as a historical data for analysis, display it publicly on the SNP website, hide it from viewing by others, hide it from viewing by others except connections, populate the profile data, and so on.

In an embodiment, the device 108*a* can connect with the SNP 106 and announce itself privately or publicly. Once connected, the device profile can be publicly or privately viewable by other devices or selected devices that are members of the SNP 106. In an embodiment, a device 108*a* can connect with another device 108*b* with whom the device 108*a* is interested to work with. For example, if the IMD 702 wants to work with some other like-minded device such as a defibrillator, the IMD 702 can send a request for connection and can connect once the request is accepted. In an embodiment, the sending and accepting of requests can be manually intervened or controlled by a user such as the patient 704 or his doctor who may or may not be an SNP participant. In another embodiment, the sending and accepting of requests can be automatically processed. For this, specific programming can be performed within the external programmer 706 of the IMD 702. For example, the external programmer 706 can be programmed to send invitations to a like-minded device as it connects over the SNP 106. The programmer 706 stores relevant data and instructions and issues commands.

In an embodiment, the medical device such as the IMD 702 can include a RFID chip (not shown) that is configured to store information relevant to the IMD 702. The information can be read by a reader that can be integrated within the external controller or programmer 706 or in any other external device. As and when any information is transmitted from the IMD 702 to the SNP 106 or social networking server 202, the reader decodes the RFID tag within the IMD 702 and associates the data with the relevant information. Therefore, the server 202 can automatically identify the IMD 702 and can grant permission to the profile of the IMD 702. Subsequently, the process of information sharing can occur automatically. Similarly, several other devices 108 can be associated with their pertinent information, data and metadata and can accordingly be updated. In several other embodiments, various other communication mechanisms may be employed for exchange of social content and/or sharing of social invitations.

In an embodiment, the device such as IMD 702 can find like-minded devices for extending a social network based on parameters such as profiles of a community of the devices using it, for example, a web based data processing system 708 that can be directly through wire or wirelessly or remotely connected to the device 702. The data processing system 708 can be integrated within or communicatively coupled with the external programmer 706 and can interface remotely to the SNP 106 or server 202. The data processing system 708 can perform functions such as query a database of profiles of the devices 108 such as of a community of the devices 108. The query can include information pertinent to a device such as device 108*a* and could include, without limitations, the name of the device 108*a*, identifier of the device 108*a*, type of the device 108*a*, medical conditions treated by the device 108*a*, therapies delivered by the device 108*a*, patient identifier associated with the device 108*a*, life style factors associated with a patient associated with the device 108*a*, environmental factors, contextual factors, historical records stored in the device 108*a*, and so on. Upon searching, the device 108*a* can perform various functions such as view the matching profiles, connect with them, post messages for them, like or dislike their posts, use their data upon request, share information with them, and perform further queries or refine the queries or share other social content.

In an embodiment, the data processing system 708 as discussed above can work in a completely automated manner along with the devices 108 with the use of various technologies implemented thereon such as RFID, bar code identification, wireless and wired mode of information sharing, sensor based actions and reactions, BAN, and so on without limitations. This can be achieved without any manual intervention. In another embodiment, a limited or complete manual intervention may be involved. For example, the devices 108 can be associated with their patients or physicians, or other responsible persons and they can operate and control the devices interactivity with the server 202.

Figure 8:
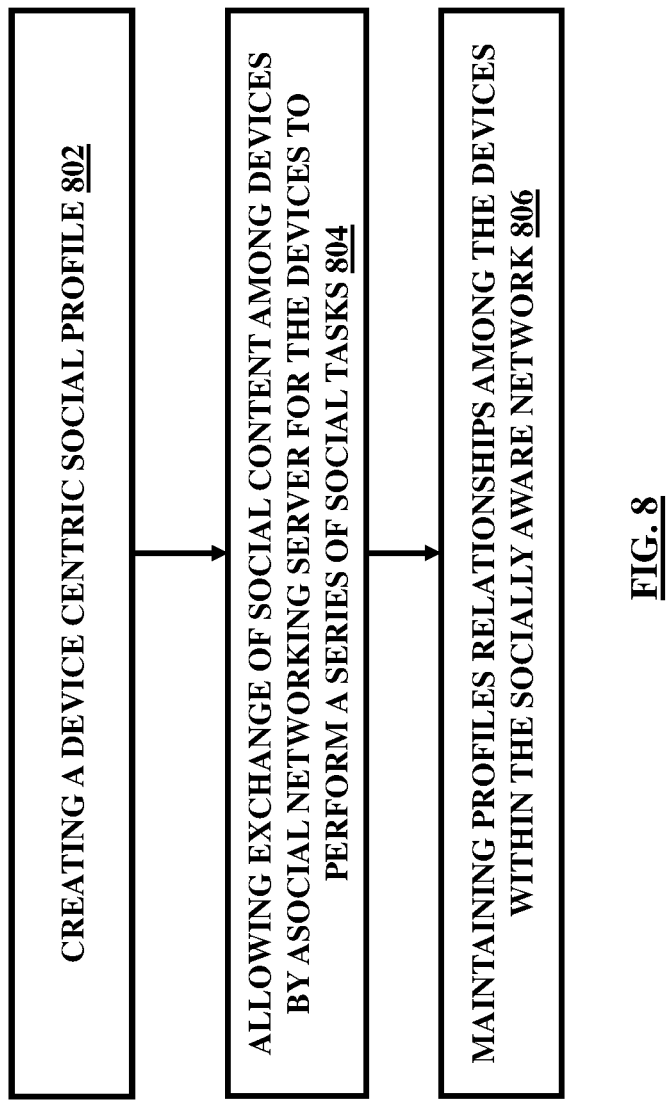
FIG. 8 illustrates a method flowchart for integration of a plurality of participants in an embodiment herein.

FIG. 8, with reference to FIGS. 1 through 7, illustrates a method flowchart for integration of a plurality of participants 102 including a plurality of devices 108 and non-devices 110 through the social networking platform 106. At step 802, the method includes creating a device centric social profile for each of the plurality of devices 108. The profile is a social representation of a respective device such as 108*a* within the socially aware network 104 and the device 108*a* is identifiable by other devices 108 and the social networking server 202 through the devices social profiles. At step 804, the method further includes allowing the exchange of social content among the devices 108 by the social networking server 202 for the devices 108 to perform a series of social tasks. The social content is exchanged through a first communication channel and a second communication channel. The first communication channel links a device 108*a* with an external controller such as 602*a* and the second communication channel links the external controller 602*a* with the socially aware network 104. In embodiments, the first communication channel may include a Bluetooth™ network, RFID-based network or a Body Area Network or Body Sensor Network. The second communication channel may include a wide area network such as the Internet or Wi-Fi or the socially aware network 104 as discussed above. The social tasks may include one or more of voluntarily joining the social network 104, disassociating or leaving from the social network 104, extending interconnection with other like-minded devices, sending invitations for connections to other devices 108, accepting or rejecting invitations from other devices 108, viewing profiles of other devices 108, exchanging social activity information, establishing social signatures for social authorization of profiles, creating devices social groups, joining devices groups, and leaving devices groups voluntarily or upon initiation of an activity by a participant 102.

At step 806, the method may include maintaining profiles relationships among the devices 108 within the socially aware network 104. The relationships may be of several types as already discussed above in conjunction with various figures. The social relationships may be maintained in the form of a social map as will be discussed later.

In an embodiment, the methods above are performed in the network 104 of devices 108 that include at least one device with partially incapable computation capabilities. The device with partially incapable computation capabilities is connected with an external controller through the first communication channel so that a communication point of the first channel is adapted to receive social content in real-time from the device. The second channel allows information sharing between the external controller and the social networking server 202.

In some embodiments, at least some of the devices interconnected through the social networking server 202 for social content exchange are associated with patients wherein the medical devices associated with the patients monitor vital signs of patients or perform defined functions for health management. Exemplary medical devices without limitations have been discussed above.

The method may comprise facilitating a web-based activity among the plurality of devices 108 for sharing the social content. The method may comprise storing information pertaining to an associated relationship of a device 108*a* with other devices. The method may comprise facilitating the recommendation of a connection device by another device based on noticed past behavior of the connection device by the other device. The method may comprise encrypting and decrypting the social content during exchange of the social content among the devices 108. The method may comprise federating the profile into a respective installation social profile, manufacturing social profile, operation social profile, schedules social profile, network social profile, security social profile, reliability social profile, human social profile, time social profile, and the location social profile.

Figure 9:
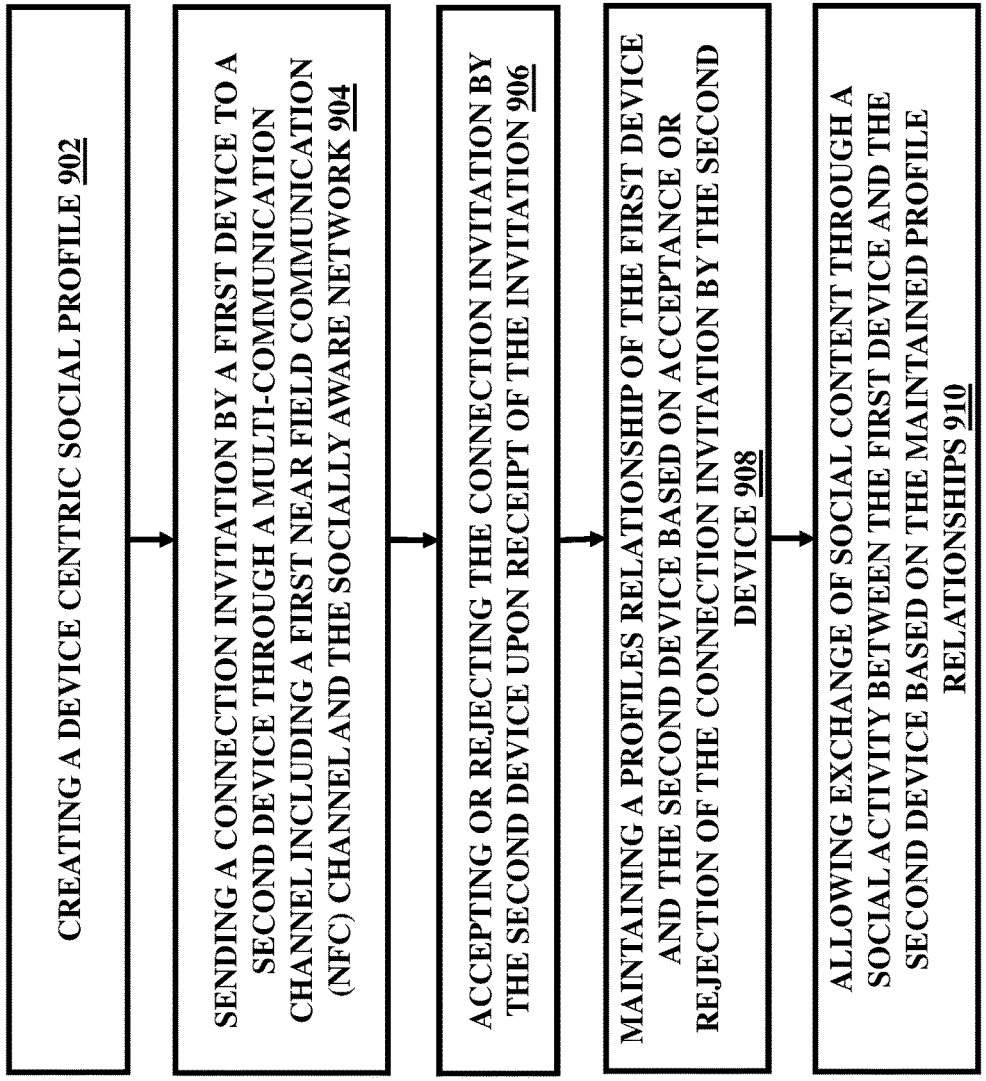
FIG. 9 illustrates a method flowchart for integration of a plurality of participants in an embodiment of an embodiment herein.

FIG. 9, with reference to FIGS. 1 through 8, illustrates a method flowchart for integration of a plurality of participants 102 including a plurality of devices 108 and non-devices 110 through the social networking platform 106 or server 202, in accordance the embodiments herein.

At step 902, the method includes creating a device centric social profile for each of the plurality of devices 108. The profile is a social representation of a respective device such as 108*a* within the socially aware network 104 and the device such as device 108*a* is identifiable by other devices and the social networking server 202 through the profile. At step 904, the method includes sending a connection invitation by a first device 108*a* to a second device 108*b* through the multi-communication channel including the first Near Field Communication (NFC) channel 604 and the socially aware network 604. The step 904 of sending of the invitation includes sending of the invitation from the first device 108*a* to the external controller 602*a* associated with the first device 108*a* through the first NFC channel 604, transferring the invitation from the external controller 602*a* to the network point 608 of the socially aware network 104, and transferring of the invitation from the network point 608 through the socially aware network 104 to the device 108*b*. At step 906, the method may include accepting or rejecting the connection invitation by the second device 108*b* upon receipt of the invitation by the second device 108*b*. At step 908, the method may include maintaining a profiles relationship of the first device 108*a* and the second device 108*b* based on acceptance or rejection of the connection invitation by the second device 108*b*.

At step 910, the method includes allowing the exchange of social content through a social activity between the first device 108a and the second device 108b based on the maintained profile relationships. The social activity includes a series of social tasks including one or more of: devices 108 to voluntarily join the social network 104, disassociate or leave from the social network 104, extend interconnection with other like-minded devices, send invitations for connections to other devices 108, accept or reject invitations from other devices 108, view profiles of other devices 108, exchange social activity information, establish social signatures for social authorization of profiles, create devices social groups, join devices groups, and leave devices groups voluntarily or upon initiation of an activity by a participant 102, and the like without limitations.

Figure 10:
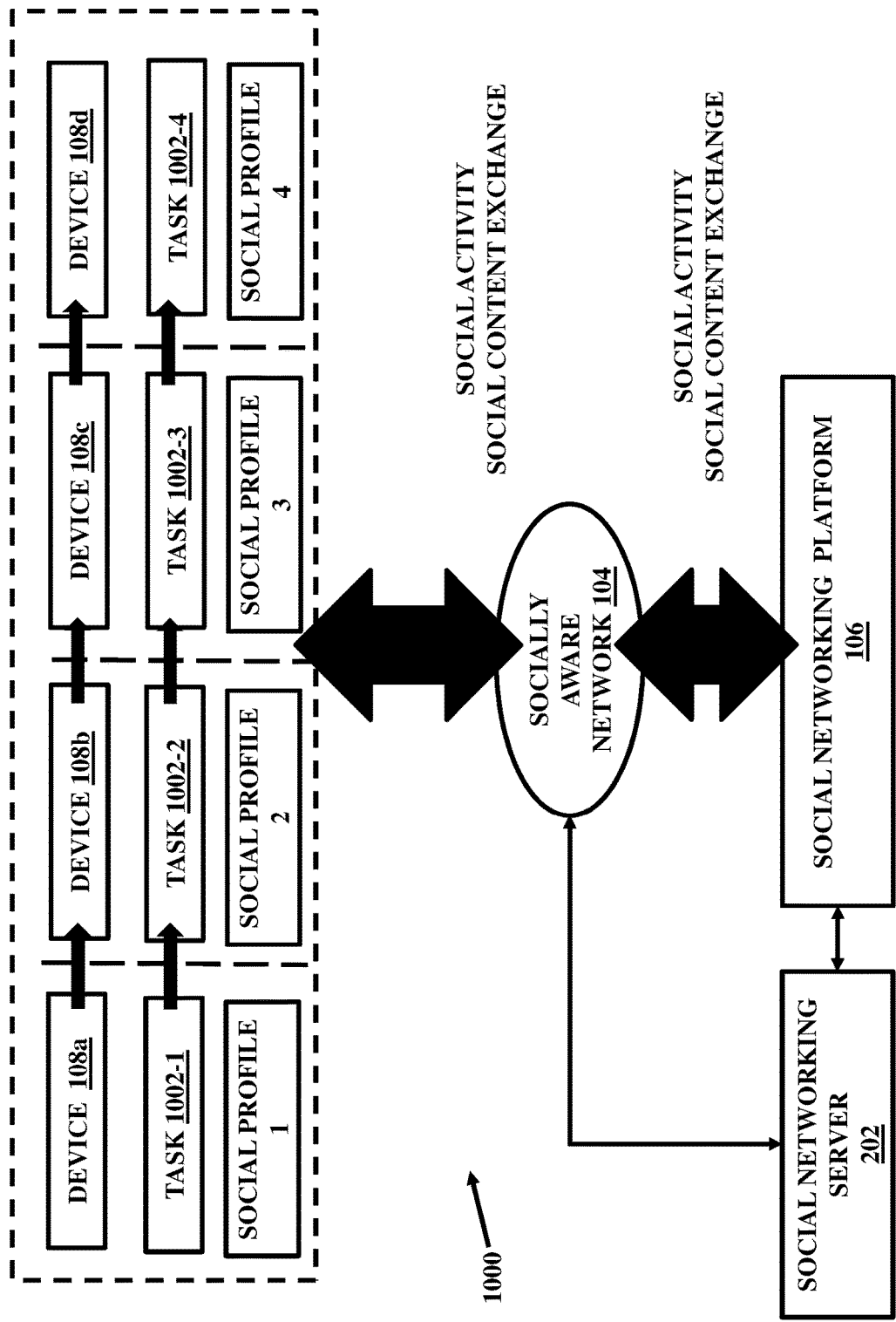
FIG. 10 illustrates an ecosystem for facilitating sequential, synchronous and automatically coordinated operation of the plurality of devices through interactive elements involving a chain of tasks and devices, in an embodiment herein.

FIG. 10, with reference to FIGS. 1 through 9, illustrates an ecosystem 1000 for facilitating sequential, synchronous and automatically coordinated operation of the plurality of devices 108 through interactive elements involving a chain of tasks and devices 108. The ecosystem 1000 includes the social networking platform 106 implemented through the social networking server 202. The plurality of devices 108 are interconnected and coupled with the server 202 through the socially aware network 104. The socially aware network 104 and the communication channel for interconnection of the devices 108 and the server 202 may be enabled in ways that are discussed above without limitations.

FIG. 10 shows a first device 108a, a second device 108b, a third device 108c, and a fourth device 108d which perform a first task 1002-1, a second task 1002-2, a third task 1002-3, and a fourth task 1002-4 respectively. The devices 108 are identified through their respective social profiles as shown in the figure. The interactive chain of elements includes the social profiles, tasks, and devices as shown in the figure.

The social networking server 202 provides a social networking service to the plurality of devices 108 so that each of the plurality of devices 108 are connected to the social networking service by associating the respective social profiles with the social networking server 202. The respective social profiles are social representation of the devices 108. The social networking server 202 is programmed to allow the devices 108 to coordinate for a synchronous social times-based functioning. The server 202 is programmed to associate connection-type social device relationships between the devices 108. The connection type social relationship is established after at least two devices accept one another as trustworthy connections after reviewing the social profiles. The trustworthiness may be defined based on factors such as like-mindedness of the devices 108, related functioning, completeness of tasks 1002, and the like. The server 202 may, for example, be programmed to provide a facility or an interface to the first device 108a for allowing the first device 108a to send a connection invitation request to the second device 108b. Once the invitation request is accepted by the second device 108b, the first device 108a and the second device 108b can form a part of the interactive chain of the devices 108 and tasks 1002-1 through 1002-4, wherein the server 202 may be programmed to provide a facility to the first device 108a and the second device 108b to allow them to coordinate with one another through a social activity processed by the server 202.

The server 202 is programmed to receive the social content from the first device 108a once the first device 108a has established the connection-type relationship with another device such as the second device 108b. The social content may include several instructions for the second device 108b. For example, in an embodiment, the social content may include an instruction for the second device 108b to cause a synchronous and non-conflicting performance between the first device 108a and the second device 108b. The synchronous and non-conflicting performance is discussed below in detail with examples of the four devices shown in FIG. 10 in a medical environment. However, it should be appreciated that several other devices may also be included in the interactive chain from medical environments, or other environments such as avionics, power, automotive, and the like. The devices 108 can be located within a single environment or distributed in several environments.

The first, second, third, and fourth tasks 1002-1 through 1002-4 indicate elements of a complete treatment function that a patient is operated with. The first task 1002-1 and the second task 1002-2 are performed simultaneously for the first 10 minutes for a patient with defined characteristics. The first task 1002-1 then stops and the third task 1002-3 begins which continues along with the second task 1002-2 for another 10 minutes after which the second task 1002-2 stops. The third task 1002-3 still continues for another 15 minutes unless the patient body shows undesirable physiological indications. If the physiological parameters sensed are not satisfactory, then the fourth task 1002-4 begins along with the third task 1002-3. In view of the various tasks required to be performed in a defined sequence and for defined time periods based on the patient's physiological characteristics, the various devices 108 from those shown are made to function. For example, in accordance with the above sequence, the first device 108a and the second device 108b operate for the first ten minutes simultaneously. The first device 108a then stops and the third device 108c starts functioning. The second device 108b and the third device 108c operate in parallel for another 10 minutes. The second device 108b then stops and the third device 108c still operates for another 15 minutes unless the patient's body shows undesirable physiological parameters. If the physiological parameters sensed are not satisfactory, then the fourth device 108d starts functioning along with the third device 108a.

In accordance with the synchronous functioning of the four devices 108, the first device 108a may first need to locate the other three devices within the socially aware network 104. The server 202 may be programmed to allow the devices 108 to create their social profiles and subscribe with the social networking platform 106 for social activity. The first device 108a with the first social profile may be programmed by a coordinator to function in a defined manner for a defined patient to perform a set of first tasks and a set of second tasks in a defined sequence avoiding certain conflicts. The set of first tasks are primary tasks that are performed by the first device 108a itself. The set of second tasks are required to be performed by other devices. Based on the programmed instructions, the first device 108a identifies that the second, third and fourth tasks 1002-2, 1002-3, 1002-4 are to be performed by other devices. The first device 108a may be programmed with device characteristics and specifications that can perform the respective second, third and fourth tasks 1002-2, 1002-3, 1002-4. The server 202 is programmed to allow the first device 108a to initiate a search request, as soon as the first device 108a is connected with the social networking server 202, for social profiles that indicate similar capabilities of devices as the device programmed instructions include for the devices 108 to perform the second, third and fourth tasks 1002-2, 1002-3, 1002-4. The first device 108a shares the social content that includes a social description of the devices required to link with the first device 108a to perform a set of tasks for coordinated operation. The server 202 is programmed to receive the social content and perform a search within the socially aware network 104 to locate social profiles that are fit to coordinate with the first device 108a. The server 202 may identify several profiles and share the profiles with the first device 108a. Alternatively, the server 202 may shortlist the profiles and share the three profiles corresponding to the second, third, and fourth devices 108b, 108c, and 108d only with the first device 108a. In the first case, a manual intervention may be needed by a device coordinator to shortlist the best profiles. Alternatively, the device 108a may also be programmed to shortlist the necessary profiles.

The server 202 is programmed to facilitate the first device 108a to initiate a social activity with the second, third, and fourth devices 108b, 108c, and 108d. The social activity begins by sending a social message from the first device 108a to the other three devices 108b, 108c, and 108d that include a social connection invitation request. The server 202 receives the social content that is indicative of the social connection request with the second, third, and fourth devices 108b, 108c, and 108d. In an example, the request may be sent separately to the three devices 108b, 108c, and 108d. In another example, a unified social invitation request may be broadcasted in a single social message to the three devices 108b, 108c, and 108d. The server 202 may be programmed to notify the three devices 108b, 108c, and 108d of the social message or content from the first device 108a. The social content may also display a social profile of the first device 108a so that the three devices 108b, 108c, and 108d may identify and decide whether the devices 108b, 108c, and 108d are capable and available enough to support the first device 108a in performing the patient treatment tasks synchronously and in a non-conflicting manner as desired by the first device 108a. The server 202 may further be programmed to allow the three devices 108b, 108c, and 108d to accept or reject the invitation based on the availability and capability of the three devices 108b, 108c, and 108d to support the first device 108a in performing the patient treatment tasks as defined by the first device 108a in the invitation request. In an embodiment, the invitation request may not include the information pertinent to the social tasks and the patient treatment tasks. In such cases, the accepting or rejecting of the invitation may simply depend on whether the devices 108b, 108c, and 108d want to accept or reject the invitation based on the programmed guidelines of the devices 108b, 108c, and 108d such as like-mindedness, historical contextual behavior of the social interaction, and the like. In an example, a human intervention may be needed to accept or reject the invitation. The server 202 may be programmed to provide a user interface to the three devices 108b, 108c, and 108d to allow a coordinator to view the information contained in the social invitation request and also allow the coordinator to accept or reject the invitation. The server 202 may be programmed to personalize the user interface contextually based on the nature of device 108a. The server 202 may include a personalization engine which may implement a set of executable specifications to personalize the interface for the type of device using social profiles information of the device 108a. The server 202 may also store a list of graphic tools, a set of keywords, a medical dictionary, a medical database, tables, charts, histograms etc that can be used repeatedly in context of the devices social profiles to execute the specifications for personalizing the interface. For example, the interface for a heart beat monitor may be different from an interface for a ventilator or a pacemaker or drug delivery setup, and the like.

If one or more of the devices 108b, 108c, and 108d reject the invitations, the first device 108a may reinitiate a search request and send invitations to other devices if available in the network 104 or else will notify an operator about no device being available.

If the devices 108b, 108c, and 108d accept the notification, the three devices 108b, 108c, and 108d become connections of the first device 108a. The server 202 is programmed to update the social profile of the first device 108a to include the second, third, and fourth devices 108b, 108c, and 108d as connections in the updated social profile. An application component enabled by the server 202 similar to the application component 502 discussed above may create a user interface or modify the social profile user interface of the first device 108a as a coordinator of the first device 108a to view a connection screen section on the user interface, wherein the connection screen section indicates a list of connections (the three devices 108b, 108c, and 108d) of the first device 108a and also list titles of the connection generated based on their social profiles. The server 202 may be programmed to allow the coordinator to personalize the connection screen section of the first device 108a to view from a set of available fields on the user interface such as title field, device name, device capabilities, device state (idle, busy, do not disturb, away etc.), and the like. For example, the away state may indicate that the device is not available and is out for maintenance, idle state may be indicative of the device to be available to support a device in a chain of patient treatment tasks, busy state may be indicative of the device to be already busy in performing a treatment task for a patient, and the like.

The server 202 is programmed to allow the first device 108a to initiate a social activity by sending social content for requesting the other three devices 108b, 108c, and 108d to interact with the first device 108a to perform the patient treatment task as is discussed above as an example. The first device 108a sends out the social content to each of the three devices 108b, 108c, and 108d indicative of the details of the respective tasks to be performed by the three devices 108b, 108c, and 108d. For example, the social content for the second device 108b may be indicative of the action or task performed by the first device 108a and an instruction to the second device 108b to perform an action in association with action timelines, wherein the action timelines are indicative of time points associated with the action and define time when actual action should occur at the second device 108b. The server 202 is programmed to receive the social content indicative of the social action performed by the first device 108a and the instruction to the second device 108b to perform the action in association with action timelines, wherein the action timelines are indicative of time points associated with the action and define time when actual action should occur at the second device 108b. The server 202 is programmed to notify the second device 108b of the social content received from the first device 108a that includes the instruction to the second device 108b to perform the action in association with the action timelines. Similarly, the server 202 receives social content to be notified to the third and the fourth devices 108c and 108d. The second, third, and fourth devices 108b, 108c, and 108d upon receipt of the instruction sends a confirmation request to the first device 108a to guarantee performance of their respective actions at the defined timelines. In an example, prior to sending the social content to the devices, the first device 108a or the associated coordinator may view the status of the devices 108b, 108c, and 108d so that the first device 108a may identify which device is available and idle at a time indicated by the social timelines. This increases the probability of the devices 108b, 108c, and 108d to be available and confirm for their actions performance at the social timelines.

In an example, the devices 108 are associated with respective external controllers similar to 602a that allow interconnection of the devices 108 with the social networking server 202 to allow social activity through the social networking service.

As discussed above, in an example, the server 202 is further programmed to provide a facility to the first device 108a to allow the first device 108a to initiate a search request for like-minded devices based on information contained in the social profile of the first device 108a and current operating characteristics of the first device 108a. The server 202 may be programmed to search for the like-minded devices from the plurality of devices 108 and provide a list of the like-minded devices including their social profiles and network links for the like-minded devices so as to allow the first device 108a to send a connection request to one or more of the searched like-minded devices. The one or more devices are shortlisted by an external controller such as 602a in association with information stored in the external controller 602a and the current operating characteristics of the first device 108a or through an intervention of a social human coordinator of the device 108a as identified by the device social profile.

The devices 108 can vary in terms of their computation capabilities as discussed earlier.

In an example, each of the plurality of devices 108 are connected to a sensing and monitoring unit for monitoring and recording device activities for social exchange through the social activity.

In an example, the social activities includes posting a connection request for the second, third or fourth devices 108b, 108c, 108d for associating a relationship with the three devices 108b, 108c, 108d and cause a synchronous and non-conflicting performance between the first device 108a and the other three devices 108b, 108c, 108d. The social activities can include accepting or rejecting a connection invitation by the devices 108b, 108c, 108d in response to a request sent by the first device 108a for associating a relationship with the three devices 108b, 108c, 108d toward a synchronous and non-conflicting performance between the first device 108a and the other devices 108b, 108c, 108d.

Figure 11:
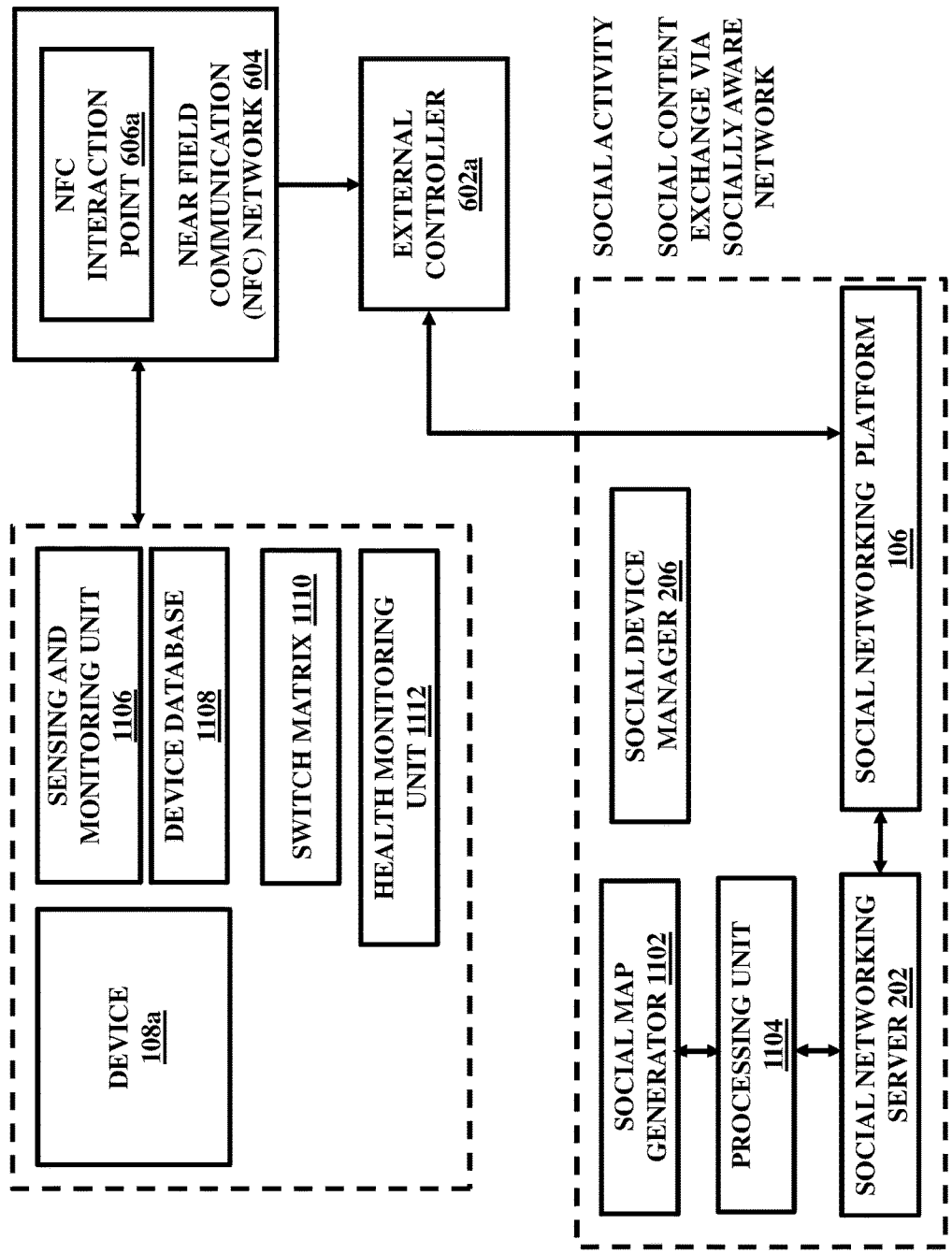
FIG. 11 illustrates an example of a device interconnected with a social networking platform in an embodiment herein.

FIG. 11, with reference to FIGS. 1 through 10, illustrates an example of the ecosystem 1000 of FIG. 10 in an embodiment herein. As shown, the device 108a is connected with the external controller 602 that is adapted to communicate with the device 108a through the NFC communication channel 604 via the NFC point 606a. The NFC point 606a and the NFC 604 have been discussed earlier in detail. The external controller 602a may be coupled communicatively with the social networking server 202 through the socially aware network 104 (not shown in FIG. 11). In an embodiment, the device 108a is communicatively connected to the respective external controller 602a through the Near Field Communication (NFC) channel 604 so that the communication point 606a of the NFC channel 604 receives the social content from the first device 108a and transfers the social content to the external controller 602a. The external controller 602a is further communicatively coupled to the network point 608 of the socially aware network 104, wherein when one of the socially aware network points 608 and the NFC point 606a receives the social content, the other is automatically activated to further communicate the social content. The socially aware network 104 can be a private network or a distributed network as discussed earlier. For example, the socially aware network 104 is a private and dedicated network for a medical environment so that the server 202 allows the first device 108a to send a connection notification to the second device 108b via the socially aware network point 608 and the NFC point 606a, and once the second device 108b accepts the connection notification, the first device 108a sends the social content to the second device 108b via the socially aware network point 608 and NFC point 606a, wherein the social content is indicative of an action to be performed by the second device 108b at a social event timeline specified by the social content. In an example, the socially aware network 104 is a distributed network so that the server 202 allows the first device 108a to send a connection notification to the second device 108b via the socially aware network point 608 and the NFC point 606a, and once the second device 108a accepts the connection notification, the first device 108a sends the social content to the second device 108b via the NFC and socially aware network points 608 and 606a, wherein the social content is indicative of an action to be performed by the second device 108b at a social event timeline specified by the social content.

The social networking server 202 also includes or is coupled to a social map generator 1102. The social map generator 1102 generates the social graph among the interactive chain of the tasks and the devices 108 based on connection relationships among the plurality of devices 108, wherein the social map includes a set of nodes that are representative of devices 108 and a set of edges connecting the nodes that are representative of relationships between the connected devices 108. An edge length may represent proximity between the devices 108.

In accordance with the illustrated embodiment, the social networking server 202 (also simply referred to as server interchangeably throughout the document) includes or is coupled to a processing unit 1104 configured to execute the programmed instructions of the server 202. The processing unit 1104 further processes the social graph for a device to identify proximity of the interconnected devices 108.

In an embodiment, the server 202 may be coupled to the social device manager 206. The social device manager 206 includes a relationship manager 402 (of FIG. 4) for associating a relationship of the first device 108a with the other devices after the second, third, and the fourth devices 108b, 108c, and 108d accept the connection invitations sent out by the first device 108a. The relationships may indicate association of the one or more devices 108b, 108c, and 108d with the first device 108a in several forms such as a manufacturing relationship, installation relationship, operation relationship, network relationship, security relationship, reliability relationship, schedules relationship, location relationship, time relationship, and the like. The relationships may be established by the server 202 to avoid conflict during coordinated functioning of the devices 108. For example, if the first device 108a does not support a low reliability device for a patient in a defined physiological state because of age and criticality parameters of the patient, the third device 108c that may be a low reliability device may not be used for the defined patient. However, the device 108c may still be interconnected with the first device 108a for another patient treatment function for a younger patient where the low reliability is not such an issue. Such types of relationships are established to facilitate the server 202 to allow interconnection for a patient treatment process or function involving a chain of devices and tasks elements.

The established relationships are stored in the relationships information storage module 404 communicatively connected with the server 202. The storage module 404 may include a memory circuit. The server 202 may be communicatively coupled to the social profiles manager 204. The social profiles manager 204 has been discussed earlier.

In an example, the devices 108 may be programmed to function in accordance with the programmed instructions of the server 202 to facilitate social information or content exchange through social activities facilitated by the server 202. The first device 108a is associated with a sensing and monitoring unit 1106 for monitoring and recording device activities for social exchange through the social activity. Similarly, other devices may also be associated with monitoring and sensing units. The sensing unit 1106 detects a change in performance state of the device 108a and generates an input signal. The first device 108a further includes a database 1108 to store operation and performance parameters of the first device 108a in association with coordination and conflicting data with connection devices of the first device 108a. For example, the database 1108 of the first device 108a may include the chain of tasks and devices 108 involved in a patient treatment process in association with specific social timelines. The database 1108 also stores operation and performance characteristics and parameters of the first device 108a. The external controller 602a associated with the first device 108a processes the generated input signal and correlates the detected signal with information stored in the database 1108 and generates a second signal. The second signal includes the social content and is indicative of the action performed by the first device 108a at specific timelines and instructions for the second, third, and fourth devices 108b, 108c, and 108d to perform specific functions at defined social timelines to facilitate the coordinated functioning of the devices 108 to complete the patient treatment process.

In an example, the devices 108 are associated with a switch matrix 1110 that causes the devices 108 to change their operating state based on the social content requesting a change in the operating state at specific social timelines.

In an embodiment, each of the devices 108 includes or is coupled to a health monitoring unit 1112 that monitors health parameters of the respective devices 108 and compares with threshold health parameters of the devices 108 to ascertain health status of the devices 108. The health monitoring unit 1112 generates a signal indicative of the health status below the threshold limit when the ascertained health status is indicative of a health below a threshold limit. The server 302 allows the devices 108 to initiate social activities that include communicating the health status to a set of connection devices so the connection devices switches to tasks performed by the devices 108 in case of a health failure of the devices 108. In an example, the health parameters of the devices 108 are identified by monitoring a set of patient's physiological parameters that are controlled by the devices 108, wherein a drop in desired physiological state of the patient is indicative of a health failure of the devices 108 that operate on the patient.

In some embodiments, the social activities include posting a search request for identification and receiving profile information of an adjacent device in the sequential and synchronous operation in response to the search request by a device 108a, wherein upon receipt of the profile information, the device 108a sends a connection request to the adjacent device. In an example, the adjacent device may be identified by the processing unit with the use of the social map. In some embodiments, the social activities include posting a search request for identification and receiving profile information of related devices in response to the search request by a device 108a, wherein upon receipt of the profile information, the device 108a sends a connection request to one or more of the related devices. In examples, each action performed by a device 108a connected through the social networking server 202 is associated with a social action timeline indicative of when particular actions occur at devices 108, wherein the social action timelines are communicated to respective connection devices for integrating devices synchronous actions. In an example, the information pertinent to the social action timelines associated with actions to occur at the devices 108 may be stored in the devices social profiles.

Figure 12:
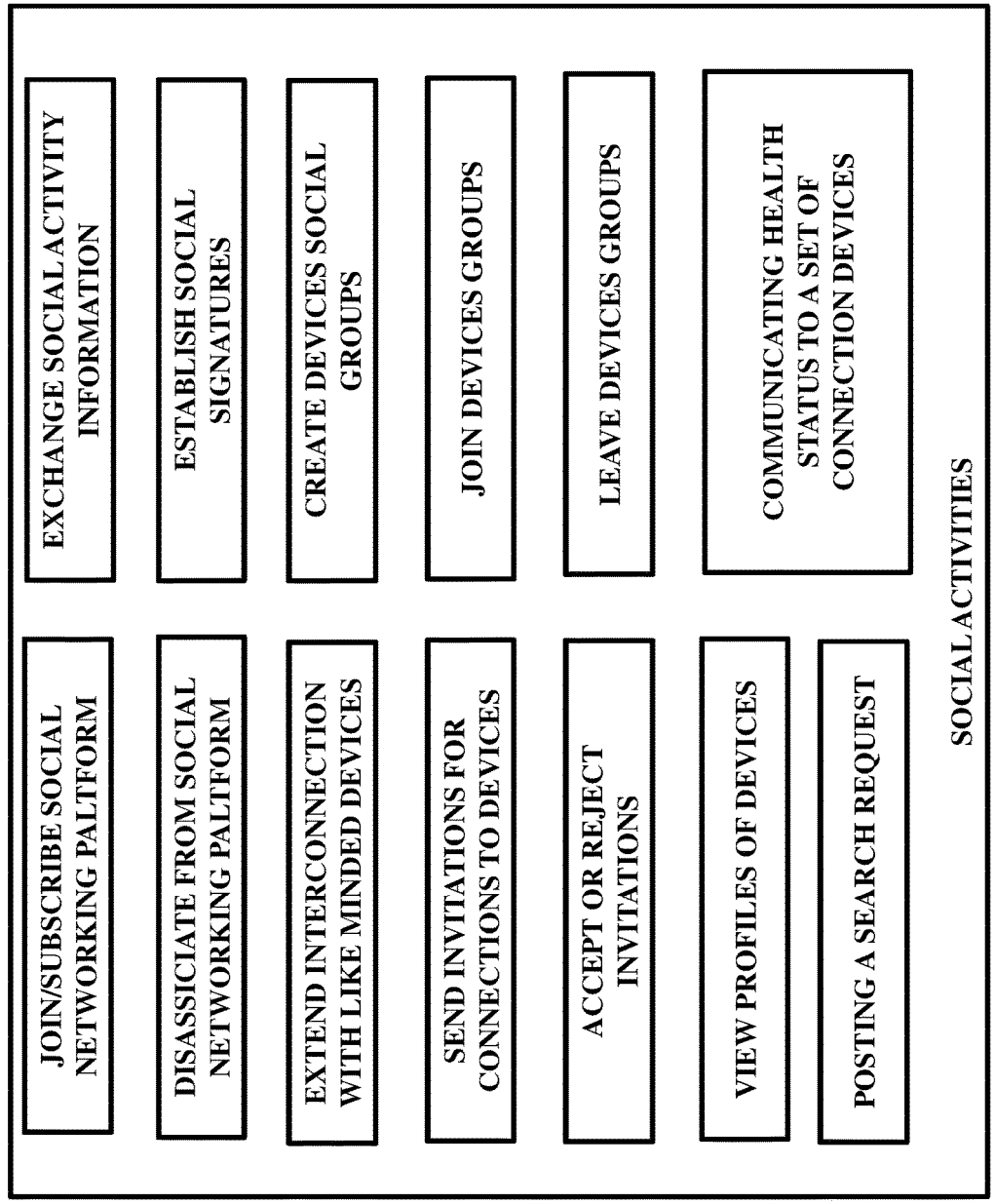
FIG. 12 illustrates a list of exemplary social activities that a server may be programmed to allow a plurality of devices to perform in accordance with an embodiment herein.

FIG. 12, with reference to FIGS. 1 through 11, illustrates a list of exemplary social activities without limitations that the server 202 may be programmed to allow the devices 108 to perform. A shown, the social activities may include joining or subscribing with the social networking platform 106 or the social networking server 202 that enables the networking platform 106, disassociation from the social networking platform 106 or server 202, extending interconnection with like-minded devices, sending invitations for connections to the devices 108, accepting or rejecting invitations, viewing profiles of the devices 108, posting a search request, exchanging social activity information, establishing social signatures for devices social authorization prior to making a social decision such as accepting or rejecting a social invitation, creating devices social groups, joining devices social groups, leave devices social groups, communicate health status to a set of connection devices, and the like without limitations.

Figure 13:
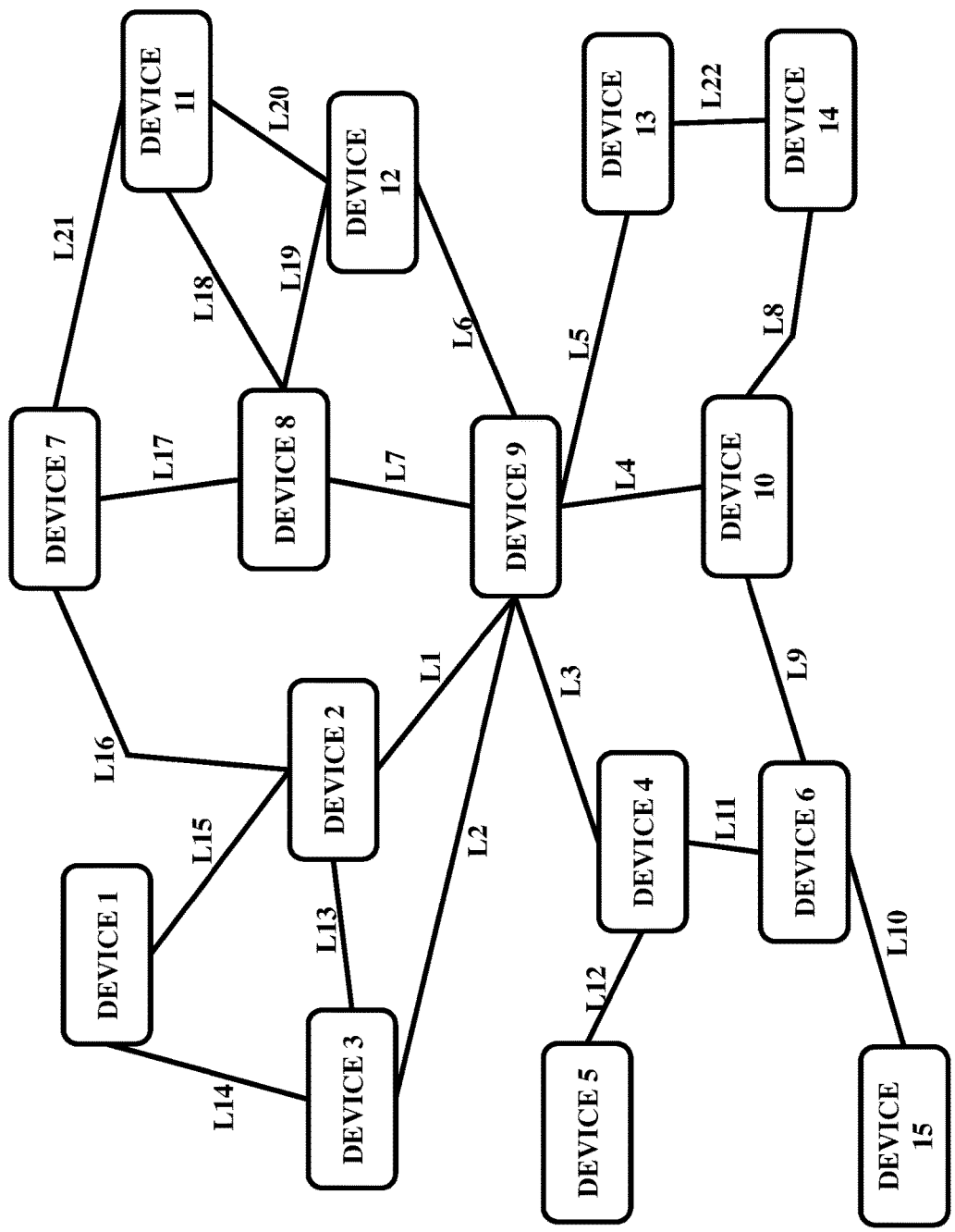
FIG. 13 illustrates an example of a social map showing interconnection of exemplary devices through the social map in accordance with an embodiment herein.

FIG. 13, with reference to FIGS. 1 through 12, illustrates an example of a social map showing interconnection of exemplary devices through the social map. The social map is generated by the social map generator 1102 based on the connection relationships among the devices. The social map includes a set of nodes that are representative of the devices and a set of edges connecting the nodes that are representative of relationships between the connected devices. An edge length may represent proximity between the devices. The processing unit 1104 may be programmed to interpret the social map and generate a signal that is indicative of such as without limitations number of connections for a device, location of the connection devices from the device, list or priority devices with respect to locations that is the connection devices in association with the location from the device and the like. An output from interpretation of the social map may be used by the server 202 to respond to a device in response to a search request for knowing proximity devices with like-mindedness.

In an example, the social map may be used for adverse event analysis (when devices misbehave), exception reporting (when devices need to report exceptions), utilization analysis (to determine which devices have been used so that they can be charged/reimbursed for), and similar reporting activities without limitations.

Figure 14:
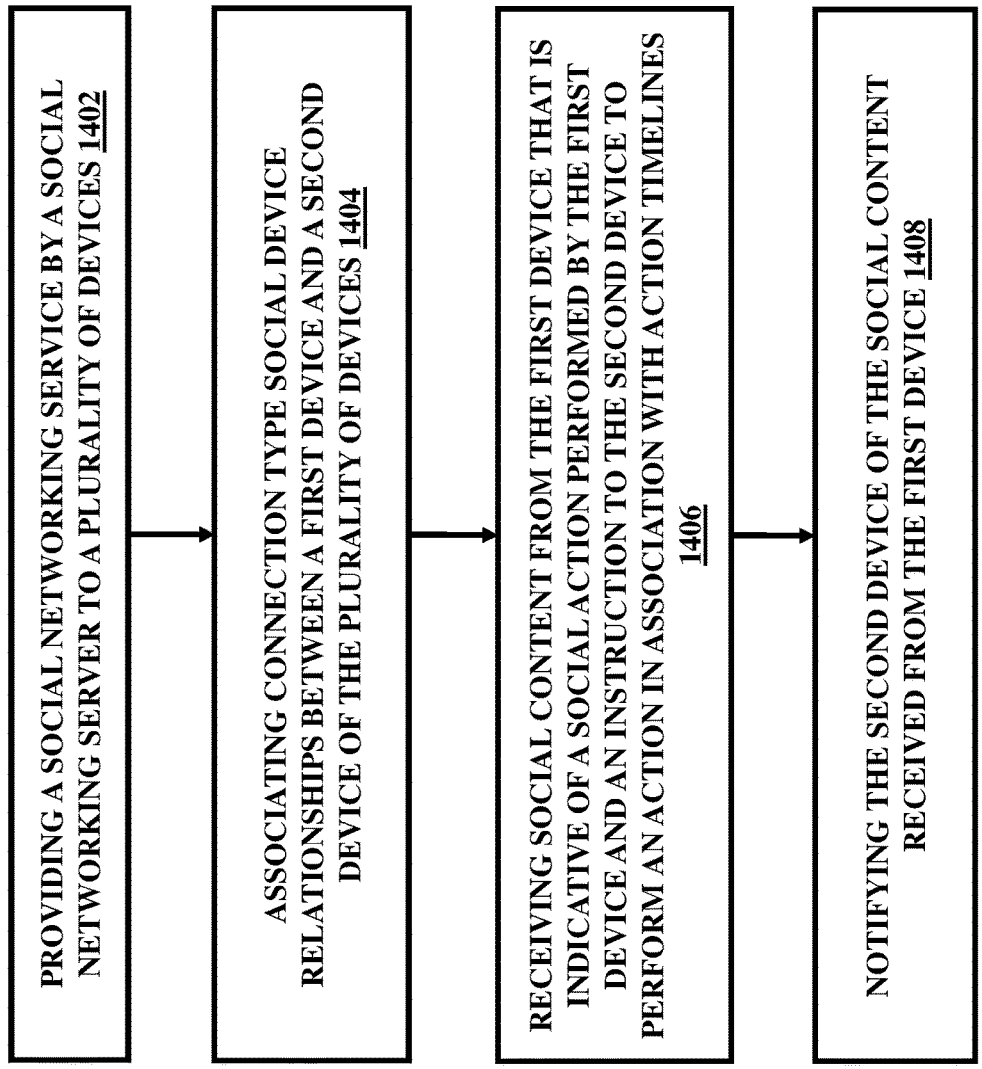
FIG. 14 illustrates a method flowchart for facilitating sequential, synchronous and automatically coordinated operation of a plurality of devices through interactive elements involving a chain of tasks and the devices in accordance with an embodiment herein.

FIG. 14, with reference to FIGS. 1 through 13, illustrates a method flowchart for facilitating sequential, synchronous and automatically coordinated operation of the plurality of devices 108 through interactive elements involving a chain of tasks and devices 108. At step 1402, the method comprises providing the social networking service by the social networking server 202 to the plurality of devices 108 so that each of the plurality of devices 108 are connected to the social networking server 202 by associating respective social profiles with the social networking server 202. The respective social profiles are social representations of the devices 108 and the social networking server 202 is programmed to allow the devices 108 to coordinate for a synchronous social times-based functioning. At step 1404, the method comprises associating connection type social device relationships between a first device 108a and a second device 108b of the plurality of devices 108. The connection type social device relationships allow the first and second devices 108a and 108b to view each other's social profiles through a device user interface enabled by the server 202. At step 1406, the method further comprises receiving social content from the first device 108a that is indicative of a social action performed by the first device 108a and an instruction to the second device 108b to perform an action in association with action timelines. The action timelines are indicative of time points associated with the action and define time when actual action should occur at the device 108b. At step 1408, the method comprises notifying the second device 108b of the social content received from the first device 108a. The social content includes the instruction to the second device 108b to perform the action in association with the action timelines.

The method may further include generating the social map indicative of devices and profile relationships among the devices 108. The method may further include storing the social map by the social networking server 202 so as to retrieve information from the social map to generate social proximity data, social status data, and use the social proximity and social status data to define precedence for the chain of tasks associated with the devices 108 for synchronous and coordinated functioning through the social networking platform 106. For example, based on the information extracted from the social map, the server 202 may be programmed to identify which devices are proximately located and which devices are remotely located relatively and also associate this information with location of a patient, capability of devices such as remotely accessible or not, patient requirement such as emergency or delayed service needed by the patient, and the like and accordingly decide the order or sequence of various tasks to complete a patient treatment procedure involving the several devices.

Figure 15:
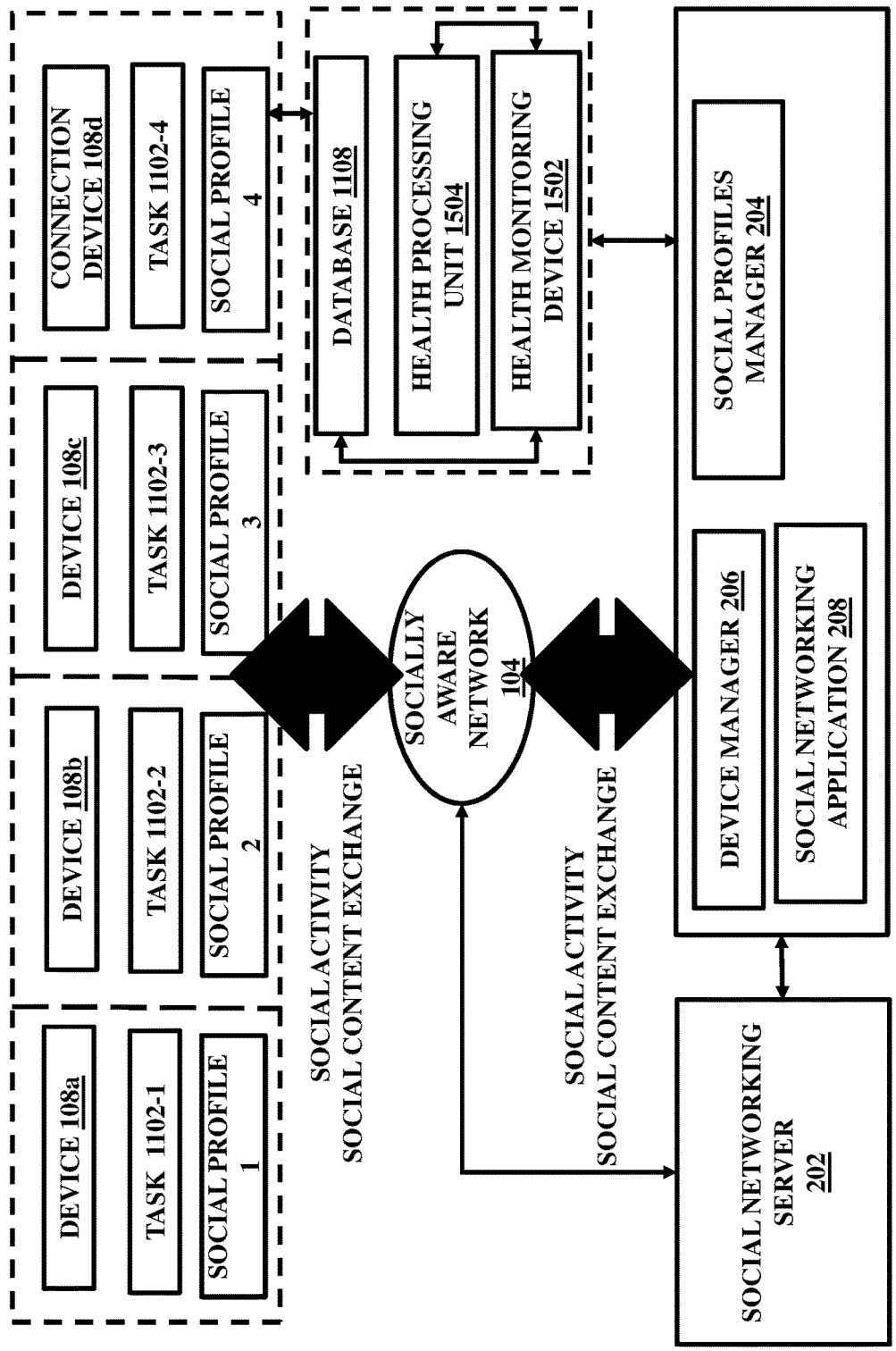
FIG. 15 illustrates interconnection of tasks and devices and their interaction with a social networking server, in an embodiment herein.

FIG. 15, with reference to FIGS. 1 through 14, shows the first device 108a, the second device 108b, the third device 108c, and the fourth device 108d which perform the first task 1002-1, second task 1002-2, third task 1002-3, and the fourth task 1002-4 respectively. The devices 108 are identified through their respective social profiles as shown in the figure. The interactive chain of elements includes the social profiles, tasks 1002, and devices 108 as shown in the figure.

The social networking server 202 provides a social networking health service to the plurality of devices 108 so that each of the plurality of devices 108 are connected to the social networking health service by associating the respective social profiles with the social networking server 202. The respective social profiles are social representation of the devices 108. The social profiles include various profiles as discussed earlier. In addition, the social profile discussed herein also includes a social health profile and a specification profile. The social health profile is indicative of health disciplines and instantaneous health characteristics of a device 108a which are updated in real time. The specification profile is indicative of health standards which are defined for specific devices based on information contained in other profiles such as installation profile, operation profile, manufacturing profile and the like. The specification profile identifies guidelines, manuals and standard operating characteristics of the device 108a. While the specification profile represents standard procedures and characteristics of the device 108a, the health profile represents current characteristics of the device 108a which may or may not be similar to the specification profile.

The social networking server 202 provides the social networking-based health service to the plurality of devices 108 and allows them to perform the series of social health tasks by exchange of social content in the socially aware network 104. The social networking server 202 is programmed to create and manage the individual centric profiles of the devices 108 that are social representation of the individual devices 108 within the socially aware network 104. The devices 108 are identifiable by other devices and the social networking server 202 through their social profiles. The social profiles of each device includes the health profile indicative of health disciplines corresponding to the device 108a and specification profile that includes details corresponding to predefined working parameters of the device 108a. The server 202 is further programmed to associate device social relationships in the socially aware network 104. Several types of relationships may exist based on various device characteristics and parameters which have been discussed earlier. In some examples for the various embodiments herein, the relationships may include connection relationships, wherein the connection relationships are indicative of the type of association between two or more devices in the network 104. The association may identify whether the two or more devices are mutual connections or not. The server 202 is programmed to receive updates pertaining to health profile and specification profile of a device such as 108a through a social activity involving social content exchange between the device 108a and the server 202. The updates may be received when there is any change in the health or specification parameters of the device 108a. In some examples, the device 108a may be provided to be used for a limited number of times or may be required to be disposed after merely a single use. In such cases, the specification parameters changes and the specification profile is updated after every use to indicate the current specification of the device 108a. The health parameters may not always remain the same. For example, the health parameters may not remain the same for a long time and the performance of the device 108a that is indicative of health status may change over time. This results in a change in the health profile of the device 108a. As long as the health profile conforms to the requirements as defined by the specification profile, the device 108a may be considered healthy. On the contrary, if the health profile is indicative of health disciplines deviating from the specifications as mentioned in the specification profile, the device 108a may be considered as faulty. The server 202 may be programmed to associate a relationship between the specification profile of the device 108a and its health profile, wherein a mismatch between one or more parameters of the health profile and the specification profile represents a fault in the device 108a. The server 202 may further be programmed to identify a connection device to alternatively perform a function of the faulty device such that the connection device is in an idle state for a time period during which the connection device is required to alternatively perform the function.

The social networking server 202 further comprises the social networking application 208 including a cluster of social applications each for providing a specific health facility to contribute health related social activity among the devices through the socially aware network 104. In an example, at least one of the plurality of devices is incapable of computation capabilities at least partially. The device 108a may be connected with an external controller such as 602a through the Near Field Communication (NFC) channel 604 so that the communication point 606a of the NFC channel 604 receives the social content from the device 108a and transfers the social content to the external controller 602a. The socially aware network 104 then allows health information sharing between the external controller 602a and the social networking server 202 in real-time.

The device 108a is coupled to an intelligent health monitoring unit 1502 for monitoring health profile or specification profile updates. The device 108a is communicatively coupled to the database 1108 for storing the health profile and the specification profile and information pertinent to various updates corresponding to the specification profile and the health profile. The health profile and the specification profile and the updates are shared by the health monitoring unit 1502 through the social activity involving social content exchange between the health monitoring unit 1502 and the social networking server 202. The monitoring unit 1502 is further coupled to a health processing unit 1504 for processing the health profile and the specification profile information to identify if the device 108a is faulty or not.

The health monitoring unit 1502 is integrally included within each of the plurality of devices 108 so that the devices 108 are capable of detecting a fault by comparing respective health and the specification profiles themselves with the use of the processing unit 1504. The social activity from the devices 108 involves a request to a set of connection devices to alternatively contribute in performing a function healthily when the connection devices are in idle state and when the device is faulty. The social activity can involve sending out a connection invitation to the social networking server 202 for identification and searching of specific devices profiles. The social networking server 202 is coupled to a search interface implementing a search algorithm for identifying and short listing the defined profiles. The shortlisted profiles are submitted to the device 108a so that the device 108a further performs a second social activity to send out connection requests to each of the shortlisted devices for extending the social network 104. By performing the second social activity the device 108a may for example request its connection device to perform a task on its behalf for a time the device 108a is in faulty state.

In some embodiments, the device 108a uses a second device 108b from among the shortlisted profiles as a health monitoring unit 1502 based on proximity and similarity in operation of the second device 108b with respect to the device 108a so that in case of a fault with or failure of the device 108a, the second device 108b performs functions of the device 108a voluntarily or upon a social activity initiated by the device 108a and directed to the second device 108b. The second device 108b may employ sensing units for monitoring environment of the first device 108a so as to ensure proper functioning of the first device 108a failing which the second device 108b may responsibly begin tasks performed by the first device 108a as a patient treatment procedure.

Figure 16:
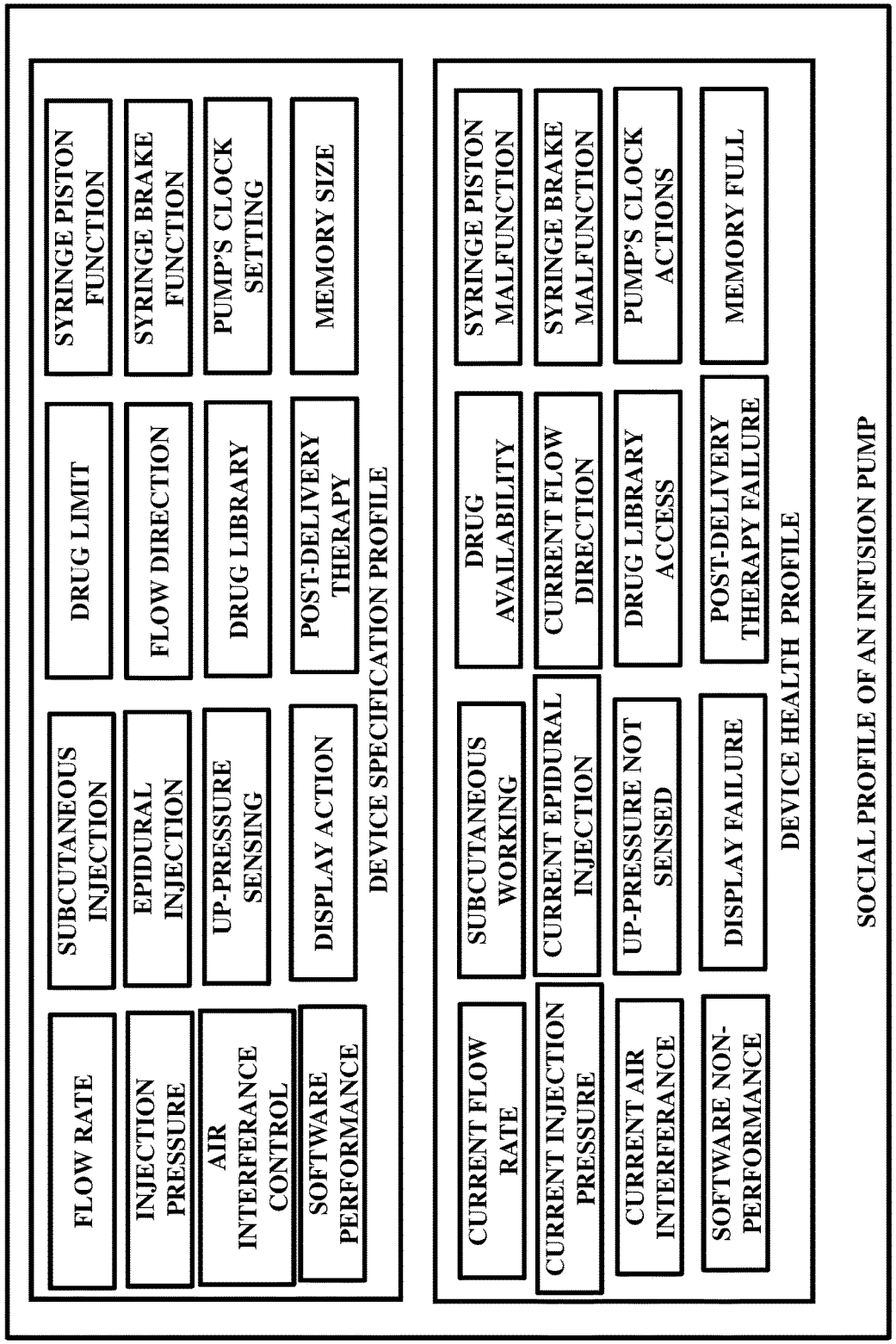
FIG. 16 illustrates an exemplary social profile depicting social health profile and social specification profile of an exemplary infusion pump in accordance with an embodiment herein.
Figure 17:
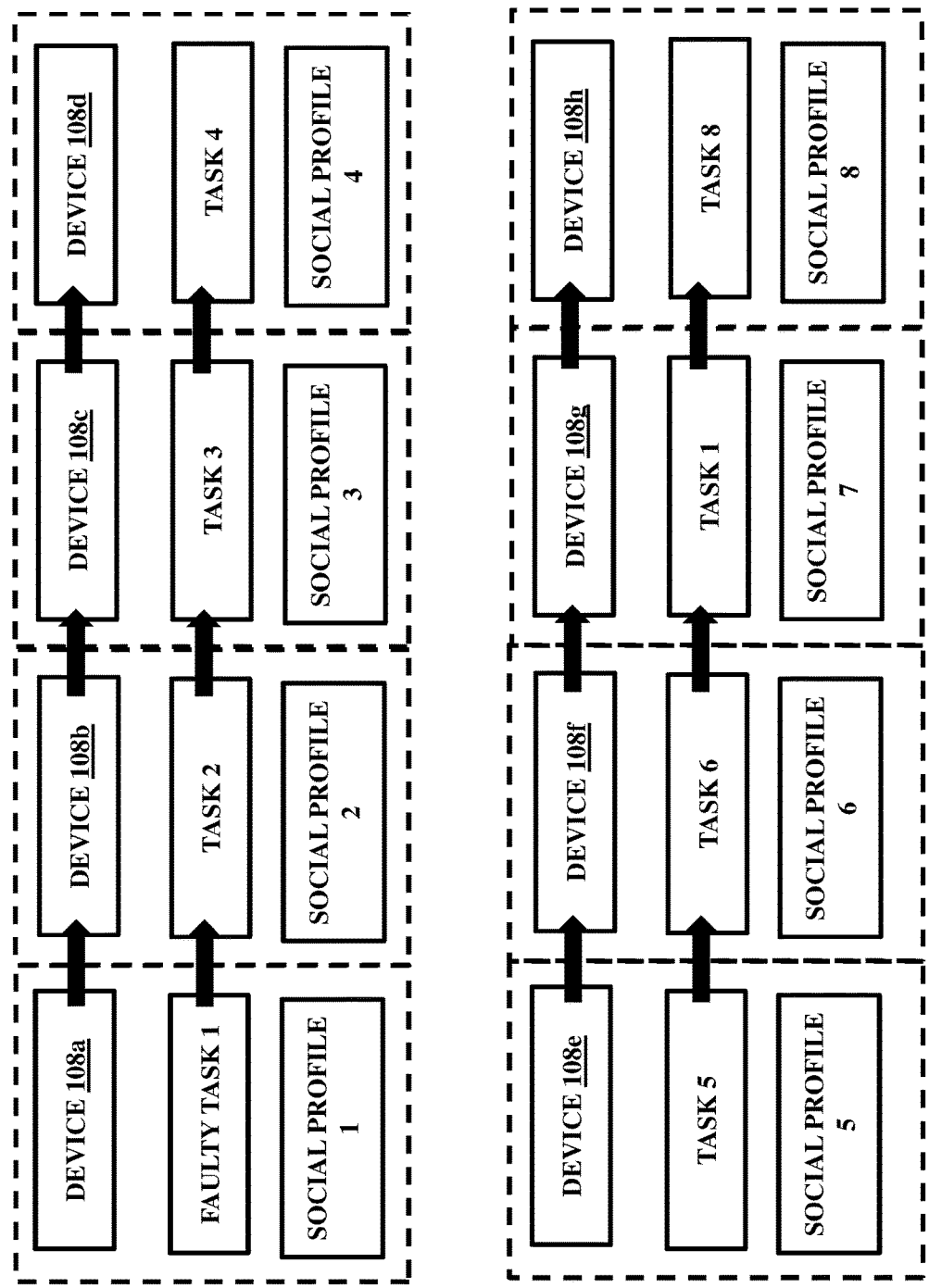
FIG. 17 illustrates another embodiment of an ecosystem of devices and respective tasks and social profiles interconnected through a social platform implemented by a social networking server for the purpose of health management of the devices, in an embodiment herein.

FIG. 16, with reference to FIGS. 1 through 15, illustrates an exemplary social profile depicting the social health profile and the social specification profile of an exemplary infusion pump. As shown, the social health profile may include information such as without limitations:
Flow Rate
Injection Pressure
Air Interference Control
Software performance of the infusion pump
Subcutaneous Injection
Epidural Injection
Up-Pressure Sensing
Display Action on a display unit of the device
Drug Limit
Flow Direction
Drug Library
Post Delivery Therapy
Syringe Piston Function
Syringe Brake Function
Pump's Clock Setting
Memory Size The social specification profile may include information such as without limitations:
Current Flow Rate
Current Injection Pressure
Current Air Interference
Software non-performance
Subcutaneous working
Current Epidural Injection
Up-pressure not sensed
Display Failure
Drug Availability
Current Flow Direction
Drug Library Access
Post-delivery Therapy Failure
Syringe Piston Malfunction
Syringe Brake Malfunction
Pump's Clock Actions
Memory Full/Usage FIG. 17, with reference to FIGS. 1 through 16, illustrates another embodiment of an ecosystem of the devices 108 and respective tasks and social profiles interconnected through the social platform 106 implemented by the social networking server 202 for the purpose of health management of the devices 108. The ecosystem includes four additional devices—device 108e, device, 108f, device 108g, and device 108h to perform task 1002-5, task 1002-6, task 1002-1, and task 1002-8 respectively and with associated social profiles as shown. The device 108e is associated with a social profile 5, device 6 is associated with a social profile 6, device 7 is associated with a social profile 7, and the device 8 is associated with a social profile 8.

The devices 108a, 108b, 108c, and 108d and the respective tasks form part of a first chain of tasks and devices sequenced to perform a first treatment procedure for a first patient in a defined structured and sequenced manner. The device 108e, 108f, 108g, and 108h and the respective tasks form part of a second chain of tasks and devices sequenced to perform a second treatment procedure for a second patient in a defined structured and sequenced manner. However, based on mutual relationships and connections, the devices 108 in the first chain and the second chain may interact through a social activity facilitated by the programmed server 202.

Figure 18:
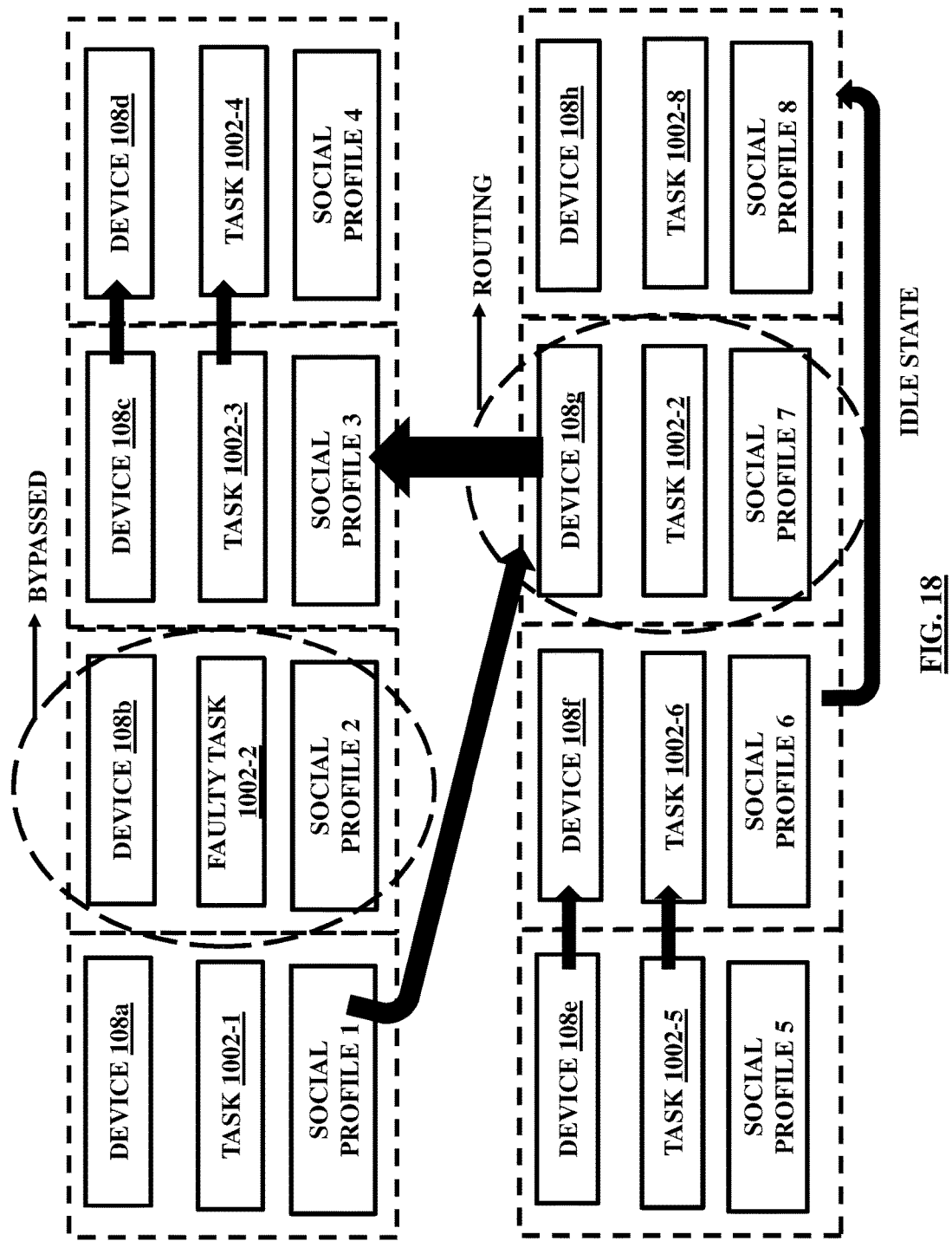
FIG. 18 illustrates the ecosystem of FIG. 17 with alternative devices interconnected and bypassing faulty devices, in an embodiment herein.

In some embodiments, as shown in FIG. 18, with reference to FIGS. 1 through 17, the devices 108b and 108g are mutual connections. As a result, the devices 108b and 108g can mutually share social content by initiating a social activity through the server 202. For example, the device 108b may request the device 108g to perform task 1002-2 in case the device 108b is faulty as the device 108g is capable to perform the task 1002-2 which the device 108b is required to perform in the treatment procedure for the first patient. Consequently, the chain of tasks and devices alters once the device 108g accepts the request of the device 108b and confirms to perform the task 1002-2. As shown, the treatment procedure now involves different devices bypassing the faulty device 108b. The new chain of task and devices for the treatment procedure for the first patient are device 108a and task 1002-1, device 108g and task 1002-2, device 108c and task 1002-3, and finally device 108d and task 1002-4. On the other hand, the second chain of devices and tasks for the treatment procedure of the second patient involves the devices 1008e and task 1002-5, device 108f and task 1002-6, device 108h and task 1002-8 with no involvement of the device 108g. This may be possible only when the device 108g and task 1002-2 are not required in the second chain of devices and tasks at least for the time the first chain bypasses the device 108b or the treatment procedure 1 is more critical than and holds priority over the second treatment procedure. Therefore, prior to cross-interconnecting between different chains, the device 108b determine whether the device 108g is in idle state for the time the device 108b is bypassed or may request a non-device coordinator to intervene for deciding a priority chain and priority treatment procedure and accordingly switch the device to the first chain or let it continue to perform the task 2 in the second chain of the devices for delivering the second treatment procedure.

Figure 19:
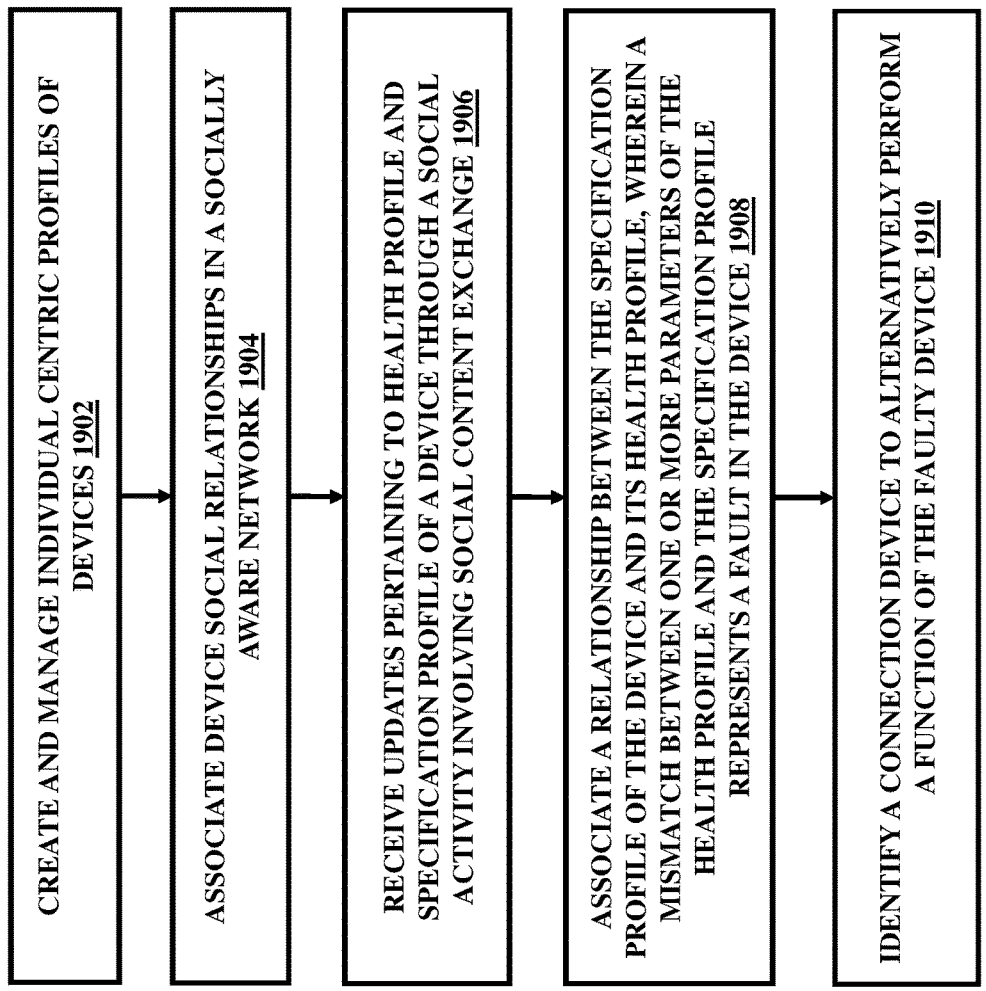
FIG. 19 illustrates a method flowchart for health management of a device interconnected with a plurality of devices through a social networking server in accordance with an embodiment herein.

FIG. 19, with reference to FIGS. 1 through 18, illustrates a method flowchart for health management of the device 108a interconnected with a plurality of devices 108 through the social networking server 202. The method comprises, at step 1902, creating and managing individual centric profiles of the devices 108 that are social representation of the individual devices 108 within the socially aware network 104. The devices 108 are identifiable by other devices and the social networking server 202 through their social profiles. The social profiles of each device such as 108a includes a health profile indicative of health disciplines corresponding to the device 108a and specification profile that includes details corresponding to predefined working parameters of the device 108a. At step 1904, the method further comprises associating device social relationships in the socially aware network 104. At step 1906, the method comprises receiving updates pertaining to health profile and specification profile of the device 108a through a social activity involving social content exchange between the first device 108a and the server 202. At step 1908, the method comprises associating a relationship between the specification profile of the device 108a and its health profile. A mismatch between one or more parameters of the health profile and the specification profile represents a fault in the device 108a. At step 1910, the method comprises identifying a connection device to alternatively perform a function of the faulty device such that the connection device is in idle state for a time period during which the connection device is required to alternatively perform the function.

In some examples, the method may also include informing the device 108a about the connection device that can perform the function in case of faults with the device 108a, wherein the information includes a social profile of the connection device. The method may include sending out a request by the device 108a to the connection device for alternatively performing the faulty function of the device 108a. The method may also include sending out a remote message by the device 108a to the connection device through a social activity initiated by the device 108a, wherein the remote message automatically triggers the connection device to perform the alternative function at a specified social event timeline occurrence. The method may include sending out an auto-correction message to the device 108a by the health monitoring device or the second device to trigger a fault management operation for rectifying the fault of device.

Figure 20:
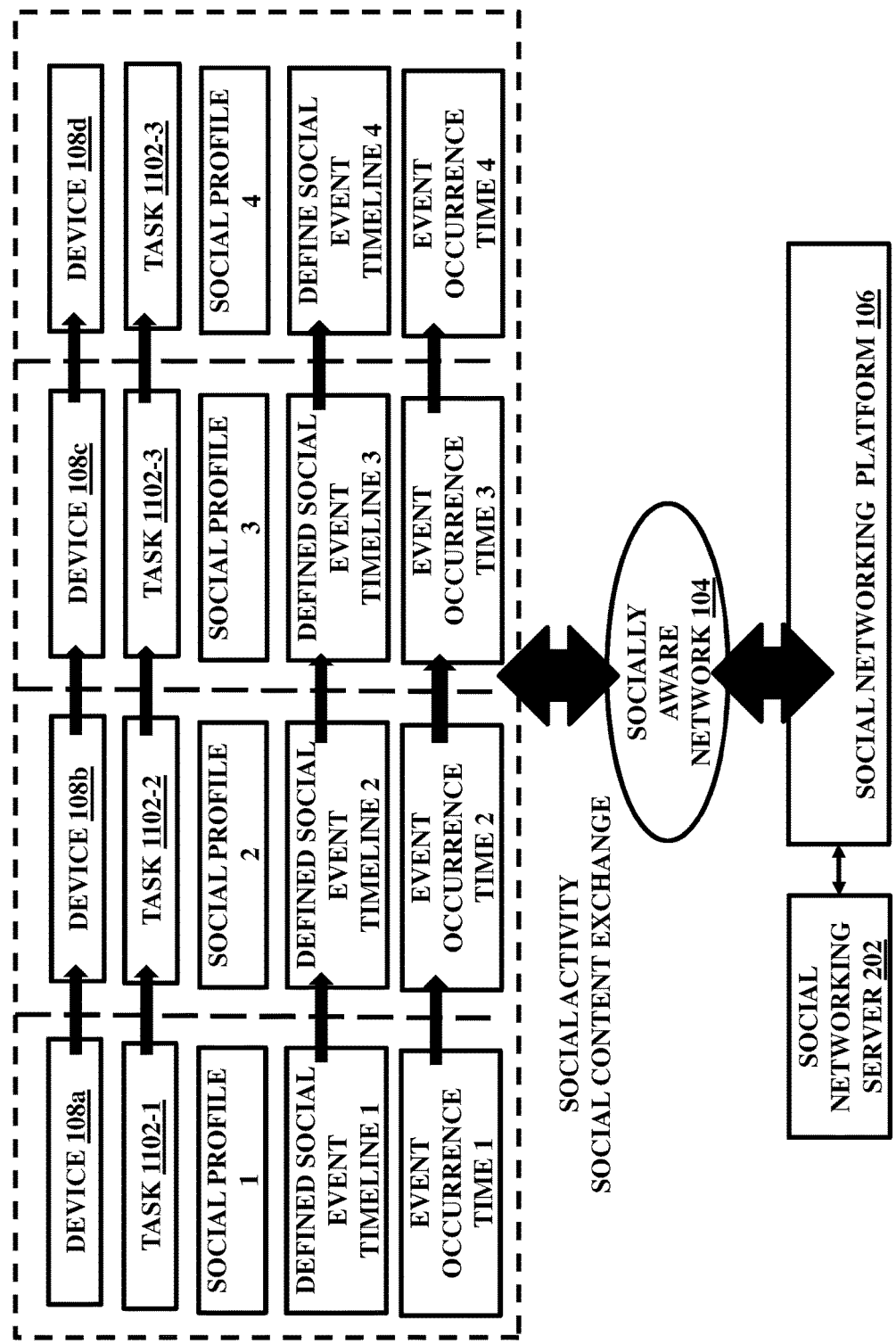
FIG. 20 illustrates an interconnection of the devices through a chain of tasks and devices in an embodiment herein.

FIG. 20, with reference to FIGS. 1 through 19, illustrates an interconnection of the devices 108a-108d through a chain of tasks and devices 108a-108d in an embodiment herein. As shown in FIG. 20, each of the devices 108a, 108b, 108c, and 108d are connected with the social networking server 202 that facilitates interconnection among the connection devices 102a-102d. The four devices 102a-102d, as shown, are connection devices and subscribe with the social networking server 202. The server 202 identifies specific tasks performed by the devices 102a-102d during a patient treatment procedure in an example. Further, the server 202 identifies, from the social profiles of the devices 102a-102d, defined social event timeline that define specific times when tasks 1102-1 to 1102-4 are performed by each of the devices 102a-102d. For example, defined social event timeline 1 defines that the device 108a should perform the task 1102-1 at the timeline 1. Similarly, the second device 108b performs the task 1102-2 at the social event timeline 2. The third device 108c performs the task 1102-3 at the social event timeline 3 and the device 108d performs the task 1102-4 at the social event timeline 4.

In practice, however, all the tasks 1102-1102-4 may not occur at the defined timelines. For example, actual time of performance of the task 1102-2 is event occurrence time 1, actual time of performance of task 1102-2 is event occurrence time 2, actual time of performance of task 1102-3 is event occurrence time 3, and actual time of performance of task 1102-4 is actual event occurrence time 4. The actual event occurrence times may or may not match the defined social timelines. In case, there is any difference between the actual event occurrence times and defined social timelines beyond a threshold, a fault may be identified and accordingly the devices 108a-108d may communicate one another through the social networking server 202. The devices 108a-108d may also loop in alternative devices for performance of the faulty tasks by requesting the social networking server 202 for identifying social connections who may perform the faulty tasks.

Figure 21:
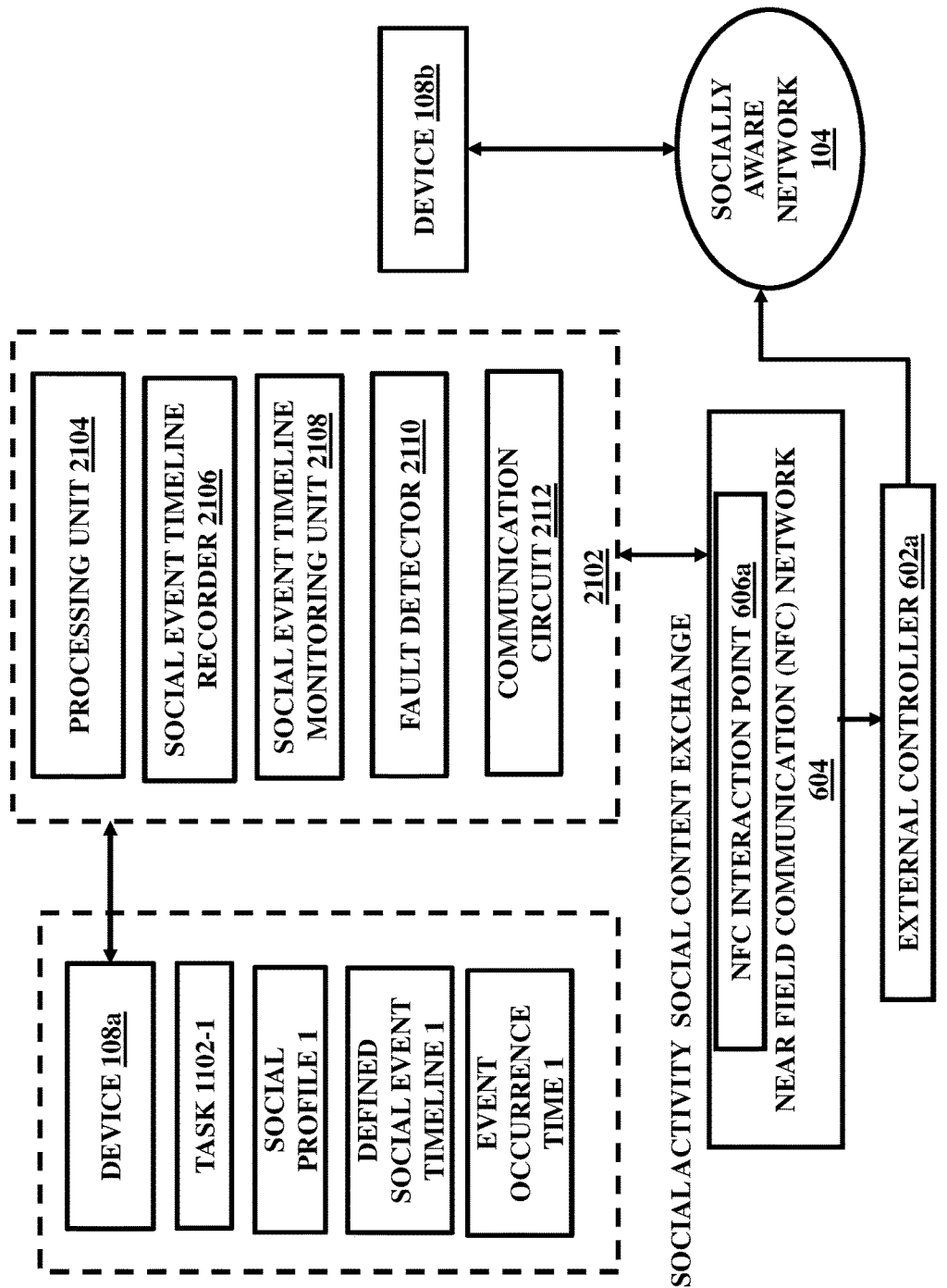
FIG. 21 illustrates a system coupled communicatively to or included in a device for allowing the device to communicate with a social networking server in accordance with an embodiment herein.

FIG. 21, with reference to FIGS. 1 through 20, illustrates a system 2102 coupled communicatively to or included in a device such as the device 108a for allowing the device 108a to communicate with the social networking server 202. The system 2102 facilitates monitoring and conveying of health related information from the first device 108a to a second device such as the device 108b interconnected through the socially aware network 104 and the server 202.

The system 2102 includes a processing unit/circuit 2104, a social event timeline recorder 2106, social event timeline monitoring unit 2108, fault detector 2110, and a communication circuit 2112. The social event timeline recorder 2106 stores information pertinent to when an event should occur at the first device 108a, wherein the event should occur at the defined social timeline 1. The social event timeline monitoring unit 2108 monitors event occurrence time for the social event. The fault detector compares the social event timeline with the event occurrence time for the event. A gap between the social event timeline and the event occurrence time beyond a threshold limit is indicative of a fault. The events at the first device 108a and at the second device 108b are interdependent. The communication circuit 2112 allows sharing of a social content, indicative of the fault and a predicted modified event occurrence time at the first device 108a, to the social networking server 202 through a two-way communication channel including the near field communication channel 602a and the socially aware network channel 104. The social networking server 202 sends the social content to the second device 108b. The first device 108a and the second device 108b are connections and parts of same chain of integrated tasks. The processing unit 2104 may process output from the social event timeline recorder 2106, social event timeline monitoring unit 2108 and fault detector 2110 and generate a signal indicative of the predicted modified event occurrence time. The defined social timelines of other devices may accordingly be calculated and updated based on updates in the occurrence times of the event at the device 108a. In an embodiment, the processing unit 2104, social event timeline recorder 2106, social event timeline monitoring unit 2108, and the fault detector 2110 may be integrated within the health processing unit 1504 and health monitoring unit 1502 of FIG. 15 for purposes of health management of the devices 108 with the use of the social networking server 202 and the social networking platform 106.

The embodiments herein also provide a method for monitoring and conveying health related information from the first device 108a to the second device 108b interconnected through the socially aware network 104. The method comprises storing information related to the defined social even timelines for the task 1102-1 associated with the first device 108a and the social event timelines defining times when an event should occur at the first device 108a. The method further comprises monitoring the social event occurrence time by the social event timeline monitoring unit 2108. The method further comprises detecting a fault in functioning of the first device 108a by comparing the social event timeline with the event occurrence time for the event, wherein a gap between the social event timeline and the event occurrence time beyond a threshold limit is indicative of the fault. The event at the first device 108a and the event at the second device 108b are interdependent. The method further comprises sharing the social content, indicative of the fault and the predicted modified event occurrence time at the first device 108a, to the social networking server 202 through the two-way communication channel. The social networking server 202 sends the social content to the second device 108b.

An embodiment herein provides a facility for integration of the devices 108 through the social networking platform 106 or the social networking server 202. An embodiment herein provides a facility for automation in devices networking and interaction. An embodiment herein provides a facility for automation in networking and interaction of the devices 108 in a medical or other high-reliability, high security environment by integrating them through the devices-based social networking platform 106 for effective and automated patient care. An embodiment herein provides a facility for creation of devices profiles over a social networking interface by the social networking server 202. An embodiment herein provides a facility for creation of devices profiles over a social networking interface for their integration through the social networking server 202. An embodiment herein provides a facility for creation of devices profiles over a social networking interface for automation in networking and interaction of the devices 108.

An embodiment herein provides a facility for creation of the devices profiles over a social networking interface to exchange information through the networking interface for their health monitoring. An embodiment herein provides a facility for health monitoring of the devices 108 by exchange of information through the networking server 202. An embodiment herein provides a facility for health monitoring of the devices 108 by exchange of information through a networking interface that is formed by deploying the social networking platform 106 for the devices 108 so that fault monitoring and management of the devices 108 can be done in real-time. An embodiment herein provides a facility for health monitoring of the devices 108 by exchange of information through a networking interface among the devices 108 whose networking and interaction is automated. An embodiment herein provides a facility for creation of the devices profiles over a social networking interface to exchange information through the networking server 202 for their health monitoring.

An embodiment herein provides a facility for searching, identifying and presenting related information and device profiles to a second device in response to a request submitted by a first device to make the device responsible for monitoring health parameters of the related devices based on similar operation characteristics of the two devices. An embodiment herein provides the server 202 that is programmed to facilitate a chat room-type setting of conversation among the devices 108. The chat room-type setting of conversation among the devices 108 may be facilitated by integrating the devices 108 through the social networking server 202 for enabling the social networking service among the devices 108, wherein the devices 108 are able to exchange social content through the chat room-type setting. In an embodiment, the window provides a facility for the devices 108 to chat with like-minded devices in a specific group. For example, a room may be dedicated for pacemakers only so that by entering the room, a device may directly communicate with other pacemakers that are interconnected with the server and associated with the room. The server 202 facilitates networking and interaction by using the chat room-type setting of conversation among the devices 108 for information exchange.

In an embodiment, the chat room-type setting may facilitate creation of separate profiles by the devices 108 over the social networking platform 106 dedicated to the devices 108 for allowing them to associate with a particular room and communicate through the chat room-type setting of conversation among the devices 108 within the room. The profiles are used as identifiers and gateways for the specific chat rooms. In an embodiment, health related information of the devices 108 may be communicated by exchange of information through the networking service among the devices 108 using the chat room-type setting of conversation and accordingly preventing damages associated with potential faults due to erroneous working of the devices 108. For example, the devices 108 can receive notifications pertinent to faults through the chat room setting and automatically triggering another alternative device configured to do the same function in the same room for managing device tasks alternatively. In an example, the chat room setting may automatically trigger an alternative device by sending a notification that include programs to initiate a request for switching on functioning of the alternative device in association with the profile of the faulty device and patient associated with the faulty device. In an embodiment, the server 202 configures the chat room-type setting of conversation among related devices bearing related devices-based profiles based on searching, identifying and retrieving related information and devices profiles in response to a request submitted by the device.

In an example, the server 202 is programmed to generate the social map/graph depiction for structuring and analysis of the devices 108 and edges (indicating relationship). In an example, the server 202 is programmed for social map/graph depiction for structuring and analysis of the devices 108 and edges (indicating relationship) that are integrated through the social networking server 202. An embodiment herein, in an example, facilitates automation in the devices networking and interaction by using an analytical framework of the social map/graph depiction for structuring and analysis of the devices 108 and edges (indicating relationship) that are integrated through the social networking server 202. The server 202 allows updating of the social map/graph depiction for structuring and analysis of the devices 108 and edges (indicating relationship) based on information searched and identified for related devices presented in response to a request submitted by the device such as 108*a*. The updated graph may depict added relationships.

In an example, the server 202 is programmed to create and update the social profiles of the devices 108 automatically based on information collected from the social map/graph for structuring and analysis of the devices 108 and edges (indicating relationships). In an example, an embodiment herein facilitates health monitoring of the devices 108 and controlling faults in operational performances by forecasting faults and scheduling alternative operations using alternative devices as identified based on the social map/graph used for structuring and analysis of devices 108 and edges (indicating relationships). The alternative devices may be identified for example based on proximity information from the social map, and the like.

In an example, the server 202 is programmed for algorithm based classification and search of trending activities and computation of weight associated with each activity/post for trending rate. For example, the server 202 may identify trending social activities by monitoring the devices social posts and social content exchange and accordingly may tag certain activities that are trending at a particular point of time and are most frequently performed by the devices 108. The server 202 may associate a weight to an activity that defines its trending rate. For example, an exchange of social content between a heart beat monitor and a ventilator to request initiation of ventilation process for a patient may be too frequent in a particular medical environment which may be indicative that the ventilators are in high demand. Therefore, the computed weights that define trending rate may allow medical professionals to mange and deploy the devices 108 accordingly based on the social activities trending rate. In an example, the algorithm-based classification and search of trending activities and computation of weight associated with each activity/post for the trending rate by analyzing information and posts exchanged among the devices 108 is performed for the devices 108 that are integrated through the social networking server 202 over the social network 104. This allows automation in the devices networking and interaction by using the information obtained from algorithm based classification and search of trending activities that occur among the devices 108. In an example, the algorithm-based classification and search of trending activities and computation of weights associated with each activity/post for the trending rate is performed by using the information exchanged by the devices 108 through the chat room-type setting of conversation among the devices 108. In an example, the server 202 may facilitate algorithm-based classification and search of trending activities and searching, identifying and presenting information and device profiles to a device such as 108*a* in response to a request submitted by the device 108*a* so that the related device exhibits trending behavior. The embodiments herein allow computation and searching for trending profiles and accordingly presenting trending profiles to the device 108*a* for extending network. The trending profiles in an example may be the profiles of the devices 108 that show or perform trending activities or exchange trending social content. In an example, the trending behavior of a device such as 108*a* may represent a behavior which involves communicating with trending devices and exchange trending social content. This may allow facilitating actions performed by the devices 108 based on what is most desired in a medical or any other environment and accordingly prioritizing the devices networking and tasks. In an embodiment, the prioritization and the trending behavior may be controlled by human coordinators so as to allow the interconnected network to function in the most optimal manner and utilize the devices 108 and tasks and interconnections in the most efficient manner. In an example, the server 202 may be programmed to create the devices profiles and associate profiles-based trending activities by using an algorithm-based classification and search of trending activities for identifying devices behavior in association with profiles types for facilitating network extension toward profiles with a surge of trending activities.

In an example, an embodiment herein facilitates health monitoring of the devices by exchange of information through the social networking server 202 and identifying trending health problems among the devices 108 by using the algorithm-based classification and search of trending activities related to health status and by computation of weights associated with each post/activity for trending rate so as to develop fault management and health plans for the devices 108 in a critical medical environment for the most dangerous and most trending faults, wherein the trending faults are identified based on the trending information pertinent to social content that is indicative of faults during health information exchange.

In an example, the server 202 is programmed to facilitate searching, identifying and presenting related information and device profiles to a device such as 108*a* in response to a request submitted by the device 108*a*. The searching, identifying, and presenting of the related information and device profiles to the device 108*a* in response to the request submitted by the device 108*a* is performed in an environment that includes a plurality of integrated devices 108 that are interconnected through the social networking server 202. In an example, the server 202 may be programmed for submitting invitations to a related device upon receiving related information and device profiles for extending social network among the integrated devices 108. In an example, the server 202 may be programmed for searching, identifying and presenting related information and device profiles to a device such as 108*a* in response to a request submitted by the device 108*a* for automating devices networking and interaction. In an example, the server 202 may be programmed for creation of the devices profiles and allowing searching, identifying and presenting related information and device profiles to the device 108*a* in response to the request submitted by the device 108*a*.

In an example, an embodiment herein provides a server 202 that is programmed for facilitating sequential, synchronous and automated operation of several integrated devices 108 via interactive elements through a chain of tasks and devices 108. In an example, an embodiment herein provides a server 202 that is preprogrammed for sequential, synchronous and automated operation of the several devices 108 via interactive elements through the chain of tasks and devices 108 that are integrated through the social network 104. The server 202 facilitates healthcare automation among the plurality of medical devices 108 by using the sequential, synchronous and automated operation of the several integrated devices 108 via the interactive elements through the chain of tasks and devices 108. In an example, the server 202 allows creation of devices profiles over the social networking server 202 and facilitate sequential, synchronous and automated operation of the several integrated devices 108 via the interactive elements by associating the profiles to the operating devices 108 and controlling operations based on respective profiles of the devices 108, wherein the profiles can be a manufacturing profile, an installation profile or an operation profile of a device such as 108a or any other type of profile as discussed earlier. The server 202 allows health monitoring of the integrated devices 108, exhibiting a sequential, synchronous and automated operation via the interactive elements through the chain of tasks and devices 108, by exchange of information through the networking server 202.

The server 202 is programmed to provide an analytical framework for sequential, synchronous and automated operation of the several integrated devices 108 via the interactive elements through the chain of tasks and devices 108 by employing the social map/graph depiction for structuring and analysis of the devices 108 and edges (indicating relationship).

The server 202 is programmed to perform searching, identifying and receiving related information and profiles of an adjacent device in a sequential, synchronous and automated operation in response to a request submitted by a device such as 108a for automatically coordinating the sequential tasks synchronously. In an example, social networking timelines are associated with events defining times when particular events occur at the devices 108. The social networking timelines associated with events defining times when particular events occurred at the devices 108 are recorded so as to integrate the devices 108 for events occurrences at regular recorded times through the social networking server 202. The server 202 facilitates automated networking and devices interaction by automatically triggering devices events based on determined social networking timelines associated with the events defining times when particular events should occur at the devices 108.

In an example, the server 202 is programmed to define profiles of the devices 108 so that the profiles include social networking timelines associated with events defining times particular events should occur at the devices 108, such that the profiles govern occurrences of events. The devices 108 that have adjacent occurrences of events may be classified in groups. An embodiment herein provides an automated tool for identifying social networking timelines associated with events defining times when particular events should occur at the devices 108 by analytically utilizing social map/graph depiction for structuring and analysis of the devices 108 and relationships with the use of analytical computation models, wherein each of the dimensions along edges are indicative of respective timelines between corresponding events occurring at respective devices 108 that form nodes connecting the edges.

In an example, an embodiment herein facilitates in defining social networking timelines associated with the events that define times when particular events occur at the devices 108 in a sequential, synchronous, and automated operation of several integrated devices 108 via interactive elements through a chain of tasks and devices 108 so as to synchronously manage the tasks precedence based on the defined social timelines. In an example, an embodiment herein facilitates healthy operation of sequential, synchronous and automated integrated devices 108 via interactive elements in a "chain of tasks and devices 108" by automatically managing objectionable interaction of the devices 108 thereby resulting in a trustworthy performance of the sequential and synchronous nature of the entire chain of tasks and devices 108. The social networking timelines are associated with events defining times when particular objectionable events occurred at devices and accordingly the server facilitates in preventing an impact of the objectionable events at other scheduled timelines by monitoring when would the affect of the objectionable event reach to other nodes or devices that share a timelines gap with the devices exhibiting the objectionable events.

In an example, an embodiment herein facilitates sequential, synchronous, and automated operation of several integrated devices 108 via interactive elements through a "chain of tasks and devices" by using a chat room-type setting for conversing among the devices 108 in real-time. A device such as 108a triggers operation of an interconnected device such as 108b by posting messages through the chat room setting so that the other device 108b sequentially operates after receiving commands from other devices proceeding in the chain.

In an example, the server 202 is programmed to facilitate prioritizing tasks in a sequential, synchronous and automated operation of several integrated devices 108 via interactive elements through a chain of tasks and devices 108 based on priority ratings of the devices 108 as decided analytically through an algorithm-based classification and search system for trending activities and computation of weights associated with each activity/post for trending rate indicative of priority ratings of the sequential tasks. The priority ratings define criticality and importance of a device such as 108a and respective tasks in the chain of devices 108 and tasks.

In an example, the server 202 facilitates health monitoring of the devices 108 by recording actual event occurrence times at a stage and comparing actual real time event occurrence times with predefined social networking timelines associated with events defining times when particular events should occur at the devices 108 in normal functioning, wherein a lag beyond a threshold value between the actual real time determined time values and the predefined time values is indicative of a fault and abnormal health. In an example, the social networking server 202 facilitates updating of the defined social networking timelines associated with events defining times when particular events should occur at the devices 108 in real time by exchange of information through a chat room-type setting of conversation among the devices 108 implemented through the social networking platform 106 for the devices 108. The updating of the timelines is needed for several reasons including in cases of malfunctioning of one or more devices and accordingly bypassing those devices or routing tasks through alternative devices capable of compensating for the malfunctioning devices.

In an example, the server 202 facilitates correlating devices that exhibit trending activities with social networking timelines associated with events defining times when particular events occur at corresponding devices that exhibit the trending activities for identifying 'trending times' that are indicative of times when trending activities would preferably occur so as to facilitate advanced monitoring of the trending activities based on forecasted times for occurrences of such trending activities. In an embodiment, the trending activities define critical activities performed by the devices, or important activities, or highest value activities by the devices.

In an example, the social networking server 202 facilitates searching, identifying, and receiving information and device profiles by a device such as 108a for specific devices that correspond to specific social networking timelines associated with events defining times when particular events occur at devices so that the specific timelines of the devices match with timelines for one or more malfunctioning devices in the social network 104 of the devices, and subsequently identifying whether one or more of these identified devices can perform and are capable of performing activities of the malfunctioning devices so as to replace the malfunctioning devices or activities with the devices and activities so identified that also inherently bears similar timelines occurrences and so prevent any unwanted affect in their synchronous operation with other devices.

In an example, the server 202 is programmed to automatically manage objectionable interaction of the devices 108. In an example, the server 202 is programmed for automatically managing objectionable interaction of the devices 108 that are integrated through the social aware network 104. In an example, the server 202 is programmed for automatically managing objectionable interaction of the devices 108 in an automation environment of the devices 108 facilitating an automated networking and interaction among the devices 108 using the social networking server 202. In an example, the server 202 is programmed for automatically managing objectionable interaction of the devices 108 by updating profiles of the devices over the social networking server 202 so that the updated profile conforms with the requirements and is no more objectionable and also storing information pertaining to the objectionable behavior and corresponding profiles in a database maintained by the social networking server 202. In an example, an embodiment herein facilitates health monitoring of the devices 108 by exchange of information through the social networking server 202 and blocking objectionable interaction of the devices 108 in the network 104 that do not fulfill required health criteria thereby preventing faults and critical situations from occurring in a medical environment beforehand. The server 202 is programmed to assess, and update social map/graph depiction for structuring and analysis of the devices 108 and edges (indicating relationship) based on detection of an objectionable behavior of a device such as 108a, wherein the updating may include redefining vertices and edges of the map that correspond to the devices 108 and various relationships among the devices 108.

In an example, the server 202 may be programmed to facilitate detection of an objectionable behavior of a device such as 108a by another device such as 108b and communicate information about the behavior to a social networking service manager or server 202 through a chat room-type setting in real-time so as to manage the objectionable behavior in real-time. In an embodiment, adjacent devices that are directly connected with a device such as 108a may detect the objectionable behavior the earliest and may communicate the information to the service manager or/and to other devices 108 that may be directly or critically affected by the objectionable behavior.

In an example, the server 202 is programmed for performing algorithm-based classification and searching of trends of objectionable behavior and objectionable interaction of the devices 108 and accordingly creating a fault management plan in advance. The plan may be used for prioritizing safety of those devices that exhibit trending activities, and for ensuring that monitoring of the objectionable behavior is based on the determined trending objectionable behavior. The objectionable behavior may be indicated in the form of an activity initiated either by the device exhibiting the objectionable behavior or by another integrated device that is influenced by the objectionable behavior of the other device. The activity that is indicative of the objectionable behavior is termed as 'objection identification activity'.

In an example, the server 202 is programmed for searching, identifying, and receiving related information and device profiles that show a typical defined objectionable behavior with other related devices for defined time duration in response to a request submitted by the device 108a. In an example, the server 202 facilitates searching, identifying, and receiving related information and device profiles that have not shown any objectionable behavior with other related devices for defined time duration in response to a request submitted by a device such as 108a. The time duration defined behavior that is free from any objection is indicative of a reliability and trustworthiness of a device so that the device can be used as an alternative in an environment of a plurality of devices 108 for efficient and reliable performance especially during a critical medical task or operation.

In accordance with some embodiments, the SNP 106 can be implemented with the use of various social application programming interfaces (APIs). In some embodiments, various statistical tools and protocols can be employed in the development of the SNP 106 so as to enable various statistical and analytical capabilities within the SNP 106.

In an embodiment, various medical devices or other devices 108 can be integrated through the social networking platform 106. The integrated devices 108 can share or exchange information, announce them publicly, represent themselves through their social profiles and can perform several other functions.

In an embodiment, the devices 108 can operate in the SNP network 104 with the use of limited manual intervention such as in case of a semi-automated architecture. The settings can be defined accordingly so as to define the nature and extent of automation.

In an embodiment, the devices 108 can operate over the SNP 106 in a completely automated fashion, wherein the devices 108 can be deployed with sensors, detectors, and other monitoring and regulating devices that may be capable of monitoring the performance of the devices 108 as and when needed or in real time. In an example embodiment, the sensors, detectors, and monitoring devices can be configured to be current based, pressure based, chemical composition based, location based, vibration based, light based, motion based, temperature based, physiological signal based, acoustic signal based, sound based, chemical compound or biomolecules interaction based, infrared sensor, electric current based, electric potential based, magnetic or radio based, environment based, weather based, moisture based, humidity based, flow based, fluid velocity based, ionizing radiation based, atomic particles detection based, navigation instruments, location based, position based, angle based, displacement based, distance based, speed based, and acceleration based, imaging based, photon based, and optic based, force based, density based, level based, thermal or heat based, proximity based, and presence based, and various other types of sensors and detectors based on various detection and sensing technologies. In addition, various other technologies such as RFID, bar code detection and the like can also be employed to enable a completely automated architecture of the SNP 104 for the devices interaction and integration.

In an embodiment, the devices 108 are capable of creating their profiles over the SNP 106. The profiles can be created automatically based on the information collected from the devices 108 or semi-automatically based on instructions from the devices 108 or manually based on instructions from an associated person that triggers the devices 108 to connect with the SNP 106 and create profiles. In an embodiment, the profiles can be created by uploading manuals and device related documents in a specific portal assigned to a device so that the server 202 can execute instructions based on a set of executable device-based custom templates to create custom profiles for specific types of devices.

In an embodiment, the SNP 106 can facilitate health monitoring of the integrated devices 108 over the SNP 106. For example, the member devices 108 of the SNP 106 can automatically share and update their performance related information on their profiles which can be regularly monitored by the server 202 or by a person associated with the devices 108. This may enable reporting of health related information of the devices 108 to respective entity such as a responsible person. Alternatively, a responsible person may also visit the profiles of respective devices over the SNP 106 and identify health breaks, if any, and can accordingly take steps.

In an embodiment, several devices 108 can further be facilitated with the use of a chat room type of window that can be visible on the website of the SNP 106. The devices 108 can read messages shared from their connections and also share information with them or respond to them through the same window. As discussed above, this interaction may also be partially automated, completely automated, or manually intervened and can employ technologies such as those discussed above.

In an embodiment, the relationships of the devices 108 may be represented with the use of the social graph as discussed earlier. The nodes may represent a complete web of the relationship and may be read and analyzed and interpreted manually by an external person associated with the devices 108 or by the devices 108 automatically. In some cases, special software and algorithms may be deployed to interpret the social map. The social map may assist the devices 108 to expand their connections, manage their connections, manage the information sources, and perform several other tasks.

In an embodiment, the devices 108 may exchange information among them and also search for tending topics and other posts on the SNP 106 posted by other devices 108. For example, each of the posts in the SNP 106 made by the devices 108 can be associated with a rating or relevancy factor based on one or more parameters. In particular, one important factor for identifying activities of the devices or posts posted from the devices is the determination of related posts that are most relevant to the activity of a device seeking for relevant activities and posts. Other parameters may include such things as the nature of the devices 108, geographic proximity, like-mindedness, social map or graph proximity along such as the edges as discussed above. Various mathematical and statistical tools may be implemented to identify the proximity along the edges in the social map with the use of software and hardware combinations. Other parameters may include such things as trendiness based on a universal rating such as provided by the SNP 106 or based on public viewing of the activity or the post by the devices 108. In an embodiment, the social networking platform 106 may present related posts to a device 108*a* such as, for example, a post determined to be a trending topic or a post to a device 108*a* that is in the geographic proximity.

In other embodiments, a device 108*a* may configure one or more settings or parameters to dictate when the social networking platform 106 should present related posts to the device 108*a*. In some cases, weights may be associated to the activities and posts and relevance of the activity or post may be determined based on the computed weights.

In an embodiment, a device 108*a* can query a database of profiles of the devices 108 such as of a community of the devices 108. The query can include such things as information pertinent to a device 108*a* such as including, without limitations, the name of the device 108*a*, identifier of the device 108*a*, type of the device 108*a*, medical conditions treated by the device 108*a*, therapies delivered by the device 108*a*, patient identifier associated with the device 108*a*, life style factors associated with a patient associated with the device 108*a*, environmental factors, contextual factors, historical records stored in the device 108*a*, and so on. Upon searching, the device 108*a* can view the matching profiles, connect with them, post message for them, like or dislike their posts, use their data upon request, share information with them, and perform further queries or refine the queries.

In an embodiment, the devices 108 that operate in a sequence can connect together on the SNP 106. The connected devices 108 can be programmed to operate according to decided and programmed settings in a sequence. Any information relevant from a previous stage by a device 108*a* in a next stage or in the same stage by any other device 108*b* may be shared through the SNP 108 which may be accessed by other devices 108 in the same or subsequent stages accordingly. Thus, several devices 108 that operate integrated can further be integrated through the SNP 106 and information sharing can happen in real time. Further, the data generated through integration of the devices 108 may be used to facilitate an integrated and multi-staged operation of other devices in a different location. The integrated operation of the devices 108 in such a manner with the use of the SNP 106 can for example be implemented in a connected dosing or diagnostic center or even in an assembly line of a manufacturing system without any limitations. Sensors and monitoring devices may be integrated in the devices 108 so as to collect relevant information from the devices 108. The stages and the status of the stages in which the devices 108 currently operate may be identified with the use of these and other such identification and sensing technologies.

In an embodiment, the SNP 108 can implement social networking timelines associated with events defining times when particular events occur in relation to the devices 108. This implementation approach can be integrated in architecture of several devices 108 integrated through the SNP 106 and working in any of a sequential, synchronous, and automated operation. For example, the timelines associated with occurrence of an event at a device 108*a* may govern the occurrence of another event at another device 108*b*. This may be controlled by tagging the devices 108 for particular events and then monitoring for the occurrence of the events and communicating to the connected devices 108 through the SNP 106. The timelines can be depicted with the use of a line or a scatter graph, for example, and visible over a display for use by a patient or a hospital or a physician or any other entity.

In an embodiment, the SNP 106 can manage objectionable behavior. For example, the SNP 106 can automatically manage objectionable interaction of the devices 108 such as from those that may not be required in a particular set of operations relevant in synchronous and coordinated functioning of a particular set of devices. Similarly, various other types of objectionable behavior may be defined based on one or more parameters. The server 202 may be deployed that is communicatively coupled to the SNP 106. The server 202 may monitor activities of the devices 108 and decide whether a predefined rule or policy is violated. A database (not shown) may manage the predefined rules and the policies. The policy may have different levels of violation.

In accordance with some embodiments, the devices 108 that are associated with the social networking platform 106 follows a Unique Device Identification (UDI) system. The UDI may require the devices 108 to bear a unique identifier that identifies that device or components thereof through manufacturing, distribution, use, and social networking phases. The UDI may allow the devices, for example, to include information in the form of a label. In an embodiment, the information may be contained in the social profiles of the devices 108 as a component of several sub-profiles. In an example, the social profile may include a sub-profile of UDI social profile managed and implemented by an application sub-component of UDI application component. In an example, the manufacturing social profile may include information in the form of an identifier that identifies the device such as 108a during a manufacturing stage, the operation social profile may include the information for identification of the device 108a during operation or distribution or use phases, and the like. In some embodiments, the UDI information may vary from one phase to another phase such as may vary during manufacturing and distribution. In some embodiments, the UDI information may remain constant. In cases when the information varies, the UDI may also associate identification information with different phases so as to correlate device identification in one phase with device identification in another phase. For example, a device such as 108a with a UDI information in a manufacturing stage or phase may be different its UDI information in the distribution but the information in both the stages may contain an information links about the information in other stages so as to correlate devices distributed information.

The UDI may contain information such as date labels in a defined format, intended use for example usable for a defined number of times, existing inventory at different supply chain stages, packaging information, lot number, batch number, serial number, manufacturing date, expiry date, storage conditions, and the like. The UDI may contain human readable codes or codes that are readable by other devices in the network 104. In an embodiment, the social networking server 202 may be programmed to read the UDI compliant codes. The UDI codes assign identification to the devices 108 such as in the form of device static data residing on the devices 108 during use in the social network 104 or dynamic data that changes over time.

The UDI system not only provides an identification system of the devices 108 in the social network 104 but also facilitates integration of the devices 108 throughout the social network 104 with the use of the social networking server so that the server 202 may identify and manages devices interactions based on the information contained in the respective UDI. In an example, the social profiles may include the UDI information so that the social server 202 may be programmed to perform searching and classification of the social profiles based on the UDI. The devices 108 may identify their respective connection devices by the UDI information and accordingly exchange the social content through the social channel to the connection devices using the UDI information contained in the social profiles of the connection devices.

The embodiments herein may be embodied as a computer program product configured to include a pre-configured set of instructions, which when performed, can result in actions as stated in conjunction with the methods described above. In an example, the pre-configured set of instructions can be stored on a tangible non-transitory computer readable medium or a program storage device. In an example, the tangible non-transitory computer readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon. Such non-transitory computer readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can include both hardware and software elements. The embodiments that are implemented in software include but are not limited to, firmware, resident software, microcode, etc. Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 22:
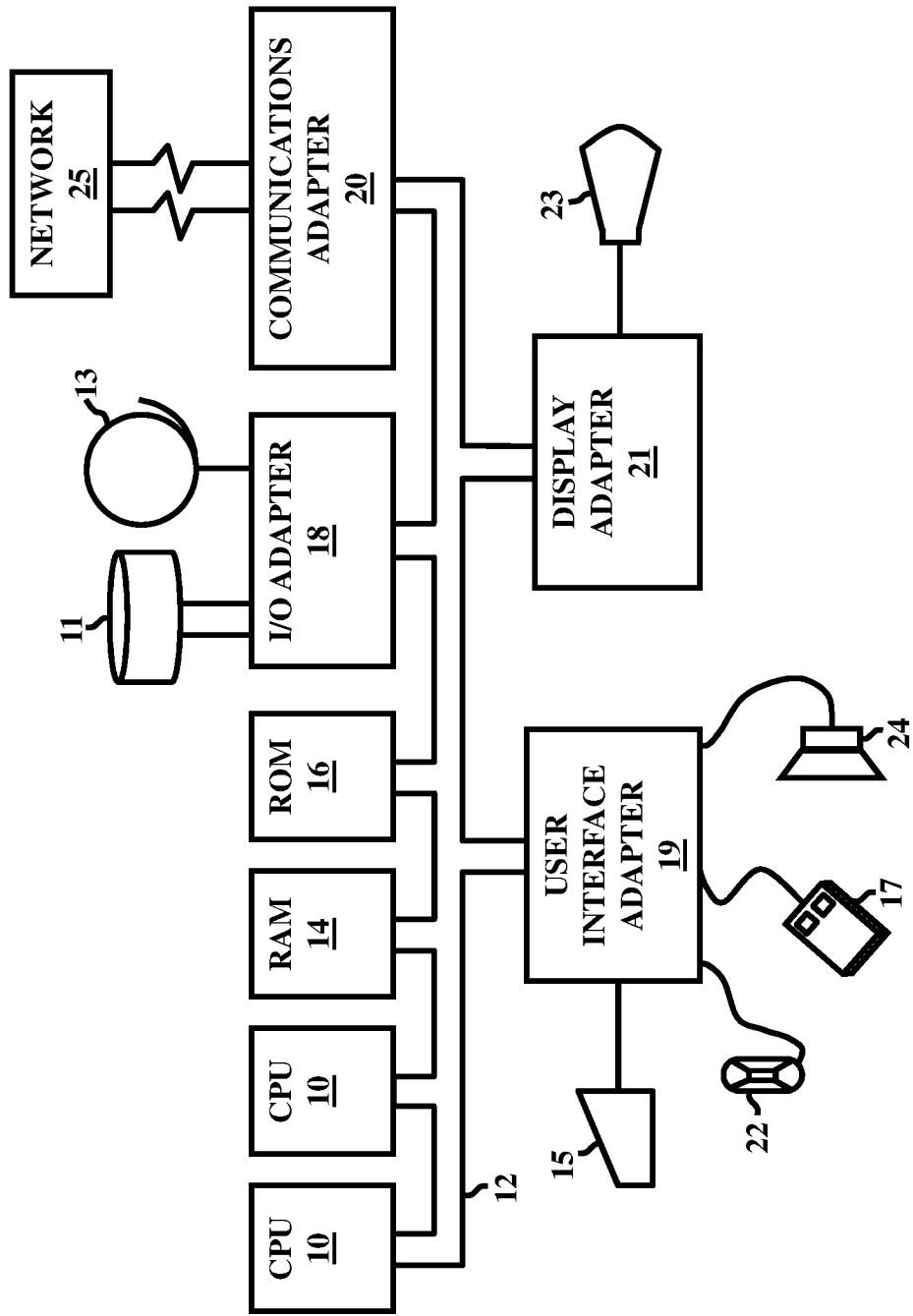
FIG. 22 is a block diagram illustrating an exemplary hardware environment for practicing the embodiments depicted in FIGS. 1-21.

A representative hardware environment for practicing the embodiments herein is depicted in FIG. 22, with reference to FIGS. 1 through 21. This schematic drawing illustrates a hardware configuration of an information handling/computer system in accordance with the embodiments herein. The system comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

A description of some exemplary embodiments can be contained in the following, without limitations.

Example 1

A system for providing a social networking service to a plurality of participants and allowing the participants to perform a series of social tasks in a socially aware network, the system comprising:

a social networking server that facilitates social information exchange among the participants through the socially aware network, the plurality of participants comprising device participants and non-device participants;

a social profiles manager included in or coupled to the social networking server, wherein the social profiles manager creates and manages individual centric profiles of devices that are a social representation of individual devices within the socially aware network, wherein the devices are identifiable by other participants and the social networking server through social profiles of the other participants, the social profiles comprising social device profiles and social human profiles associated with device participants and non-device participants respectively such that the social human profiles are associated with one or more device profiles, and wherein the social human profiles are represented as a subset of corresponding device profiles;

a social device manager included in or coupled to the social networking server, wherein the social device manager manages device relationships and social activity in the socially aware network; and a social networking application comprising a cluster of social applications each for providing a specific social facility to facilitate social activity among the plurality of participants through the socially aware network.

Example 2

The system of Example 1, wherein each of the device participants are communicatively connected with an external controller through a near field communication (NFC) channel so that a communication point of the NFC channel receives social content from a device and transfers the social content to the external controller, and wherein the external controller is communicatively coupled to the socially aware network.

Example 3

The system of Example 2, wherein a first device participant is independently incapable of performing computation tasks.

Example 4

The system of Example 3, wherein the first device participant is communicatively connected with a second device participant that is incapable of performing computation tasks, a third device participant that is partially capable of performing computation tasks, a fourth smart device that is independently capable of performing computation tasks and a non-device participant associated with one of the device participants, wherein the first device participant transfers the social content to the second device, third device, fourth device, and the non-device participant through the NFC channel and the socially aware network, wherein the socially aware network is automatically triggered upon receipt of the social content by the NFC point.

Example 5

The system of Example 1, wherein the devices comprise medical devices that are incapable of computation capabilities completely or partially.

Example 6

The system of Example 5, wherein the devices comprise medical sensors coupled to a patient's body and that are capable of sensing an environment.

Example 7

The system of Example 1, wherein the socially aware network comprises a private and dedicated network for a medical environment.

Example 8

The system of claim 1, wherein the socially aware network comprises a distributed network to allow interconnection and automation among the devices distributed in a plurality of medical environments.

Example 9

The system of Example 1, wherein the social tasks comprise one or more of: voluntarily join the socially aware network, disassociate or leave from the social network, extend interconnection with other like-minded devices, send invitations for connections to other devices, accept or reject invitations from other devices, view profiles of other devices, exchange social activity information, establish social signatures for social authorization of profiles, create devices social groups, join devices groups, and leave devices groups voluntarily or non-voluntarily through an action of a participant.

Example 10

The system of Example 1, wherein the social networking server is communicatively coupled to a social networking web-site to facilitate web-based activity by a non-device participant associated with a device participant.

Example 11

The system of Example 1, wherein the social device manager comprises:

a relationship manager that associates a relationship of a device with other devices, wherein the relationship comprises at least one of an installation relationship, time relationship, operation relationship, location relationship, reliability-based relationship, network type-relationship, security-based relationship and human relationship; and a relationship information storage module that stores information pertaining to the associated relationship among the devices.

Example 12

The system of Example 1, wherein the social networking application comprises one or more of:

a web-sharing facility that allows information exchange among the participants;

a social profiles facility that allows the participants to create respective social profiles;

a notification facility that facilitates receipt and sending of invitation notifications for extending social space of a participant;

a recommendation facility that shares recommendations for a device based on noticed past behavior of a device by a connection device;

a prediction analytics engine that determines a future behavior of the participants based on historical social data about the participants;

a social groups facility that creates a social group dedicated for the participants and exhibiting a defined behavior or belonging to a defined class;

a messaging facility that shares social content from a participant to another connection participant; and an information security facility that encrypts and decrypts the social content during exchange among the participants.

Example 13

The system of Example 1, wherein the social profiles manager comprises:

a participants profiles storage module that stores the profiles of the plurality of participants, wherein the profiles comprise a device profile and a human profile associated with the device profile, and wherein the device profile comprises a manufacturing social profile, an installation social profile, an operation social profile, a schedules social profile, a location social profile, a reliability social profile, a network social profile, a security social profile, a time profile, a location profile, and a human profile;

a profiles updating module that updates the profiles based on a change in one or more of manufacturing parameters of the devices, installation parameters of the devices, operation parameters of the devices, schedules or constraints of the devices, network parameters of the devices, reliability of the devices, security of the devices, time parameters of the devices, location of the devices, and associated non-device parameters of the devices;

a profiles aggregator that aggregates information pertinent to a manufacturing social profile of the devices, an installation social profile, an operation social profile, security profile, network profile, security profile, location profile, associated non-device profile, time profile, and a schedules social profile information into a common social profile of the devices;

a profiles federation engine that federates the common social profile into a respective manufacturing social profile, installation social profile, operation social profile, security profile, network profile, security profile, location profile, associated non-device profile, time profile, and schedules social profile.

Example 14

The system of Example 1, wherein the socially aware network comprises a Wi-Fi or internet such that the socially aware network allows interconnection and automation among a plurality of remotely located participants, and between the remotely located participants and the social networking server.

Example 15

The system of Example 1, wherein each device is communicatively coupled to a sensing and monitoring apparatus, the sensing and monitoring apparatus being communicatively coupled to an external controller that communicates with a near field communication (NFC) point through a NFC channel.

Example 16

The system of Example 15, wherein an activity of social content exchange from the external controller to the NFC point triggers the socially aware network to socially share the social content to remotely located participants through the socially aware network.

Example 17

The system of Example 15, wherein an activity of social content exchange from a 'socially aware network' point of the socially aware network to the external controller triggers a near field point of a near field network that socially shares the social content to a remotely located device associated with the external controller through the social networking server.

Example 18

The system of Example 15, wherein the NFC channel comprises a short range NFC communication network, and wherein a range of the short range communication network is substantially 100 meters to allow a device that is located within proximity of 100 meters from the external controller to communicate social content with the external controller.

Example 19

The system of Example 18, wherein the NFC network comprises a Bluetooth™ network.

Example 20

The system of Example 15, wherein the NFC channel comprises a short range communication network, and wherein a range of the short range communication network is substantially 30 feet to allow a device that is located within proximity of 30 feet from the external controller to communicate social content with the external controller.

Example 21

The system of Example 20, wherein the NFC network is based on a radio frequency identification (RFID) system such that the device comprises a RFID tag that is readable by a reader communicatively coupled to or included within the external controller.

Example 22

The system of Example 15, wherein the NFC network comprises a Body Area Network.

Example 23

The system of Example 15, wherein the devices comprise NFC tags programmable by NFC applications.

Example 24

A method for integration of a plurality of participants comprising a plurality of devices and non-devices through a social networking platform, the method comprising:
creating a device centric social profile for each of the plurality of devices, wherein the social profile comprises a social representation of a respective device within a socially aware network and each device is identifiable by other devices and a social networking server through a social profile of the each device;
allowing exchange of social content among the devices by the social networking server for the devices to perform a series of social tasks, wherein social content is exchanged through a first communication channel and a second communication channel, the first communication channel linking a device with an external controller and the second communication channel linking the external controller with a socially aware network, wherein the series social tasks comprises one or more of voluntarily joining the social network, disassociating or leaving from the socially aware network, extending interconnection with other like-minded devices, sending invitations for connections to other devices, accepting or rejecting invitations from other devices, viewing profiles of other devices, exchanging social activity information, establishing social signatures for social authorization of profiles, creating devices social groups, joining devices groups, and leaving devices groups voluntarily or upon initiation of an activity by a participant; and maintaining profiles relationships among the devices within the socially aware network.

Example 25

The method of Example 24, wherein the social profile comprises a manufacturing social profile, an installation social profile, an operation social profile, a schedules social profile, a reliability profile, a network profile, a security profile, a time profile, a location profile, and a social human profile associated for a non-device associated with a device.

Example 26

The method of Example 24, wherein at least one of the plurality of devices is at least partially incapable of computation capabilities, the device with partially incapable computation capabilities connected with the external controller through the first communication channel so that a communication point of the first communication channel is adapted to receive the social content in real-time from the device, and wherein the second channel allows information sharing between the external controller and the social networking server.

Example 27

The method of Example 24 further comprising facilitating a web-based activity among the plurality of devices for sharing the social content.

Example 28

The method of Example 24 further comprising storing information pertaining to an associated relationship of a device with other devices.

Example 29

The method of Example 28, wherein the relationship is maintained through a social map.

Example 30

The method of Example 24 further comprising facilitating a recommendation of a connection device by another device based on noticed past behavior of the connection device by the another device.

Example 31

The method of Example 24 further comprising encrypting and decrypting the social content during exchange of the social content among the devices.

Example 32

The method of Example 24 further comprising federating the social profile into a respective installation social profile, manufacturing social profile, operation social profile, schedules social profile, network social profile, security social profile, reliability social profile, human social profile, time social profile, and a location social profile.

Example 33

A method for integration of a plurality of participants comprising a plurality of devices and non-devices through a social networking platform, the method comprising:
creating a device centric social profile for each of the plurality of devices, wherein the device centric social profile is a social representation of a respective device within a socially aware network and the respective device is identifiable by other devices and a social networking server through the device centric social profile;
sending a connection invitation by a first device to a second device through a multi-communication channel that comprises a first near field communication (NFC) channel and the socially aware network, wherein the sending of the connection invitation comprises:
  sending the connection invitation from the first device to an external controller associated with the first device through the first NFC channel;
  transferring the connection invitation from the external controller to a network point of the socially aware network; and
  transferring the connection invitation from the network point through the socially aware network to the second device;
accepting or rejecting the connection invitation by the second device upon receipt;
maintaining a profiles relationship of the first device and the second device based on acceptance or rejection of the connection invitation by the second device; and
allowing exchange of a social content through a social activity between the first device and the second device based on the maintained profile relationship, wherein the social activity comprises a series of social tasks comprising one or more of: join the social network voluntarily, disassociate or leave from the social network, extend interconnection with other like-minded devices, send invitations for connections to other devices, accept or reject invitations from other devices, view profiles of other devices, exchange social activity information, establish social signatures for social authorization of profiles, create devices social groups, join devices groups, and leave devices groups voluntarily or upon initiation of an activity by a participant.

Example 34

A non-transitory program storage device readable by a computer, and comprising a program of instructions executable by the computer to perform a method for integration of a plurality of participants comprising a plurality of devices and non-devices through a social networking platform, the method comprising:
creating a device centric social profile for each of the plurality of devices, wherein the device centric social profile is a social representation of a respective device within a socially aware network and the respective device is identifiable by other devices and a social networking server through a social profile of the respective device;
allowing exchange of social content among the plurality of devices by the social networking server for the plurality of devices to perform a series of social tasks, wherein the social content is exchanged through a first communication channel and a second communication channel, the first communication channel linking a device with an external controller and the second communication channel linking the external controller with a socially aware network,
wherein the series of social tasks comprise one or more of voluntarily joining the social network, disassociating or leaving from the social network, extending interconnection with other like-minded devices, sending invitations for connections to other devices, accepting or rejecting invitations from other devices, viewing profiles of other devices, exchanging social activity information, establishing social signatures for social authorization of profiles, creating devices social groups, joining devices groups, and leaving devices groups voluntarily or upon initiation of an activity by a participant; and
maintaining profiles relationships among the plurality of devices within the socially aware network.

Example 35

A system for facilitating sequential, synchronous and automatically coordinated operation of a plurality of devices through interactive elements involving a chain of tasks and devices, the system comprising:
a social networking server that provides a social networking service to the plurality of devices so that each of the plurality of devices are communicatively connected to the social networking service by associating respective social profiles with the social networking server, the respective social profiles being social representation of the plurality of devices, wherein the social networking server is programmed to allow the plurality of devices to coordinate for a synchronous social times-based functioning by a process comprising:

associating connection type social device relationships between a first device and a second device of the plurality of devices, wherein the connection type social device relationships allow the first device and the second device to view social profiles of one another through a device user interface enabled by the social networking server;

receiving social content from the first device, wherein the social content being indicative of a social action performed by a first device and an instruction to the second device to perform an action in association with action timelines, and wherein the action timelines are indicative of time points associated with the action and define time when actual action occurs at the plurality of devices; and notifying the second device of the social content received from the first device, wherein the social content comprising the instruction to the second device to perform the action in association with the action timelines.

Example 36

The system of Example 35, wherein the plurality of devices are associated with respective external controllers that allow interconnection of the plurality of devices with the social networking server to allow a social activity through the social networking server.

Example 37

The system of Example 35, wherein the social networking server is further programmed to provide a facility to the first device to allow the first device to initiate a search request for like-minded devices based on information contained in a social profile of the first device and current operating characteristics of the first device.

Example 38

The system of Example 35, wherein the social networking server is further programmed to search for the like-minded devices from the plurality of devices and provide a list of the like-minded devices including the social profiles of the like-minded devices and network links for the like-minded devices so as to allow the first device to send a connection request to one or more of the searched like-minded devices, wherein the one or more searches like-minded devices are shortlisted by an external controller in association with an information stored in the external controller and current operating characteristics of the first device or through an intervention of a social human coordinator of the first device as identified by the social profile associated with the first device.

Example 39

The system of Example 35, wherein at least one of the plurality of devices is at least partially incapable of computation tasks.

Example 40

The system of Example 35, wherein each of the plurality of devices are connected to a sensing and monitoring unit that monitors and records activities of the plurality of devices for social exchange through a social activity.

Example 41

The system of Example 35, wherein each of the plurality of devices is communicatively connected to a respective external controller through a near field communication (NFC) channel so that a communication point of the NFC channel receives the social content from the first device and transfers the social content to an external controller associated with the first device.

Example 42

The system of Example 41, wherein the external controller is further communicatively coupled to a network point of a socially aware network, wherein when one of the network point of the socially aware network and the communication point of the NFC channel receives the social content, the other is automatically activated to further communicate the social content.

Example 43

The system of Example 42, wherein the socially aware network is a private and dedicated network for a medical environment, the social networking server allows the first device to send a connection notification to the second device through the network point of the socially aware network and the communication point of the NFC channel, and once the second device accepts the connection notification, the first device sends the social content to the second device through the network point of the socially aware network and the communication point NFC channel, wherein the social content is indicative of an action to be performed by the second device at a social event timeline specified by the social content.

Example 44

The system of Example 42, wherein the socially aware network is a distributed network, the social networking server allows the first device to send a connection notification to the second device through the network point of the socially aware network and the communication point of the NFC channel, and once the second device accepts the connection notification, the first device sends the social content to the second device through the network point of the socially aware network and the communication point NFC channel, wherein the social content is indicative of an action to be performed by the second device at a social event timeline specified by the social content.

Example 45

The system of Example 35, wherein the plurality of devices comprises medical devices that are incapable of computation capabilities completely or partially.

Example 46

The system of Example 35 further comprising a social device manager, the social device manager comprising:

a relationship manager that associates a relationship of the first device with other devices to allow coordinated interaction among the first device and the other devices to perform a patient treatment process involving a chain of tasks and device elements; and a relationship information storage module that stores information pertaining to an associated relationship between the first device and the other devices.

Example 47

The system of Example 35 further comprising a social profiles manager, wherein the social profiles manager comprising:

a device profiles storage module that stores the social profiles of the plurality of devices, wherein the social profiles comprise a manufacturing social profile, an installation social profile, an operation social profile, a reliability profile, a location profile, a time profile, a security profile, a network profile, a schedules social profile, and a social human profile;

a device profiles updating module that updates the social profiles based on a change in one or more of manufacturing parameters of the plurality of devices, installation parameters of the plurality of devices, operation parameters of the plurality of devices, schedules or constraints of the plurality of devices, reliability parameters of the plurality of devices, security parameters of the plurality of devices, network parameters of the plurality of devices, location coordinates of the plurality of devices, time coordinates of the plurality of devices and associated non-devices characteristics of the plurality of devices;

a profiles aggregator that aggregates information pertinent to a manufacturing social profile, installation social profile, operation social profile, schedules social profile, security profile, network profile, security profile, time profile location profile, associated human social profile into a common social profile of a device; and a profiles federation engine that federates the common social profile into the respective manufacturing social profile, an installation social profile, an operation social profile, a schedules social profile, security profile, network profile, security profile, time profile location profile, and the associated human social profile.

Example 48

The system of Example 36, wherein the social activity comprises posting a connection request for the second device to associate a relationship with the second device and cause a synchronous and non-conflicting performance between the first device and the second device.

Example 49

The system of Example 36, wherein the social activity comprises accepting or rejecting a connection invitation by the second device in response to a request sent by the first device for associating a relationship with the first device toward a synchronous and non-conflicting performance between the first device and the second device.

Example 50

The system of Example 35 wherein each of the plurality of devices is associated with:

a sensing unit to detect a change in performance state of a device and generate an input signal;

a database to store operation and performance parameters of the device in association with coordination and conflicting data with connections devices of the device; and an external controller associated with the device to process the generated input signal, correlate the generated signal with information stored in the database and generate a second signal that communicates social content to the social networking server.

Example 51

The system of Example 35, wherein each of the plurality of devices is associated with a switch matrix to cause the plurality of devices to change operating states based on the social content requesting a change in the operating states.

Example 52

The system of Example 35 wherein each of the plurality of devices comprises or is coupled to a health monitoring unit, wherein the health monitoring unit monitors health parameters of a device and compares with threshold health parameters of the device to ascertain health status of the device, wherein when ascertained health status is indicative of below a threshold limit, the health monitoring unit generates a signal indicative of the health status below the threshold limit, wherein the social networking server allows the device to initiate social activities that include communicating the health status to a set of connection devices so as to allow one of the connection devices to switch to a task performed by the device in case of a health failure of the device.

Example 53

The system of Example 52, wherein the health parameters of the device are identified by monitoring a set of patient's physiological parameters that are controlled by the device, wherein a drop in the set of patient's physiological parameters is indicative of the health failure of the device.

Example 54

The system of Example 35, wherein the social networking server is coupled to a social map generator, the social map generator generates a social map among the chain of tasks and devices based on connection relationships among the plurality of devices, the social map comprising a set of nodes that are representative of the plurality of devices and a set of edges connecting the nodes that are representative of connection relationships between connected devices.

Example 55

The system of Example 54, wherein an edge length in the social map represents proximity between the connected devices.

Example 56

The system of Example 54, wherein the social networking server comprises a processing unit that processes the social map for a device to identify proximity of interconnected devices.

Example 57

The system of Example 36, wherein the social activity comprises posting a search request for identification and receiving profile information of an adjacent device in the sequential, synchronous and automatically coordinated operation in response to a search request by a device, wherein upon receipt of the profile information, the device sends a connection request to the adjacent device.

Example 58

The system of Example 36, wherein the social activity comprises posting a search request for identification and receiving profile information of related devices in response to a search request by a device, wherein upon receipt of the profile information, the device sends a connection request to one or more of the related devices.

Example 59

The system of Example 35, wherein each action performed by a device connected through the social networking server is associated with a social action timeline indicative of when a particular action occurs at the device, wherein the social action timeline is communicated to connection devices for integrating the device with one or more of the connection devices.

Example 60

The system of Example 59, wherein a social profile associated with the device comprises information pertinent to the social action timeline.

Example 61

A method for facilitating sequential, synchronous, and automatically coordinated operation of a plurality of devices through interactive elements involving a chain of tasks and devices, the method comprising:
providing a social networking service by a social networking server to the plurality of devices so that each of the plurality of devices are communicatively connected to the social networking service by associating respective social profiles with the social networking server, wherein the respective social profiles comprise a social representation of the plurality of devices, and wherein the social networking server is programmed to allow the plurality of devices to coordinate for a synchronous social times-based functioning;
associating connection type social device relationships between a first device and a second device of the plurality of devices, wherein the connection type social device relationships allow the first device and the second device to view a social profile of one another through a device user interface enabled by the social networking server;
receiving social content from the first device, wherein the social content is indicative of a social action performed by the first device and an instruction to the second device to perform an action in association with action timelines, and wherein the action timelines are indicative of time points associated with the action and define time when actual action should occur at the plurality of devices; and
notifying the second device of the social content received from the first device, wherein the social content comprising the instruction to the second device to perform the action in association with the action timelines.

Example 62

The method of Example 61, wherein each of the plurality of devices are communicatively connected to an external controller through a near field communication (NFC) channel so that a communication point of the NFC channel receives the social content from the plurality of devices and transfers the social content to the external controller.

Example 63

The method of Example 62, wherein the external controller is further communicatively coupled to a network point of a socially aware network, and wherein when one of the network point of the socially aware network and the communication point of the NFC channel receives the social content, the other is automatically activated to further communicate the social content.

Example 64

The method of Example 61 further comprising generating a social map indicative of the plurality of devices and profile relationships among the plurality of devices.

Example 65

The method of Example 64, further comprising storing the social map by the social networking server so as to retrieve information from the social map to generate social proximity data, social status data, and use the social proximity data and the social status data to define precedence for a chain of tasks associated with the plurality of devices for synchronous and coordinated functioning through the social networking server.

Example 66

A non-transitory program storage device readable by a computer, and comprising a program of instructions executable by the computer to perform a method for facilitating sequential, synchronous, and automatically coordinated operation of a plurality of devices through interactive elements involving a chain of tasks and devices, the method comprising:
providing a social networking service by a social networking server to the plurality of devices so that each of the plurality of devices are communicatively connected to the social networking service by associating respective social profiles with the social networking server, wherein the respective social profiles comprise a social representation of the plurality of devices, and wherein the social networking server is programmed to allow the plurality of devices to coordinate for a synchronous social times-based functioning;
associating connection type social device relationships between a first device and a second device of the plurality of devices, wherein the connection type social device relationships allow the first device and the second device to view a social profile of one another through a device user interface enabled by the social networking server;
receiving social content from the first device, wherein the social content is indicative of a social action performed by the first device and an instruction to the second device to perform an action in association with action timelines, and wherein the action timelines are indicative of time points associated with the action and define time when actual action should occur at the plurality of devices; and
notifying the second device of the social content received from the first device, wherein the social content comprising the instruction to the second device to perform the action in association with the action timelines.

Example 67

A system for health management of a plurality of devices interconnected through a social networking platform, the system comprising:
 a social networking server that provides a social networking-based health service to the plurality of devices and allows the plurality of devices to perform a series of social health tasks by exchange of social content in a socially aware network, wherein the social networking server is programmed to:
 create and manage individual centric profiles of the plurality of devices that comprise a social representation of the individual devices within the socially aware network, wherein the individual devices are identifiable by other devices and the social networking server through social profiles of the individual devices, wherein the social profiles of each of the individual devices comprise a health profile indicative of health disciplines corresponding to each device, and a specification profile comprising details corresponding to predefined working parameters of the each device;
 associate device social relationships in the socially aware network;
 receive updates pertaining to a health profile and a specification profile of a first device through a social activity involving exchange of social content between the first device and the social networking server;
 associate a relationship between the specification profile of the first device and its health profile, wherein a mismatch between one or more parameters of the health profile and the specification profile represents a fault in the first device, and
 identify a connection device to alternatively perform a function of the first device such that the connection device is in an idle state for a time period during which the connection device is required to alternatively perform the function.

Example 68

The system of Example 67, wherein the social networking server further comprising a social networking application that comprises a cluster of social applications each for providing a specific health facility to contribute in health related social activity among the plurality of devices through the socially aware network.

Example 69

The system of Example 67 wherein the first device is incapable of computation capabilities, the first device being communicatively connected with an external controller through a near field communication (NFC) channel so that a communication point of the NFC channel receives social content from the first device and transfers the social content to the external controller, and wherein the socially aware network allows information sharing between the external controller and the social networking server in real-time.

Example 70

The system of Example 67, wherein the first device is communicatively coupled to an intelligent health monitoring device for monitoring updates in the health profile or the specification profile.

Example 71

The system of Example 70, wherein the first device is communicatively coupled to a database for storing the health profile and the specification profile and various updates corresponding to the specification profile and the health profile, and wherein the health profile and the specification profile and the various updates are shared by the intelligent health monitoring device through the social activity involving social content exchange between the health monitoring device and the social networking server.

Example 72

The system of Example 71, wherein the intelligent health monitoring device is integrally included within the first device so that the first device is capable of detecting the fault by comparing the health profile and the specification profile itself, wherein the social activity from the first device involves a request to a set of connection devices to alternatively contribute in performing a function healthily when the set of connection devices are in an idle state and when the first device is faulty.

Example 73

The system of Example 72, wherein the social activity involves sending out a connection invitation to the social networking server for identification and searching of defined social profiles, wherein the social networking server is coupled to a search interface implementing a search algorithm that identifies and shortlists the defined social profiles, the shortlisted profiles being submitted to the first device so that the first device further performs a second social activity to send out connection requests to devices associated with the shortlisted profiles for extending a social space.

Example 74

The system of Example 73, wherein the first device uses a second device from among the shortlisted social profiles as an intelligent health monitoring device based on proximity and similarity in operation of the second device with respect to the first device so that in case of a fault with or failure of the first device, the second device performs functions of the first device voluntarily or upon a social activity initiated by the first device and directed to the second device.

Example 75

A method for health management of a device interconnected with a plurality of devices through a social networking platform, the method comprising:
 creating and managing individual centric profiles of the plurality of devices that comprise a social representation of individual devices within a socially aware network, wherein the individual devices are identifiable by other devices and the social networking server through a social profile of each individual device, wherein the social profiles of each individual device comprises a health profile indicative of health disciplines corresponding to a device, and a specification profile comprising details corresponding to predefined working parameters of the device;
 associating device social relationships in the socially aware network;
 receiving updates pertaining to a health profile and a specification profile of a first device through a social activity involving social content exchange between the first device and the social networking server;

associating a relationship between the specification profile of the first device and its health profile, wherein a mismatch between one or more parameters of the health profile and the specification profile represents a fault in the first device, and identifying a connection device to alternatively perform a function of the first device such that the connection device is in an idle state for a time period during which the connection device is required to alternatively perform the function.

Example 76

The method of Example 75 further comprising informing the first device about the connection device that can perform the function in case of faults with the first device, wherein information comprises a social profile of the connection device.

Example 77

The method of Example 75 further comprising sending out a request by the first device to the connection device for alternatively performing a faulty function of the first device.

Example 78

The method of Example 75 further comprising sending out a remote message by the first device to the connection device through a social activity initiated by the first device, wherein the remote message automatically triggers the connection device to perform the function at a specified social event timeline occurrence.

Example 79

The method of Example 75 further comprising sending out an auto-correction message to the first device by a health monitoring device or a second device to trigger a fault management operation for rectifying the fault of the first device.

Example 80

The method of Example 75, wherein the first device comprises a medical device or a component thereof that is either partially or completely incapable of computations.

Example 81

A non-transitory program storage device readable by a computer, and comprising a program of instructions executable by the computer to perform a method for health management of a device interconnected with a plurality of devices through a social networking platform, the method comprising:

creating and managing individual centric profiles of the plurality of devices that comprise a social representation of individual devices within a socially aware network, wherein the individual devices are identifiable by other devices and the social networking server through a social profile of each individual device, wherein the social profiles of each individual device comprises a health profile indicative of health disciplines corresponding to a device, and a specification profile comprising details corresponding to predefined working parameters of the device;

associating device social relationships in the socially aware network;

receiving updates pertaining to a health profile and a specification profile of a first device through a social activity involving social content exchange between the first device and the social networking server;

associating a relationship between the specification profile of the first device and its health profile, wherein a mismatch between one or more parameters of the health profile and the specification profile represents a fault in the first device, and identifying a connection device to alternatively perform a function of the first device such that the connection device is in an idle state for a time period during which the connection device is required to alternatively perform the function.

Example 82

A system for monitoring and conveying health related information from a first device to a second device interconnected through a socially aware network, the system comprising:

a processing circuit coupled to the first device;

a social event timeline recorder that stores information pertinent to when a social event should occur at the first device, wherein the event should occur at a defined social time;

a social event timeline monitoring unit that monitors event occurrence time for the social event;

a fault detector that compares the social event timeline with the event occurrence time for the social event, wherein a gap between the social event timeline and the event occurrence time beyond a threshold limit is indicative of a fault, wherein the social event at the first device and the social event at the second device are interdependent; and a communication circuit that allows sharing of social content, indicative of the fault and a predicted modified event occurrence time at the first device, to a social networking server through a two-way communication channel including a near field communication channel and a socially aware network channel, wherein the social networking server sends the social content to the second device, and wherein the first device and the second device comprise connections and parts of a same chain of integrated tasks.

Example 83

The system of Example 82, wherein the social event timeline recorder further comprising a memory circuit.

Example 84

The system of Example 82, wherein each of the first device and the second device is coupled communicatively to a respective external controller so that the first device and the second device communicate with the respective external controller through the near field communication channel.

Example 85

The system of Example 82, wherein the first device and the second device comprise medical devices with partial or no computation capabilities.

Example 86

The system of Example 82, wherein the social content is exchanged through a social activity which is initiated after the first device and the second device are mutual connections.

Example 87

The system of Example 82, wherein the first device sends a connection request to the second device such that the connection request causes a display of a social profile of the first device to the second device, wherein upon acceptance of the social request after viewing the social profile of the first device, the second device and the first device are mutual connections.

Example 88

The system of Example 82 further comprising a modified social event timeline calculator to determine the predicted modified social event timeline for the first device.

Example 89

The system of Example 88 further comprising a real-time updating unit to update the social event timeline for a task based on the predicted modified social event timeline calculated by the modified social event timeline calculator.

Example 90

The system of Example 72, wherein the communication circuit shares the social content indicative of the predicted modified social event timeline to the second device through the social networking server with the use of a chat-room type window conversation setting configuring activation of social information exchange through the chat-room type window.

Example 91

The system of Example 90, wherein the chat-room type window conversation setting is activated based on a trigger generated upon detection of the fault, the trigger causing activation of the near field communication channel and the chat-room type window conversation setting.

Example 92

The system of Example 91, wherein the chat-room type window conversation setting provides a display for a user of the first device to input fault details for exchange with the second device, wherein the second device views the fault details through a display configuring a chat-room type window setting for the second device.

Example 93

A method for monitoring and conveying health related information from a first device to a second device interconnected through a socially aware network, the method comprising:

storing information related to defined social event timelines for tasks associated with the first device, wherein the defined social event timelines defining times when an event should occur at the first device;

monitoring a social event occurrence time by a social event timeline monitoring unit;

detecting a fault in functioning of the first device by comparing the defined social event timeline with an event occurrence time for the social event, wherein a gap between the defined social event timeline and the event occurrence time beyond a threshold limit is indicative of the fault, wherein the event at the first device and the event at the second device are interdependent; and sharing a social content, indicative of the fault and a predicted modified event occurrence time at the first device, to a social networking platform through a two-way communication channel including a near field communication channel and a socially aware network channel, wherein the social networking platform sends the social content to the second device, and wherein the first device and the second device comprise connections and parts of a same chain of integrated tasks.

Example 94

The method of Example 93, wherein the social content is exchanged through a social activity which is initiated after the first device and the second device are mutual connections.

Example 95

The method of Example 93 further comprising sending to the second device by the first device a connection request such that the connection request causes a display of a social profile of the first device to the second device, wherein upon acceptance of the connection request after viewing the social profile, the second device and the first device are mutual connections.

Example 96

The method of Example 93, wherein the social content indicative of the predicted modified social event timeline is shared with the second device through the social networking server with the use of a chat-room type window conversation setting configuring activation of social information exchange through a chat-room type window.

Example 97

The method of Example 96, wherein the chat-room type window conversation setting is activated based on a trigger generated upon detection of the fault, the trigger causing activation of the near field communication channel and the chat-room type window setting.

Example 98

A non-transitory program storage device readable by a computer, and comprising a program of instructions executable by the computer to perform a method for monitoring and conveying health related information from a first device to a second device interconnected through a socially aware network, the method comprising:

storing information related to defined social event timelines for tasks associated with the first device, wherein the defined social event timelines defining times when an event should occur at the first device;

monitoring a social event occurrence time by a social event timeline monitoring unit;

detecting a fault in functioning of the first device by comparing the defined social event timeline with an event occurrence time for the social event, wherein a gap between the defined social event timeline and the event occurrence time beyond a threshold limit is indicative of the fault, wherein the event at the first device and the event at the second device are interdependent; and sharing a social content, indicative of the fault and a predicted modified event occurrence time at the first device, to a social networking platform through a two-way communication channel including a near field communication channel and a socially aware network channel, wherein the social networking platform sends the social content to the second device, and wherein the first device and the second device comprise connections and parts of a same chain of integrated tasks.

Example 99

The non-transitory program storage device of Example 98, wherein the social content is exchanged through a social activity which is initiated after the first device and the second device are mutual connections.

Example 100

The non-transitory program storage device of Example 98 wherein the method further comprising sending to the second device by the first device a connection request such that the connection request causes a display of a social profile of the first device to the second device, wherein upon acceptance of the connection request after viewing the social profile, the second device and the first device are mutual connections.

Example 101

The non-transitory program storage device of Example 98, wherein the social content indicative of the predicted modified social event timeline is shared with the second device through the social networking server with the use of a chat-room type window conversation setting configuring activation of social information exchange through a chat-room type window.

Example 102

The non-transitory program storage device of Example 101, wherein the chat-room type window conversation setting is activated based on a trigger generated upon detection of the fault, the trigger causing activation of the near field communication channel and the chat-room type window conversation setting.

Example 103

A system for integration of a plurality of devices, the system comprising:
a socially aware network for communicatively linking the plurality of devices;
a social networking platform that provides a social networking service to the plurality of devices and allow them to perform a series of social tasks in the socially aware network based on defined social rules set by the social networking platform, wherein the social networking platform comprises:

a social networking server that facilitates social information exchange among the plurality of devices through the socially aware network;
a social device manager that manages relationships of the plurality of devices and social activity of the plurality of devices in the socially aware network,
a social profiles manager that creates and manages individual centric profiles of the plurality of devices that comprise a social representation of individual devices within the socially aware network, wherein the plurality of devices are identifiable by other devices and the social networking server through the individual centric social profiles; and
a social networking application comprising a cluster of social applications that provides a specific social facility to contribute toward the social activity among the plurality of devices through the socially aware network.

Example 104

The system of Example 103, wherein the plurality of devices are capable of communicating through a chat-room type window conversation setting that allows conversation among the plurality of devices by integrating the plurality of devices through the social networking server.

Example 105

The system of Example 103, wherein the system facilitates creation of separate individual centric social profiles by the plurality of devices over the social networking platform dedicated to the plurality of devices for allowing the plurality of devices to communicate through the chat room-type window conversation setting, wherein the individual centric social profiles are used as identifiers and gateways for chat rooms.

Example 106

The system of Example 105, wherein the chat room-type window conversation setting facilitates communicating health related information of the plurality of devices by exchange of information through the social networking server among the plurality of devices using the chat room-type window conversation setting and accordingly preventing damages associated with faults due to erroneous working of the plurality of devices.

Example 107

The system of Example 106 configures the chat room-type window conversation setting among related devices bearing related devices-based social profiles as identified by searching, identifying and retrieving related information and associated individual centric social profiles in response to a request submitted by a device.

Example 108

The system of Example 103, wherein the system generates a social map indicative of the plurality of devices and their relationships such that nodes of the social map represent the plurality of devices and edges of the social map represent social relationships.

Example 109

The system of Example 108, wherein the system is adapted to update the social map for structuring and analysis of the plurality of devices based on information searched and identified for related devices presented in response to a request submitted by a device, wherein an updated graph depicts added relationships.

Example 110

The system of Example 109, wherein the individual centric social profiles of the plurality of devices are created and updated by the social networking server automatically based on information collected from the social map for structuring and analysis of the plurality of devices.

Example 111

The system of Example 110, wherein the system comprises an intelligent health monitoring unit for health monitoring and health management of the plurality devices and controlling faults in operational performances by forecasting faults and scheduling alternative operations using alternative devices as identified based on the social map used for structuring and analysis of the plurality of devices.

Example 112

The system of Example 103, wherein the social networking server implements an algorithm based classification and search of trending activities and computation of weight associated with each trending activity for trending rate determination.

Example 113

The system of Example 112, wherein the trending rate is determined based on information and posts exchanged among the plurality of devices with the social networking server.

Example 114

The system of Example 113, wherein the social networking server implements an algorithm based classification and search of trending activities and computation of weight associated with each activity for trending rate determination by using the information and posts exchanged among the plurality of devices through a chat room-type window conversation setting.

Example 115

The system of Example 113, wherein the social networking platform implements an algorithm based classification and search of trending activities and computation of weight associated with each activity for:
  trending rate determination, and
  searching, identifying and presenting information and individual centric social profiles to a device in response to a request submitted by the device so that devices associated with searched individual centric social profiles exhibit trending behavior.

In various embodiments, throughout the document, the terms device participant and device are interchangeably used. Further, the term non-device participant, non-device, coordinator, human, and person are interchangeably used throughout the document. Further, terms such as device social profile, device centric profile, social device profile, and device profile are interchangeably used throughout the document. The terms such as non-device profile and human social profile are interchangeably used throughout the document. The terms social network and socially aware network are interchangeably used throughout the document. The terms server and social networking server are interchangeably used throughout the document. The term communication point and network point are interchangeably used throughout the document. The terms external controller, external programmer, and external device are interchangeably used throughout the document. The terms communication channel, network channel, and channel are interchangeably used throughout the document. The terms social map and social graph are interchangeably used throughout the document.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A system for health management of a plurality of devices interconnected through a social networking platform, said system comprising:
  a social networking server that provides a social networking-based health service to said plurality of devices and allows said plurality of devices to perform a series of social health tasks by exchange of social content in a socially aware network, wherein said social networking server is programmed to:
    create and manage individual centric profiles of said plurality of devices that comprise a social representation of individual devices within said socially aware network, wherein said individual devices are identifiable by other devices and said social networking server through social profiles of said individual devices, wherein said social profiles of each of said individual devices comprise a health profile indicative of health disciplines corresponding to each device and a specification profile comprising details corresponding to predefined working parameters of said each device;
    associate device social relationships in said socially aware network;
    receive updates pertaining to a health profile and specification profile of a device through a social activity involving social content exchange between a first device and said social networking server;
    associate a relationship between said specification profile of said device and its health profile, wherein a mismatch between one or more parameters of said health profile and said specification profile represents a fault in said device; and
    identify a connection device to alternatively perform a function of a faulty device such that said connection device is in an idle state for a time period during which said connection device is required to alternatively perform said function, wherein said first device is communicatively coupled to an intelligent health monitoring device for monitoring updates in said health profile or said specification profile, wherein said first device is communicatively coupled to a database for storing said health profile and said specification profile and various updates corresponding to said specification profile and said health profile, wherein said health profile and said specification profile and said various updates are shared by said intelligent health monitoring device through said social activity involving social content exchange between said health monitoring device and said social networking server, and wherein said intelligent health monitoring device is integrally included within said first device so that said first device is capable of detecting said fault by comparing said health profile and said specification profile itself, wherein said social activity from said first device involves a request to a set of connection devices to alternatively contribute in performing a function healthily when the set of connection devices are in an idle state and when said first device is faulty.

2. The system of claim 1, wherein said social networking server further comprising a social networking application that comprises a cluster of social applications each for providing a specific health facility to contribute in health-related social activity among said plurality of devices through said socially aware network.

3. The system of claim 1, wherein said first device is incapable of computation capabilities, said first device being communicatively connected with an external controller through a near field communication (NFC) channel so that a communication point of said NFC channel receives social content from said first device and transfers said social content to said external controller, and wherein said socially aware network allows information sharing between said external controller and said social networking server in real-time.

4. The system of claim 1, wherein said social activity involves sending out a connection invitation to said social networking server for identification and searching of defined social profiles, wherein said social networking server is coupled to a search interface implementing a search algorithm that identifies and shortlists said defined social profiles, the shortlisted profiles being submitted to said first device so that said first device further performs a second social activity to send out connection requests to devices associated with said shortlisted profiles for extending a social space.

5. The system of claim 1, wherein said first device uses a second device from among said shortlisted social profiles as an intelligent health monitoring device based on proximity and similarity in operation of said second device with respect to said first device so that in case of a fault with or failure of said first device, said second device performs functions of said first device voluntarily or upon a social activity initiated by said first device and directed to said second device.

6. A method for health management of a device interconnected with a plurality of devices through a social networking platform, said method comprising:
creating and managing individual centric profiles of said plurality of devices that comprise a social representation of individual devices within a socially aware network, wherein said individual devices are identifiable by other devices and a social networking server through a social profile of each individual device, wherein said social profile of each individual device comprises a health profile indicative of health disciplines corresponding to a device and a specification profile comprising details corresponding to predefined working parameters of said device;
associating device social relationships in the socially aware network;
receiving updates pertaining to a health profile and a specification profile of a device through a social activity involving social content exchange between a first device and the server;
associating a relationship between said specification profile of said device and its health profile, wherein a mismatch between one or more parameters of said health profile and said specification profile represents a fault in said device, and
identifying a connection device to alternatively perform a function of a faulty device such that said connection device is in an idle state for a time period during which said connection device is required to alternatively perform said function,
wherein said first device is communicatively coupled to an intelligent health monitoring device for monitoring updates in said health profile or said specification profile, wherein said first device is communicatively coupled to a database for storing said health profile and said specification profile and various updates corresponding to said specification profile and said health profile, wherein said health profile and said specification profile and said various updates are shared by said intelligent health monitoring device through said social activity involving social content exchange between said health monitoring device and said social networking server, and wherein said intelligent health monitoring device is integrally included within said first device so that said first device is capable of detecting said fault by comparing said health profile and said specification profile itself, wherein said social activity from said first device involves a request to a set of connection devices to alternatively contribute in performing a function healthily when the set of connection devices are in an idle state and when said first device is faulty.

7. The method of claim 6, further comprising informing said first device about said connection device that can perform the function in case of faults with said first device, wherein information comprises a social profile of said connection device.

8. The method of claim 6, further comprising sending out a request by said first device to said connection device for alternatively performing a faulty function of said first device.

9. The method of claim 6, further comprising sending out a remote message by said first device to said connection device through a social activity initiated by said first device, wherein said remote message automatically triggers said connection device to perform the function at a specified social event timeline occurrence.

10. The method of claim 6, further comprising sending out an auto-correction message to said first device by a health monitoring device or a second device to trigger a fault management operation for rectifying the fault of said first device.

11. The method of claim 6, wherein said first device comprises a medical device or a component thereof that is either partially or completely incapable of computations.

* * * * *